US011234994B2

(12) United States Patent
Suhy et al.

(10) Patent No.: US 11,234,994 B2
(45) Date of Patent: Feb. 1, 2022

(54) REAGENTS FOR TREATMENT OF OCULOPHARYNGEAL MUSCULAR DYSTROPHY (OPMD) AND USE THEREOF

(71) Applicant: Benitec Biopharma Limited, North Sydney (AU)

(72) Inventors: David Suhy, San Ramon, CA (US); Michael Graham, San Mateo, CA (US); Capucine Trollet, Paris (FR); Alberto Malerba, Egham (GB); John George Dickson, Egham (GB)

(73) Assignee: Benitec Biopharma Limited, Hayward, CA (US)

( * ) Notice: Subject to any disclaimer, the term of this patent is extended or adjusted under 35 U.S.C. 154(b) by 164 days.

(21) Appl. No.: 16/093,493

(22) PCT Filed: Apr. 13, 2017

(86) PCT No.: PCT/AU2017/050330
§ 371 (c)(1),
(2) Date: Oct. 12, 2018

(87) PCT Pub. No.: WO2017/177277
PCT Pub. Date: Oct. 19, 2017

(65) Prior Publication Data
US 2020/0138849 A1 May 7, 2020

Related U.S. Application Data

(60) Provisional application No. 62/322,745, filed on Apr. 14, 2016.

(51) Int. Cl.
*A61K 31/7105* (2006.01)
*A61P 27/02* (2006.01)
*A61P 21/00* (2006.01)
*A61K 31/713* (2006.01)
*A61K 48/00* (2006.01)
*C12N 15/113* (2010.01)
*C12N 15/86* (2006.01)

(52) U.S. Cl.
CPC ........ *A61K 31/7105* (2013.01); *A61K 31/713* (2013.01); *A61K 48/005* (2013.01); *A61P 21/00* (2018.01); *A61P 27/02* (2018.01); *C12N 15/113* (2013.01); *C12N 15/86* (2013.01)

(58) Field of Classification Search
CPC .... A61K 48/005; C12N 15/86; C12N 15/113; C12N 2310/14; C12N 2310/531; C12N 2320/51; C12N 2800/22
USPC ............... 435/6.1, 91.1, 91.31, 455, 458; 514/44 A, 44 R; 536/23.1, 24.5
See application file for complete search history.

(56) References Cited

U.S. PATENT DOCUMENTS

| | | | |
|---|---|---|---|
| 5,539,082 A | 7/1996 | Nielsen et al. | |
| 5,633,360 A | 5/1997 | Bischofberger et al. | |
| 5,663,312 A | 9/1997 | Chaturvedula | |
| 5,677,437 A | 10/1997 | Teng et al. | |
| 5,677,439 A | 10/1997 | Weis et al. | |
| 5,714,331 A | 2/1998 | Buchardt et al. | |
| 5,719,262 A | 2/1998 | Buchardt et al. | |
| 6,001,311 A | 12/1999 | Brennan | |
| 6,649,751 B2 | 11/2003 | Usman et al. | |
| 6,673,918 B2 | 1/2004 | Bellon et al. | |
| 6,686,463 B2 | 2/2004 | Beigelman et al. | |
| 6,989,442 B2 | 1/2006 | Vargeese | |
| 6,995,259 B1 | 2/2006 | Vargeese et al. | |
| 7,015,315 B1 | 3/2006 | Cook et al. | |
| 7,041,816 B2 | 5/2006 | Ravikumar et al. | |
| RE39,464 E | 1/2007 | Cook et al. | |
| 7,273,933 B1 | 9/2007 | Krotz et al. | |
| 7,321,029 B2 | 1/2008 | Gryaznov et al. | |
| 7,514,099 B2 | 4/2009 | Chen et al. | |
| 2001/0007666 A1 | 7/2001 | Hoffman et al. | |
| 2002/0130430 A1 | 9/2002 | Castor | |
| 2004/0214329 A1 | 10/2004 | Kay et al. | |
| 2005/0255487 A1* | 11/2005 | Khvorova | C12N 15/1048 435/6.11 |
| 2011/0212529 A1 | 9/2011 | Souza et al. | |
| 2012/0214728 A1* | 8/2012 | Van Zant | C12N 5/0647 514/1.1 |

FOREIGN PATENT DOCUMENTS

| | | |
|---|---|---|
| EP | 2907517 A1 | 8/2015 |
| KP | 20150138554 A | 12/2015 |
| RU | 2470073 C2 | 11/2001 |
| RU | 2013135484 A | 12/2011 |
| WO | 1993/023569 A1 | 11/1993 |
| WO | 1996/010390 A1 | 4/1996 |
| WO | 1996/010391 A1 | 4/1996 |
| WO | 2003/046185 A1 | 6/2003 |

(Continued)

OTHER PUBLICATIONS

Anvar et al., "A Decline in PABPN1 Induces Progressive Muscle Weakness in Oculopharyngeal Muscle Dystrophy and in Muscle Aging," Aging, 2013, vol. 5, pp. 412-426.
Apponi et al., "Loss of Nuclear Poly (A)-Binding Protein 1 Causes Defects in Myogenesis and mRNA Biogenesis," Human Molecular Genetics, 2010, vol. 19, pp. 1058-1065.
Benitec Biopharma ASX Announcement (ASX:BLT), issued on Sep. 23, 2015, titled Benitec Featured at CHF's 'Discovery on Target,' Conference (retrieved from internet May 5, 2017).
Kharma et al., "Automatied Design of Hammerhead Ribozymes and Validation by Targeting the PABPN1 Gene Transcript," Nucleic Acids Research, 2016, vol. 44, No. 4, 12 pages.

(Continued)

Primary Examiner — Jane J Zara
(74) Attorney, Agent, or Firm — Goodwin Procter LLP

(57) ABSTRACT

The present disclosure relates to RNA interference (RNAi) reagents for treatment of oculopharyngeal muscular dystrophy (OPMD), compositions comprising same, and use thereof to treat individuals suffering from OPMD or which are predisposed thereto.

21 Claims, 15 Drawing Sheets

Specification includes a Sequence Listing.

(56) References Cited

FOREIGN PATENT DOCUMENTS

| WO | 2003/097107 A2 | 11/2003 |
| WO | 2006/041617 A1 | 4/2006 |
| WO | 2010/021865 A1 | 2/2010 |
| WO | 2010/042877 A1 | 4/2010 |
| WO | 2010/080724 A1 | 7/2010 |
| WO | 2010/105209 A1 | 9/2010 |
| WO | 2011/022460 A1 | 2/2011 |
| WO | 2014/077693 A1 | 5/2014 |
| WO | 2017/177277 A1 | 10/2017 |

OTHER PUBLICATIONS

PCT International Search Report and Written Opinion, Int'l Application No. PCT/AU2017/050330, dated May 26, 2017, 12 pages.
Trollet et al., "Molecular and Phenotypic Characterization of a Mouse Model of Oculopharyngeal Muscular Dystrophy Reveals Severe Muscular Atrophy Restricted to Fast Glycolytic Fibres," (2010) Human Molecular Genetics, 19(11):2191-2207.

* cited by examiner

A.

B.

C.

D.

E.

A.

B.

C.

A.

B.

C.

E.

F.

US 11,234,994 B2

REAGENTS FOR TREATMENT OF OCULOPHARYNGEAL MUSCULAR DYSTROPHY (OPMD) AND USE THEREOF

RELATED APPLICATION DATA

The present application is a U.S. national stage of PCT/AU2017/050330 filed on 13 Apr. 2017, which claims priority from U.S. Provisional Application No. 62/322,745 filed on 14 Apr. 2016, the full contents of which is incorporated herein by reference.

REFERENCE TO A SEQUENCE LISTING SUBMITTED ELECTRONICALLY VIA EFS-WEB

This application includes a Sequence Listing submitted electronically via EFS-Web (name: "4226_0160001_SL_ST25.txt"; size: 20,864 bytes; and created on: Oct. 9, 2018), which is hereby incorporated by reference in its entirety.

TECHNICAL FIELD

The present disclosure relates to RNA interference (RNAi) reagents for treatment of oculopharyngeal muscular dystrophy (OPMD), compositions comprising same, and use thereof to treat individuals suffering from OPMD or which are predisposed thereto.

BACKGROUND

OPMD is an autosomal dominant inherited, slow progressing, late-onset degenerative muscle disorder. The disease is mainly characterised by progressive eyelid drooping (ptosis) and swallowing difficulties (dysphagia). The pharyngeal and cricopharyngeal muscles are specific targets in OPMD. Proximal limb weakness tends to follow at a later stage of disease progression. The mutation that causes the disease is an abnormal expansion of a (GCN)n trinucleotide repeat in the coding region of the poly(A) binding protein nuclear 1 (PABPN1) gene. This expansion leads to an expanded polyalanine tract at the N-terminal of the PABPN1 protein: 10 alanines are present in the normal protein, expanded to 11 to 18 alanines in the mutant form (expPABPN1). The main pathological hallmark of the disease is nuclear aggregates of expPABPN1. A misfolding of expanded PABPN1 results in the accumulation of insoluble polymeric fibrillar aggregates inside nuclei of affected cells. PABPN1 is an aggregation prone protein and mutant alanine-expanded PABPN1 in OPMD has a higher aggregation rate than that of the wild type normal protein. However, it is still unclear whether the nuclear aggregates in OPMD have a pathological function or a protective role as a consequence of a cellular defense mechanism.

No treatment, pharmacological or otherwise, is presently available for OPMD. Symptomatic surgical interventions can partly correct ptosis and improve swallowing in moderate to severely affected individuals. For example, the cricopharyngeal myotomy is at present the only possible treatment available to improve swallowing in these patients. However, this does not correct the progressive degradation of the pharyngeal musculature, which often leads to death following swallowing difficulties and chocking.

Accordingly, there remains a need for therapeutic agents to treat OPMD in patients suffering therefrom and/or who are predisposed thereto.

SUMMARY

The present disclosure is based, in part, on the recognition by the inventors that no therapeutic agents currently exist for the treatment of OPMD. The present disclosure therefore provides RNAi reagents targeting regions of the PABPN1 mRNA transcript which is causative of OPMD. The inventors have shown that these RNAi reagents are effective for post-transcription suppression of PABPN1 mRNA transcripts, including transcript variants which would otherwise be translated into the mutant PABPN1 protein causative of OPMD i.e., those PABPN1 proteins comprising an expanded polyalanine tract. For example, it has been shown that exemplary RNAi reagents of the disclosure inhibit or reduce expression of PABPN1 protein in both in vitro and in vivo models of OPMD. Furthermore, the present disclosure provides reagents for expression of wild-type human PABPN1 protein having a mRNA transcript which is not targeted by the RNAi reagents of the disclosure (hereinafter "PABPN1 replacement reagents"). The inventors have shown that when administered in conjunction with the RNAi reagents of the disclosure, the PABPN1 replacement reagents are capable of expressing PABPN1 protein having a transcript which is resistant to the RNAi reagents and which is functional. These findings by the inventors provide reagents which may have therapeutic applications in the treatment of OPMD.

Accordingly, the present disclosure provides a RNA comprising an effector sequence of at least 17 contiguous nucleotides which is substantially complementary to a region of a RNA transcript corresponding to a PABPN1 protein, wherein the region of the RNA transcript is set forth in any one of SEQ ID NOs: 1-3. Preferably, the effector sequence will be less than 30 nucleotides in length. For example, a suitable effector sequence may be in the range of 17-29 nucleotides in length.

The effector sequence may comprise 6 base pair mismatches relative to the sequence set forth in any one of SEQ ID NOs: 1-3 to which the effector sequence is substantially complementary. In another example, the effector sequence may comprise 5 base pair mismatches relative to the sequence set forth in any one of SEQ ID NOs: 1-3 to which the effector sequence is substantially complementary. In another example, the effector sequence may comprise 4 base pair mismatches relative to the sequence set forth in any one of SEQ ID NOs: 1-3 to which the effector sequence is substantially complementary. In another example, the effector sequence comprises 3 base pair mismatches relative to the sequence set forth in any one of SEQ ID NOs: 1-3 to which the effector sequence is substantially complementary. In another example, the effector sequence comprises 2 base pair mismatches relative to the sequence set forth in any one of SEQ ID NOs: 1-3 to which the effector sequence is substantially complementary. In another example, the effector sequence comprises 1 base pair mismatch relative to the sequence set forth in any one of SEQ ID NOs: 1-3 to which the effector sequence is substantially complementary. In yet another example, the effector sequence is 100% complementary to a region of equivalent length within a sequence set forth in any one of SEQ ID NOs: 1-3.

The RNA of the disclosure may be a single-stranded RNA molecule. For example, a single-stranded RNA may be selected from the group consisting of:

a RNA comprising an effector sequence which is substantially complementary to the sequence set forth in SEQ ID NO: 5 with the exception of 1, 2, 3, 4, 5 or 6 base mismatches, provided that the effector sequence is capable of forming a duplex with a sequence set forth in SEQ ID NO:5;

a RNA comprising an effector sequence which is substantially complementary to the sequence set forth in SEQ ID NO: 7 with the exception of 1, 2, 3, 4, 5 or 6 base mismatches, provided that the effector sequence is capable of forming a duplex with a sequence set forth in SEQ ID NO:7; and a RNA comprising an effector sequence which is substantially complementary to the sequence set forth in SEQ ID NO: 9 with the exception of 1, 2, 3, 4, 5 or 6 base mismatches, provided that the effector sequence is capable of forming a duplex with a sequence set forth in SEQ ID NO:9.

For example, the single-stranded RNA may comprise an effector sequence selected from the sequences set forth in SEQ ID NOs: 4, 6 or 8.

In another example, the RNA may further comprise an effector complement sequence which is substantially complementary to the effector sequence.

For example, a RNA of the disclosure may be selected from the group consisting of:

a RNA comprising (i) an effector sequence which is substantially complementary to the sequence set forth SEQ ID NO: 5 with the exception of 1, 2, 3, 4, 5 or 6 base mismatches, provided that the effector sequence is capable of forming a duplex with a sequence set forth in SEQ ID NO: 5 and (ii) an effector complement sequence comprising a sequence which is substantially complementary to the effector sequence;

a RNA comprising (i) an effector sequence which is substantially complementary to the sequence set forth in SEQ ID NO: 7 with the exception of 1, 2, 3, 4, 5 or 6 base mismatches, provided that the effector sequence is capable of forming a duplex with a sequence set forth in SEQ ID NO:7 and (ii) an effector complement sequence comprising a sequence which is substantially complementary to the effector sequence; and a RNA comprising (i) an effector sequence which is substantially complementary to the sequence set forth in SEQ ID NO: 9 with the exception of 1, 2, 3, 4, 5 or 6 base mismatches, provided that the effector sequence is capable of forming a duplex with a sequence set forth in SEQ ID NO:9 and (ii) an effector complement sequence comprising a sequence which is substantially complementary to the effector sequence.

In another example, a RNA of the disclosure may be selected from the group consisting of:

a RNA comprising an effector sequence set forth in SEQ ID NO:4 and an effector complement sequence which is substantially complementary to the sequence set forth in SEQ ID NO:4;

a RNA comprising an effector sequence set forth in SEQ ID NO:6 and an effector complement sequence which is substantially complementary to the sequence set forth in SEQ ID NO:6; and a RNA comprising an effector sequence set forth in SEQ ID NO:8 and an effector complement sequence which is substantially complementary to the sequence set forth in SEQ ID NO:8.

For example, an effector complement sequence of a RNA of the disclosure may comprise 1, 2, 3, 4, 5 or 6 mismatches relative to the corresponding effector sequence provided that the cognate effector and effector complement sequences are capable of forming a duplex.

In another example, the RNA of the disclosure is selected from the group consisting of:

a RNA comprising an effector sequence set forth in SEQ ID NO:4 and an effector complement sequence set forth in SEQ ID NO:5;

a RNA comprising an effector sequence set forth in SEQ ID NO:6 and an effector complement sequence set forth in SEQ ID NO:7; and a RNA comprising an effector sequence set forth in SEQ ID NO:8 and an effector complement sequence set forth in SEQ ID NO:9.

It will therefore be appreciated that the RNA of the disclosure may be provided in the form of a short interfering RNA (siRNA) duplex or a double-stranded RNA (dsRNA).

Alternatively, the RNA of the disclosure may be provided in the form of a short hairpin RNA (shRNA). When provided as a shRNA, the RNA of the disclosure may comprise a loop sequence positioned between the effector sequence and the effector complement sequence. Suitable loop sequences may be selected from those known in the art. For example, a shRNA in accordance with the present disclosure may comprise any combination of effector and effector complement sequences described herein with a stem loop sequence positioned there between.

In one example, the RNA of the disclosure is selected from the group consisting of:

a shRNA comprising (i) an effector sequence set forth in SEQ ID NO:10, (ii) an effector complement sequence which is substantially complementary to the sequence set forth in SEQ ID NO:10, and (iii) a stem loop sequence positioned between the effector sequence and the effector complement sequence;

a shRNA comprising (i) an effector sequence set forth in SEQ ID NO:12, (ii) an effector complement sequence which is substantially complementary to the sequence set forth in SEQ ID NO:12, and (iii) a stem loop sequence positioned between the effector sequence and the effector complement sequence; and a shRNA comprising (i) an effector sequence set forth in SEQ ID NO:14, (ii) an effector complement sequence which is substantially complementary to the sequence set forth in SEQ ID NO:14, and (iii) a stem loop sequence positioned between the effector sequence and the effector complement sequence.

In one example, the RNA of the disclosure is selected from the group consisting of:

a shRNA comprising (i) an effector sequence set forth in SEQ ID NO:10, (ii) an effector complement sequence set forth in SEQ ID NO:11, and (iii) a stem loop sequence positioned between the effector sequence and the effector complement sequence;

a shRNA comprising (i) an effector sequence set forth in SEQ ID NO:12, (ii) an effector complement sequence set forth in SEQ ID NO:13, and (iii) a stem loop sequence positioned between the effector sequence and the effector complement sequence; and a shRNA comprising (i) an effector sequence set forth in SEQ ID NO:14, (ii) an effector complement sequence set forth in SEQ ID NO:15, and (iii) a stem loop sequence positioned between the effector sequence and the effector complement sequence.

For example, a shRNA in accordance with the present disclosure may comprise a sequence set forth in any one of SEQ ID NOs: 16-21.

It will be understood by a person of skill in the art that a RNA in accordance with the present disclosure may be combined or used in conjunction with other therapeutic agents for treating OPMD. Accordingly, the present disclosure provides a RNA as described herein in combination with one or more other agents for treating OPMD. In one example, a plurality of RNAs are provided comprising:
(a) at least one RNA as described herein; and
(b) at least one RNA selected from:
  (i) a RNA as described herein; or
  (ii) a RNA comprising an effector sequence of at least 17 contiguous nucleotides which is substantially complementary to a region of the RNA transcript corresponding to a PABPN1 protein which is causative of OPMD;
wherein the RNA at (a) and the RNA at (b) comprise different effector sequences.

In one example, the RNA at (b) is a RNA as described herein.

In one example, a plurality of RNAs of the disclosure comprises at least two RNAs selected from:
(a) a first RNA comprising an effector sequence of at least 17 contiguous nucleotides which is substantially complementary to the sequence set forth in SEQ ID NO: 1, as described herein;
(b) a second RNA comprising an effector sequence of at least 17 contiguous nucleotides which is substantially complementary to the sequence set forth in SEQ ID NO: 2, as described herein; and
(c) a third RNA comprising an effector sequence of at least 17 contiguous nucleotides which is substantially complementary to the sequence set forth in SEQ ID NO: 3, as described herein.

In one example, at least one or each of the RNAs in the plurality is a ssRNA selected from the ssRNAs described herein. For example, a plurality of RNAs of the disclosure may comprise at least two ssRNAs selected from the group consisting of:
(a) a first RNA comprising an effector sequence set forth in SEQ ID NO: 4;
(b) a second RNA comprising an effector sequence set forth in SEQ ID NO: 6; and
(c) a third RNA comprising an effector sequence set forth in SEQ ID NO: 8.

In one example, at least one or each of the RNAs in the plurality is a dsRNA selected from the dsRNAs described herein. For example, a plurality of RNAs of the disclosure may comprise at least two dsRNAs selected from the group consisting of:
(a) a first RNA comprising an effector sequence set forth in SEQ ID NO:4 and an effector complement sequence which is substantially complementary to the sequence set forth in SEQ ID NO:4 e.g., a sequence set forth in SEQ ID NO:5;
(b) a second RNA comprising an effector sequence set forth in SEQ ID NO:6 and an effector complement sequence which is substantially complementary to the sequence set forth in SEQ ID NO:6 e.g., a sequence set forth in SEQ ID NO:7; and
(c) a third RNA comprising an effector sequence set forth in SEQ ID NO:8 and an effector complement sequence which is substantially complementary to the sequence set forth in SEQ ID NO:8 e.g., a sequence set forth in SEQ ID NO:9.

In another example, at least one or each of the RNAs in the plurality of RNAs described herein may be present in the form of a shRNA. As described herein, each shRNA of the plurality will comprise a stem loop sequence positioned between the corresponding effector sequence and effector complement sequence such that the shRNA forms a single contiguous sequence. For example, a plurality of shRNAs of the disclosure may comprise at least two RNAs selected from the group consisting of:

(a) a first RNA comprising (i) an effector sequence set forth in SEQ ID NO: 10, (ii) an effector complement sequence which is substantially complementary to the sequence set forth in SEQ ID NO: 10 e.g., a sequence set forth in SEQ ID NO: 11, and (iii) a stem loop sequence positioned between the effector sequence and the effector complement sequence;
(b) a second RNA comprising (i) an effector sequence set forth in SEQ ID NO: 12, (ii) an effector complement sequence which is substantially complementary to the sequence set forth in SEQ ID NO:12 e.g., a sequence set forth in SEQ ID NO:13, and (iii) a stem loop sequence positioned between the effector sequence and the effector complement sequence; and
(c) a third RNA comprising (i) an effector sequence set forth in SEQ ID NO: 14, (ii) an effector complement sequence which is substantially complementary to the sequence set forth in SEQ ID NO: 14 e.g., a sequence set forth in SEQ ID NO: 15, and (iii) a stem loop sequence positioned between the effector sequence and the effector complement sequence.

As described herein, the plurality of RNAs of the disclosure may comprise the first RNA and the second RNA as described herein. In another example, the plurality of RNAs of the disclosure comprises the first RNA and the third RNA as described herein. In another example, the plurality of RNAs of the disclosure comprises the second RNA and the third RNA as described herein. In yet another example, the plurality of RNAs of the disclosure comprises the first RNA, the second RNA and the third RNA as described herein.

A plurality of RNAs in accordance with the present disclosure may comprise up to 10 RNAs, such as two RNAs or three RNAs or four RNAs or five RNAs or six RNAs or seven RNAs or eight RNAs or nine RNAs or ten RNAs. In one example, the plurality of RNAs comprises two of the RNAs described herein. In another example, the plurality of RNAs comprises three of the RNAs described herein.

According to one example of the disclosure in which a plurality of shRNAs are provided, the plurality comprises or consists of:
(i) a shRNA comprising or consisting of the sequence set forth in SEQ ID NO: 16; and
(ii) a shRNA comprising or consisting of the sequence set forth in SEQ ID NO: 18.

According to one example of the disclosure in which a plurality of shRNAs are provided, the plurality comprises or consists of:
(i) a shRNA comprising or consisting of the sequence set forth in SEQ ID NO: 16; and
(ii) a shRNA comprising or consisting of the sequence set forth in SEQ ID NO: 20.

According to one example of the disclosure in which a plurality of shRNAs are provided, the plurality comprises or consists of:
(i) a shRNA comprising or consisting of the sequence set forth in SEQ ID NO: 18; and
(ii) a shRNA comprising or consisting of the sequence set forth in SEQ ID NO: 20.

According to one example of the disclosure in which a plurality of shRNAs are provided, the plurality comprises or consists of:
(i) a shRNA comprising or consisting of the sequence set forth in SEQ ID NO: 16;
(ii) a shRNA comprising or consisting of the sequence set forth in SEQ ID NO: 18; and
(iii) a shRNA comprising or consisting of the sequence set forth in SEQ ID NO: 20.

In one example, the plurality of RNAs described herein may be provided together as a single composition.

In one example, the plurality of RNAs described herein may be provided as multiple compositions. For example, each of the RNAs of the plurality may be provided separately. Alternatively, at least one RNA of the plurality may be provided separately and two or more of the plurality provided together in a composition.

The or each RNA of the disclosure may be a DNA-directed RNA (ddRNA) which can be transcribed from a nucleic acid. Accordingly, the present disclosure also provides a DNA-directed RNAi (ddRNAi) construct comprising a nucleic acid comprising a DNA sequence encoding a RNA of the disclosure e.g., wherein the RNA is a shRNA as described herein.

The DNA sequence encoding the shRNA may comprise a DNA sequence encoding a loop sequence positioned between the effector sequence and the effector complement sequence. For example, a DNA sequence encoding a shRNA of the disclosure may be selected from the group consisting of a sequence set forth in any one of SEQ ID NOs: 16-21. In one example, the DNA sequence encoding a shRNA of the disclosure may also comprise a terminator sequence at the 3' terminus.

In another example, the present disclosure provides a ddRNAi construct capable of expressing a plurality of shRNAs. For example, a ddRNAi construct of the disclosure may comprise a nucleic acid comprising one or more DNA sequence(s) encoding a plurality of RNAs of the disclosure e.g., wherein each of the RNAs is a shRNA as described herein.

In one example, the ddRNAi construct may comprise at least two nucleic acids selected from the group consisting of:
(a) a first nucleic acid comprising a DNA sequence encoding a shRNA sequence comprising:
  (i) an effector sequence comprising a region of at least 17 contiguous nucleotides which is substantially complementary to the PABPN1 sequence set forth in SEQ ID NO: 1; and
  (ii) an effector complement sequence which is substantially complementary to the effector sequence;
(b) a second nucleic acid comprising a DNA sequence encoding a shRNA sequence comprising:
  (i) an effector sequence comprising a region of at least 17 contiguous nucleotides which is substantially complementary to the PABPN1 sequence set forth in SEQ ID NO: 2; and
  (ii) an effector complement sequence which is substantially complementary to the effector sequence; and
(c) a third nucleic acid comprising a DNA sequence encoding a shRNA sequence comprising:
  (i) an effector sequence comprising a region of at least 17 contiguous nucleotides which is substantially complementary to the PABPN1 sequence set forth in SEQ ID NO: 3; and
  (ii) an effector complement sequence which is substantially complementary to the effector sequence.

In one example, the DNA sequence comprised within the first nucleic acid encodes a shRNA sequence comprising an effector sequence set forth in SEQ ID NO: 10 and an effector complement sequence set forth in SEQ ID NO: 11.

In one example, the DNA sequence comprised within the second nucleic acid encodes a shRNA sequence comprising an effector sequence set forth in SEQ ID NO: 12 and an effector complement sequence set forth in SEQ ID NO: 13.

In one example, the DNA sequence comprised with the third nucleic acid encodes a shRNA sequence comprising an effector sequence set forth in SEQ ID NO: 14 and an effector complement sequence set forth in SEQ ID NO: 15.

Each nucleic acid comprising a DNA sequence encoding a shRNA as described herein may comprise a DNA sequence encoding a loop sequence positioned between the cognate effector sequence and the effector complement sequence.

In one example, the first nucleic acid comprises a DNA sequence encoding a shRNA sequence set forth in SEQ ID NO: 16 or 17.

In one example, the second nucleic acid comprises a DNA sequence encoding a shRNA sequence set forth in SEQ ID NO: 18 or 19.

In one example, the third nucleic acid comprises a DNA sequence encoding a shRNA sequence set forth in SEQ ID NO: 20 or 21.

Each of the shRNAs described herein may optionally further comprise two contiguous uracils (UU) at the 3' end of the shRNA e.g., as a consequence of transcriptional termination from a RNA Pol III promoter.

Each nucleic acid may also comprise a terminator sequence at the 3' terminus of the DNA sequence encoding the shRNA.

In one example, the ddRNAi construct capable of expressing a plurality of RNAs comprises the first nucleic acid described herein and the second nucleic acid described herein. In one example, the ddRNAi construct capable of expressing a plurality of RNAs comprises the first nucleic acid described herein and the third nucleic acid described herein. In one example, the ddRNAi construct capable of expressing a plurality of RNAs comprises the second nucleic acid described herein and the third nucleic acid described herein. In one example, the ddRNAi construct capable of expressing a plurality of RNAs comprises the first nucleic acid described herein, the second nucleic acid described herein and the third nucleic acid described herein.

An exemplary ddRNAi construct capable of expressing three shRNAs of the disclosure comprises:
a first nucleic acid comprising a DNA sequence encoding a shRNA sequence set forth in SEQ ID NO: 16;
a second nucleic acid comprising a DNA sequence encoding a shRNA sequence set forth in 18; and
a third nucleic acid comprising a DNA sequence encoding a shRNA sequence set forth in SEQ ID NO: 20.

Each of the shRNAs described herein may optionally further comprise two contiguous uracils (UU) at the 3' end of the shRNA e.g., as a consequence of transcriptional termination from a RNA Pol III promoter.

In one example, the ddRNAi construct as described herein comprises a single promoter which is operably-linked to the or each nucleic acid encoding a shRNA of the disclosure.

In another example, each nucleic acid encoding a shRNA of the disclosure is operably-linked to a separate promoter. For example, the promoter(s) is(are) positioned upstream of the respective DNA sequences(s) encoding the shRNA(s). In a ddRNAi construct comprising multiple promoters, the promoters may be the same or different. Exemplary promoters are RNA pol III promoters, such as for example, the U6 and H1 promoters.

In accordance with the example of the ddRNAi construct which is capable of expressing three shRNAs of the disclosure, the ddRNAi construct may comprise:
(a) a U6-1 promoter upstream of the first nucleic acid comprising DNA sequence encoding a shRNA sequence set forth in SEQ ID NO: 16;
(b) a U6-9 promoter upstream of the second nucleic acid comprising DNA sequence encoding a shRNA sequence set forth in SEQ ID NO: 18; and (c) a H1 promoter upstream of the third nucleic acid comprising DNA sequence encoding a shRNA sequence set forth in SEQ ID NO: 20.

In one example, the ddRNAi construct which is capable of expressing three shRNAs of the disclosure comprises a sequence set forth in SEQ ID NO: 22. In one example, the ddRNAi construct which is capable of expressing three shRNAs of the disclosure comprises a sequence set forth in SEQ ID NO: 23.

In yet another example, the present disclosure provides a plurality of ddRNAi constructs, each ddRNAi construct capable of expressing at least one shRNA described herein. The plurality of ddRNAi constructs may comprise at least two ddRNAi constructs selected from the group consisting of:

(a) a first ddRNAi construct comprising a nucleic acid comprising a DNA sequence encoding a shRNA sequence comprising:
  (i) an effector sequence comprising a region of at least 17 contiguous nucleotides which is substantially complementary to the PABPN1 sequence set forth in SEQ ID NO: 1; and
  (ii) an effector complement sequence which is substantially complementary to the effector sequence;
(b) a second ddRNAi construct comprising a nucleic acid comprising a DNA sequence encoding a shRNA sequence comprising:
  (i) an effector sequence comprising a region of at least 17 contiguous nucleotides which is substantially complementary to the PABPN1 sequence set forth in SEQ ID NO: 2; and
  (ii) an effector complement sequence which is substantially complementary to the effector sequence; and
(c) a third ddRNAi construct comprising a nucleic acid comprising a DNA sequence encoding a shRNA sequence comprising:
  (i) an effector sequence comprising a region of at least 17 contiguous nucleotides which is substantially complementary to the PABPN1 sequence set forth in SEQ ID NO: 3; and
  (ii) an effector complement sequence which is substantially complementary to the effector sequence.

In one example, the first ddRNAi construct comprises a nucleic acid comprising a DNA sequence encoding an effector sequence set forth in SEQ ID NO: 10 and an effector complement sequence set forth in SEQ ID NO: 11.

In one example, the second ddRNAi construct comprises a nucleic acid comprising a DNA sequence encoding an effector sequence set forth in SEQ ID NO: 12 and an effector complement sequence set forth in SEQ ID NO: 13.

In one example, the third ddRNAi construct comprises a nucleic acid comprising a DNA sequence encoding an effector sequence set forth in SEQ ID NO: 14 and an effector complement sequence set forth in SEQ ID NO: 15.

In each of the ddRNAi constructs in the plurality, the DNA sequence encoding the respective shRNAs may comprise a DNA sequence encoding a loop sequence positioned between the respective effector sequence and the effector complement sequence.

In one example, the first ddRNAi construct comprises a nucleic acid comprising a DNA sequence encoding a shRNA sequence set forth in SEQ ID NO: 16 or 17.

In one example, the second ddRNAi construct comprises a nucleic acid comprising a DNA sequence encoding a shRNA sequence set forth in SEQ ID NO: 18 or 19.

In one example, the third ddRNAi construct comprises a nucleic acid comprising a DNA sequence encoding a shRNA sequence set forth in SEQ ID NO: 20 or 21.

In each of the ddRNAi constructs, the or each nucleic acid may also comprise a terminator sequence at the 3' terminus of the DNA sequence encoding the shRNA.

Each of the shRNAs expressed from the ddRNAi construct may also optionally further comprise two contiguous uracils (UU) at the 3' end of the shRNA e.g., as a consequence of transcriptional termination from a RNA Pol III promoter.

In one example, the plurality of ddRNAi constructs comprises the first ddRNAi construct described herein and the second ddRNAi construct described herein. In one example, the plurality of ddRNAi constructs comprises the first ddRNAi construct described herein and the third ddRNAi construct described herein. In one example, the plurality of ddRNAi constructs comprises the second ddRNAi construct described herein and the third ddRNAi construct described herein. In one example, the plurality of ddRNAi constructs comprises the first ddRNAi construct described herein, the second ddRNAi construct described herein and the third ddRNAi construct described herein.

An exemplary plurality of ddRNAi constructs comprises:
a first ddRNAi construct comprising a nucleic acid comprising a DNA sequence encoding a shRNA sequence set forth in SEQ ID NO: 16;
a second ddRNAi construct comprising a nucleic acid comprising a DNA sequence encoding a shRNA sequence set forth in SEQ ID NO: 18; and
a third ddRNAi construct comprising a nucleic acid comprising a DNA sequence encoding a shRNA sequence set forth in SEQ ID NO: 20.

Each ddRNAi construct in the plurality of ddRNAi constructs may comprise a promoter which is operably-linked to the or each nucleic acid encoding a shRNA of the disclosure.

According to an example in which one or more of the ddRNAi constructs in plurality is capable of expressing more than one shRNA, each nucleic acid encoding a shRNA may be operably-linked to a separate promoter. For example, the promoter(s) is(are) positioned upstream of the respective DNA sequences(s) encoding the shRNA(s). In a ddRNAi construct comprising multiple promoters, the promoters may be the same or different. Exemplary promoters are RNA pol III promoters, such as for example, the U6 and H1 promoters.

The or each ddRNAi construct as described herein may be comprised within an expression vector.

According to an example in which a plurality of ddRNAi constructs are present, a plurality of expression vectors comprising the ddRNAi may be provided. In one example, one or more of the plurality of expression vectors comprises a plurality of ddRNAi constructs as disclosed herein. In another example, each ddRNAi construct in the plurality is comprised within a separate expression vector. In any of the foregoing ways in this paragraph, the plurality of expression vectors may collectively express a plurality of shRNAs in accordance with the present disclosure.

The present disclosure also provides a composition comprising a ddRNAi construct, a plurality of ddRNAi constructs, an expression vector and/or a plurality of expression vectors as described herein. In one example, the composition may also comprise one or more pharmaceutically acceptable carriers and/or diluents.

In one example, a composition of the disclosure further comprises a nucleic acid encoding a functional PABPN1 protein having a mRNA transcript which is not targeted by the or each shRNA encoded by the ddRNAi construct(s) in the composition. For example, the functional PABPN1 protein is a wild-type human PABPN1 protein e.g., having a sequence set forth in SEQ ID NO: 25.

In one example, the nucleic acid encoding the functional PABPN1 protein is codon-optimised so that the mRNA transcribed therefrom is not targeted by the or each shRNA encoded by the ddRNAi construct(s) in the composition. In one example, the nucleic acid encoding the functional PABPN1 protein comprises the sequence set forth in SEQ ID NO: 24. In one example, the nucleic acid encoding the functional PABPN1 protein may also comprise a kozak sequence at the 5' end.

The nucleic acid encoding the functional PABPN1 protein as disclosed herein will be comprised within an expression vector.

In accordance with an example in which the or each ddRNAi construct is/are comprised within a single expression vector, the ddRNAi construct(s) and the nucleic acid encoding the functional PABPN1 protein may be comprised within the same expression vector. Alternatively, the ddRNAi construct(s) and the nucleic acid encoding the functional PABPN1 protein may be comprised within different expression vectors.

In accordance with an example in which a plurality of ddRNAi constructs of the disclosure are comprised within a plurality of expression vectors, each ddRNAi construct may be comprised within a different expression vector and the nucleic acid encoding the functional PABPN1 protein may be comprised within at least one of the expression vectors comprising a ddRNAi construct.

In one example, the or each expression vector is a plasmid or a minicircle.

In one example, the or each plasmid or minicircle or expression vector or ddRNAi construct is complexed with a cationic DNA binding polymer e.g., polyethylenimine.

In another example, the or each expression vector is a viral vector. For example, the viral vector is selected from the group consisting of an adeno-associated viral (AAV) vector, a retroviral vector, an adenoviral vector (AdV) and a lentiviral (LV) vector.

The present disclosure also provides a nucleic acid encoding a functional PABPN1 protein having a mRNA transcript which is not targeted by one or more of the RNAs e.g., shRNAs, described herein as targeting the wild-type mRNA transcript of the PABPN1 protein. In one example, the functional PABPN1 protein encoded by the nucleic acid of the disclosure may have the same amino acid sequence of the wild-type human PABPN1 protein e.g., having a sequence set forth in SEQ ID NO: 25. The nucleic acid of the disclosure which encodes the functional PABPN1 protein may be codon-optimised so that the mRNA transcribed therefrom is not targeted by the one or more RNAs e.g., shRNAs, described herein as targeting the wild-type mRNA transcript of the PABPN1 protein. In one example, the nucleic acid encoding the functional PABPN1 protein comprises the sequence set forth in SEQ ID NO: 24. In one example, the nucleic acid encoding the functional PABPN1 protein may also comprise a kozak sequence at the 5' end. The nucleic acid encoding the functional PABPN1 protein as disclosed herein may be comprised within an expression vector. The expression vector may be any expression vector as described herein above in the context of ddRNAi constructs of the disclosure. As also described herein above, the expression vector comprising the nucleic acid encoding the functional PABPN1 protein may also comprise one or more ddRNAi construct(s) of the disclosure.

The nucleic acid encoding a functional PABPN1 protein of the disclosure may be useful for treating OPMD in combination with, or in a subject who has already received treatment with, a RNA, a plurality of RNAs, a ddRNAi construct, a plurality of ddRNAi constructs, an expression vector, a plurality of expression vectors and/or composition described herein.

The present disclosure also provides a method of inhibiting expression of a PABPN1 protein which is causative of OPMD in a subject, the method comprising administering to the subject a RNA, a plurality of RNAs, a ddRNAi construct, a plurality of ddRNAi constructs, an expression vector, a plurality of expression vectors and/or composition described herein.

The present disclosure also provides a method of treating OPMD in a subject suffering therefrom, the method comprising administering to the subject a RNA, a plurality of RNAs, a ddRNAi construct, a plurality of ddRNAi constructs, an expression vector, a plurality of expression vectors and/or composition described herein. The method of treating OPMD may further comprise administering to the subject a nucleic acid encoding a functional PABPN1 protein as described herein.

The present disclosure also provides a method of treating OPMD in a subject suffering therefrom, the method comprising administering to the subject a nucleic acid encoding a functional PABPN1 protein of the disclosure, wherein the subject has previously been administered a RNA, a plurality of RNAs, a ddRNAi construct, a plurality of ddRNAi constructs, an expression vector, a plurality of expression vectors and/or composition described herein. The present disclosure also provides a method of treating OPMD in a subject suffering therefrom, the method comprising administering to the subject:

(a) one or more agents for inhibiting expression of a PABPN1 protein which is causative of OPMD, said agent(s) selected from: (i) a RNA, a plurality of RNAs, a ddRNAi construct, a plurality of ddRNAi constructs, an expression vector, a plurality of expression vectors and/or composition described herein; and (b) an expression vector comprising a nucleic acid encoding a functional PABPN1 protein having a mRNA transcript which is not targeted by the agent at (a).

In one example, the functional PABPN1 protein comprises the amino acid sequence of a wild-type human PABPN1 protein e.g., having a sequence set forth in SEQ ID NO: 25.

In one example, the nucleic acid encoding the functional PABPN1 protein is codon-optimised so that the mRNA transcribed therefrom is not targeted by agent at (a) which acts via RNAi. In one example, the nucleic acid encoding the functional PABPN1 protein comprises the sequence set forth in SEQ ID NO: 24. In one example, the nucleic acid encoding the functional PABPN1 protein may also comprise a kozak sequence at the 5' end.

In one example, the agent(s) at (a) and the expression vector at (b) are administered to the subject together. In one example, the agent(s) at (a) and the expression vector at (b) are administered to the subject separately but simultaneously. In one example, the agent(s) at (a) and the expression vector at (b) are administered to the subject consecutively.

The present disclosure also provides a kit comprising:

(a) one or more agents for inhibiting expression of a PABPN1 protein which is causative of OPMD, said agent(s) selected from: (i) a RNA, a plurality of RNAs, a ddRNAi construct, a plurality of ddRNAi constructs, an expression vector, a plurality of expression vectors and/or composition described herein; and (b) an expression vector comprising a nucleic acid encoding a functional PABPN1 protein having a mRNA transcript which is not targeted by the agent at (a).

In one example, the functional PABPN1 protein is a wild-type human PABPN1 protein e.g., having a sequence set forth in SEQ ID NO: 25.

In one example, the nucleic acid encoding the functional PABPN1 protein is codon-optimised so that the mRNA transcribed therefrom is not targeted by agent at (a) which acts via RNAi. In one example, the nucleic acid encoding the functional PABPN1 protein comprises the sequence set forth in SEQ ID NO: 24. In one example, the nucleic acid encoding the functional PABPN1 protein may also comprise a kozak sequence at the 5' end.

In one example, the kit further comprises instructions for use in a method of the disclosure.

The present disclosure also provides use of a RNA, a plurality of RNAs, a ddRNAi construct, a plurality of ddRNAi constructs, an expression vector, a plurality of expression vectors and/or composition described herein in the preparation of a medicament for treating or preventing OPMD in a subject.

The present disclosure also provides use of a nucleic acid encoding a functional PABPN1 protein as described herein in the preparation of a medicament for treating or preventing OPMD in a subject. Treatment of OPMD in accordance with this example may comprise administering the medicament to the subject in combination with an agent which acts via RNAi which is selected from a RNA, a plurality of RNAs, a ddRNAi construct, a plurality of ddRNAi constructs, an expression vector, a plurality of expression vectors and/or composition described herein, wherein the nucleic acid encoding the functional PABPN1 protein has a mRNA transcript which is not targeted by the agent which acts via RNAi. In accordance with another example, treatment of OPMD may comprise administering the medicament to a subject who has already been administered an agent which acts via RNAi which is selected from a RNA, a plurality of RNAs, a ddRNAi construct, a plurality of ddRNAi constructs, an expression vector, a plurality of expression vectors and/or composition described herein, wherein the nucleic acid encoding the functional PABPN1 protein has a mRNA transcript which is not targeted by the agent which acts via RNAi.

The present disclosure also provides use of an expression vector comprising a nucleic acid encoding a functional PABPN1 protein in the preparation of a medicament for treating or preventing OPMD in a subject, wherein the medicament comprises an agent which acts via RNAi which is selected from a RNA, a plurality of RNAs, a ddRNAi construct, a plurality of ddRNAi constructs, an expression vector, a plurality of expression vectors and/or composition described herein, and wherein the functional PABPN1 protein has a mRNA transcript which is not targeted by the agent.

In one example, the functional PABPN1 protein has the amino acid sequence of a wild-type human PABPN1 protein e.g., having a sequence set forth in SEQ ID NO: 25.

In one example, the nucleic acid encoding the functional PABPN1 protein is codon-optimised so that the mRNA transcribed therefrom is not targeted by agent. In one example, the nucleic acid encoding the functional PABPN1 protein comprises the sequence set forth in SEQ ID NO: 24.

In one example, the nucleic acid encoding the functional PABPN1 protein may also comprise a kozak sequence at the 5' end.

In each of the foregoing examples, the subject to be treated may be suffering from OPMD or may be genetically predisposed to OPMD.

The present disclosure also provides a RNA, a plurality of RNAs, a ddRNAi construct, a plurality of ddRNAi constructs, an expression vector, a plurality of expression vectors, a composition and/or a kit as described herein for use in therapy. For example, the RNA, plurality of RNAs, ddRNAi construct, plurality of ddRNAi constructs, expression vector, plurality of expression vectors, composition and/or kit may be for use in treating OPMD in a subject and/or in a method disclosed herein.

The present disclosure also provides a nucleic acid encoding a functional PABPN1 protein as described herein for use in therapy. For example, the nucleic acid encoding a functional PABPN1 protein may be for use in treating OPMD in a subject and/or in a method disclosed herein.

Treatment of OPMD in accordance with any example described herein may include one or more of reducing or inhibiting expression of a PABPN1 protein which is causative of OPMD i.e., a PABPN1 protein having an expanded polyalanine tract, in the subject. Alternatively, or additionally, treatment of OPMD in accordance with any example described herein may comprise replacement of PABPN1 protein in the subject using a nucleic acid encoding a functional PABPN1 protein as described herein. For example, the replacement PABPN1 protein may comprise the amino acid sequence of the wild-type PABPN1 protein. In one example, treatment will reduce or inhibit expression of a PABPN1 protein which is causative of OPMD and replace functional PABPN1 protein having the normal length of polyalanine residues in the subject.

KEY TO THE SEQUENCE LISTING

Figure 1:
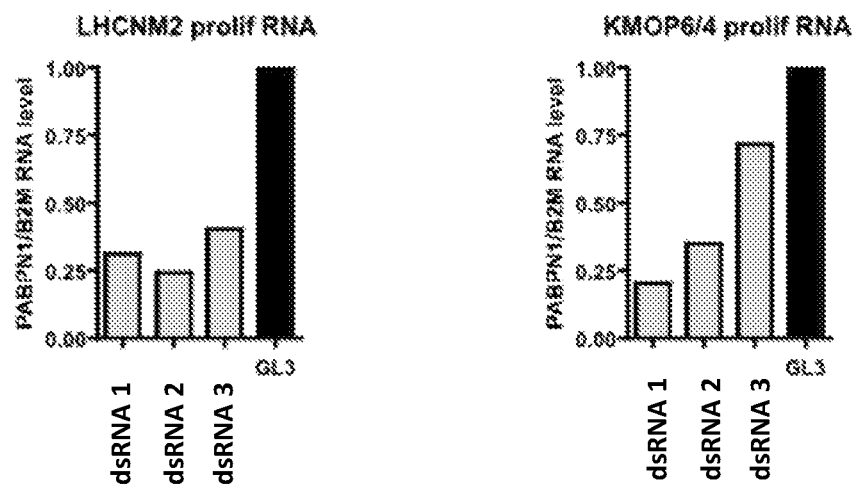
FIG. 1 shows the level of expression of human PABPN1 in healthy (LHCNM2) or OPMD affected (KMOP6/4) human myoblasts following transfection with candidate dsRNA sequences (dsRNA1, dsRNA2 and dsRNA3).

SEQ ID NO: 1: RNA sequence for region within mRNA transcript corresponding to PABPN1 protein designated PABPN1 mRNA Region 1.
SEQ ID NO: 2: RNA sequence for region within mRNA transcript corresponding to PABPN1 protein designated PABPN1 mRNA Region 2.
SEQ ID NO: 3: RNA sequence for region within mRNA transcript corresponding to PABPN1 protein designated PABPN1 mRNA Region 3.
SEQ ID NO: 4: RNA effector sequence for ssRNA and dsRNA designated ssRNA1 and dsRNA1, respectively.
SEQ ID NO: 5: RNA effector complement sequence for dsRNA designated dsRNA1.
SEQ ID NO: 6: RNA effector sequence for ssRNA and dsRNA designated ssRNA2 and dsRNA2, respectively.
SEQ ID NO: 7: RNA effector complement sequence for dsRNA designated dsRNA2.
SEQ ID NO: 8: RNA effector sequence for ssRNA and dsRNA designated ssRNA3 and dsRNA3, respectively.
SEQ ID NO: 9: RNA effector complement sequence for dsRNA designated dsRNA3.
SEQ ID NO: 10: RNA effector sequence for shRNAs designated shRNA1 and shRNA2.
SEQ ID NO: 11: RNA effector complement sequence for shRNAs designated shRNA1 and shRNA2.
SEQ ID NO: 12: RNA effector sequence for shRNAs designated shRNA3 and shRNA4.
SEQ ID NO: 13: RNA effector complement sequence for shRNAs designated shRNA3 and shRNA4.
SEQ ID NO: 14: RNA effector sequence for shRNAs designated shRNA5 and shRNA6.
SEQ ID NO: 15: RNA effector complement sequence for shRNAs designated shRNA5 and shRNA6.
SEQ ID NO: 16: RNA sequence for shRNA designated shRNA1.
SEQ ID NO: 17: RNA sequence for shRNA designated shRNA2.
SEQ ID NO: 18: RNA sequence for shRNA designated shRNA3.
SEQ ID NO: 19: RNA sequence for shRNA designated shRNA4.
SEQ ID NO: 20: RNA sequence for shRNA designated shRNA5.
SEQ ID NO: 21: RNA sequence for shRNA designated shRNA6.
SEQ ID NO: 22: DNA sequence for OPMD Triple construct short.
SEQ ID NO: 23: DNA sequence for OPMD Triple construct long.
SEQ ID NO: 24: DNA sequence for Human codon-optimized PABPN1 cDNA sequence.
SEQ ID NO: 25: Amino acid sequence for codon-optimised human PABPN1 protein.
SEQ ID NO: 26: DNA sequence for Human codon-optimized PABPN1 cDNA sequence (with Myc-tag).
SEQ ID NO: 27: Amino acid sequence for codon-optimised human PABPN1 protein (with Myc-tag).
SEQ ID NO: 28: cDNA sequence for mutant human PABPN1 protein (with FLAG-tag).
SEQ ID NO: 29: Amino acid sequence for mutant human PABPN1 protein (with FLAG tag).

DETAILED DESCRIPTION

General

Throughout this specification, unless specifically stated otherwise or the context requires otherwise, reference to a single step, feature, composition of matter, group of steps or group of features or compositions of matter shall be taken to encompass one and a plurality (i.e. one or more) of those steps, features, compositions of matter, groups of steps or groups of features or compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant DNA, recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

Throughout this specification, unless the context requires otherwise, the word "comprise", or variations such as "comprises" or "comprising", is understood to imply the inclusion of a stated step or element or integer or group of steps or elements or integers but not the exclusion of any other step or element or integer or group of elements or integers.

The term "and/or", e.g., "X and/or Y" shall be understood to mean either "X and Y" or "X or Y" and shall be taken to provide explicit support for both meanings or for either meaning.

Selected Definitions

By "RNA" is meant a molecule comprising at least one ribonucleotide residue. By "ribonucleotide" is meant a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly-produced RNA, as well as altered RNA that differs from naturally occurring RNA by the addition, deletion, substitution and/or alteration of one or more nucleotides. Such alterations can include addition of non-nucleotide material, such as to the end(s) of the RNA or internally, for example at one or more nucleotides of the RNA. Nucleotides in the RNA molecules of the instant disclosure can also comprise non-standard nucleotides, such as non-naturally occurring nucleotides or chemically synthesized nucleotides or deoxynucleotides. These altered RNAs can be referred to as analogs or analogs of naturally-occurring RNA.

As used herein, the term "RNAi reagent" refers to a RNA that is capable of eliciting "RNA interference" or "RNAi".

The term "RNA interference" or "RNAi" refers generally to RNA-dependent silencing of gene expression initiated by double stranded RNA (dsRNA) molecules and single-stranded short-interfering RNA (ss-siRNA) molecules in a cell's cytoplasm. The dsRNA molecule or ss-siRNA molecule reduces or inhibits transcription products of a target nucleic acid sequence, thereby silencing the gene.

As used herein, the term "double stranded RNA" or "dsRNA" refers to a RNA molecule having a duplex structure and comprising an effector sequence and an effector complement sequence which are of similar length to one another. The effector sequence and the effector complement sequence can be in a single RNA strand or in separate RNA strands. The "effector sequence" (often referred to as a "guide strand") is substantially complementary to a target sequence, which in the present case, is a region of a PABPN1 mRNA transcript. The "effector sequence" can also be referred to as the "antisense sequence". The "effector complement sequence" will be of sufficient complementary to the effector sequence such that it can anneal to the effector sequence to form a duplex. In this regard, the effector complement sequence will be substantially homologous to a region of target sequence. As will be apparent to the skilled person, the term "effector complement sequence" can also be referred to as the "complement of the effector sequence" or the sense sequence or the passenger strand sequence.

As used herein, the term "duplex" refers to regions in two complementary or substantially complementary nucleic acids (e.g., RNAs), or in two complementary or substantially complementary regions of a single-stranded nucleic acid (e.g., RNA), that form base pairs with one another, either by Watson-Crick base pairing or any other manner that allows for a stabilized duplex between the nucleotide sequences that are complementary or substantially complementary. It will be understood by the skilled person that within a duplex region, 100% complementarity is not required; substantial complementarity is allowable. Substantial complementarity may include 69% or greater complementarity. For example, a single mismatch in a duplex region consisting of 19 base pairs (i.e., 18 base pairs and one mismatch) results in 94.7% complementarity, rendering the duplex region substantially complementary. In another example, two mismatches in a duplex region consisting of 19 base pairs (i.e., 17 base pairs and two mismatches) results in 89.5% complementarity, rendering the duplex region substantially complementary. In yet another example, three mismatches in a duplex region consisting of 19 base pairs (i.e., 16 base pairs and three mismatches) results in 84.2% complementarity, rendering the duplex region substantially complementary, and so on.

The dsRNA may be provided as a hairpin or stem loop structure, with a duplex region comprised of an effector sequence and effector complement sequence linked by at least 2 nucleotide sequence which is termed a stem loop. When a dsRNA is provided as a hairpin or stem loop structure it can be referred to as a "hairpin RNA" or "short hairpin RNAi agent" or "shRNA". Other dsRNA molecules provided in, or which give rise to, a hairpin or stem loop structure include primary miRNA transcripts (pri-miRNA) and precursor microRNA (pre-miRNA). Pre-miRNA shRNAs can be naturally produced from pri-miRNA by the action of the enzymes Drosha and Pasha which recognize and release regions of the primary miRNA transcript which form a stem-loop structure. Alternatively, the pri-miRNA transcript can be engineered to replace the natural stem-loop structure with an artificial/recombinant stem-loop structure. In this case, Drosha and Pasha recognize and release the artificial shRNA. dsRNA molecules produced using this approach are known as "shmiRNAs", "shmiRs" or "microRNA framework shRNAs".

As used herein, the term "single-stranded short-interfering RNA", "ss-siRNA", "single-stranded RNA", "ssRNA" or similar refers to a RNA molecule having a single-stranded structure and comprising an effector sequence. As described herein for dsRNA molecules, the "effector sequence" (often referred to as an "antisense sequence" or "guide strand") is substantially complementary to a target sequence, which in the present case, is a region of a PABPN1 mRNA transcript.

However, unlike RNAi reagents having a duplex structure, ssRNAs do not comprise an effector complement sequence.

As used herein, the term "complementary" with regard to a sequence refers to a complement of the sequence by Watson-Crick base pairing, whereby guanine (G) pairs with cytosine (C), and adenine (A) pairs with either uracil (U) or thymine (T). A sequence may be complementary to the entire length of another sequence, or it may be complementary to a specified portion or length of another sequence. One of skill in the art will recognize that U may be present in RNA, and that T may be present in DNA. Therefore, an A within either of a RNA or DNA sequence may pair with a U in a RNA sequence or T in a DNA sequence.

As used herein, the term "substantially complementary" is used to indicate a sufficient degree of complementarity or precise pairing such that stable and specific binding occurs between nucleic acid sequences e.g., between the effector sequence and the effector complement sequence or between the effector sequence and the target sequence. It is understood that the sequence of a nucleic acid need not be 100% complementary to that of its target or complement. The term encompasses a sequence complementary to another sequence with the exception of an overhang. In some cases, the sequence is complementary to the other sequence with the exception of 1-2 mismatches. In some cases, the sequences are complementary except for 1 mismatch. In some cases, the sequences are complementary except for 2 mismatches. In other cases, the sequences are complementary except for 3 mismatches. In yet other cases, the sequences are complementary except for 4 mismatches.

The term "encoded" or "coding for", as used in the context of a RNA of the disclosure, shall be understood to mean a RNA is capable of being transcribed from a DNA template. Accordingly, a nucleic acid that encodes or codes for a RNA of the disclosure will comprise a DNA sequence which serves as a template for transcription of the respective RNA.

The term "DNA-directed RNAi construct" or "ddRNAi construct" refers to a nucleic acid comprising DNA sequence which, when transcribed produces a RNA molecule which elicits RNAi. The ddRNAi construct may comprise a nucleic acid which is transcribed as a single RNA that is capable of self-annealing into a hairpin structure with a duplex region linked by a stem loop of at least 2 nucleotides i.e., shRNA, or as a single RNA with multiple shRNAs or as multiple RNA transcripts each capable of folding as a single shRNA respectively. The ddRNAi construct may be within an expression vector i.e., "ddRNAi expression construct", e.g., operably-linked to a promoter.

As used herein, the term "operably-linked" or "operable linkage" (or similar) means that a coding nucleic acid sequence is linked to, or in association with, a regulatory sequence, e.g., a promoter, in a manner which facilitates expression of the coding sequence. Regulatory sequences include promoters, enhancers, and other expression control elements that are art-recognized and are selected to direct expression of the coding sequence.

A "vector" will be understood to mean a vehicle for introducing a nucleic acid into a cell. Vectors include, but are not limited to, plasmids, phagemids, viruses, bacteria, and vehicles derived from viral or bacterial sources. A "plasmid." is a circular, double-stranded DNA molecule. A useful type of vector for use in accordance with the present disclosure is a viral vector, wherein heterologous DNA sequences are inserted into a viral genome that can be modified to delete one or more viral genes or parts thereof. Certain vectors are capable of autonomous replication in a host cell (e.g., vectors having an origin of replication that functions in the host cell). Other vectors can be stably integrated into the genome of a host cell, and are thereby replicated along with the host genome. Other vectors persist in an extrachromosomal state without integrating into the genome of the host cell. As used herein, the term "expression vector" will be understood to mean a vector capable of expressing a RNA molecule of the disclosure.

A "functional PABPN1 protein" shall be understood to mean a PABPN1 protein having the functional properties of a wild-type PABPN1 protein e.g., an ability to control site of mRNA polyadenylation and/or intron splicing in a mammalian cell. Accordingly, a "functional PABPN1 protein" will be understood to be a PABPN1 protein which is not causative of OPMD when expressed or present in a subject. In one example, a reference herein to "functional PABPN1 protein" is a reference to human wild-type PABPN1 protein. The sequence of human wild-type PABPN1 protein is set forth in NCBI RefSeq NP_004634. Accordingly, a functional human PABPN1 protein may have the functional properties in vivo of the human PABPN1 protein set forth in NCBI RefSeq NP_004634.

As used herein, the terms "treating", "treat" or "treatment" and variations thereof, refer to clinical intervention designed to alter the natural course of the individual or cell being treated during the course of clinical pathology. Desirable effects of treatment include decreasing the rate of disease progression, ameliorating or palliating the disease state, and remission or improved prognosis. It follows that treatment of OPMD includes reducing or inhibiting expression of a PABPN1 protein which is causative of OPMD in the subject and/or expressing in the subject a PABPN1 protein having the normal length of polyalanine residues. Preferably, treatment of OPMD includes reducing or inhibiting expression of the PABPN1 protein which is causative of OPMD in the subject and expressing in the subject a PABPN1 protein having the normal length of polyalanine residues. An individual is successfully "treated", for example, if one or more of the above treatment outcomes is achieved.

A "therapeutically effective amount" is at least the minimum concentration or amount required to effect a measurable improvement in the OPMD condition, such as a measurable improvement in in one or more symptoms of OPMD e.g., including but not limited to ptosis, dysphagia and muscle weakness in the subject. A therapeutically effective amount herein may vary according to factors such as the disease state, age, sex, and weight of the patient, and the ability of the RNA, ddRNAi or expression construct to elicit a desired response in the individual and/or the ability of the expression vector to express functional PABPN1 protein in the subject. A therapeutically effective amount is also one in which any toxic or detrimental effects of the RNA, ddRNAi construct or expression vector are outweighed by the therapeutically beneficial effects of the RNA, ddRNAi construct or expression vector to inhibit, suppress or reduce expression of PABPN1 protein causative of OPMD considered alone or in combination with the therapeutically beneficial effects of the expression of functional PABPN1 protein in the subject.

As used herein, the "subject" or "patient" can be a human or non-human animal suffering from or genetically predisposed to OPMD i.e., possess a PABPN1 gene variant which is causative of OPMD. The "non-human animal" may be a primate, livestock (e.g. sheep, horses, cattle, pigs, donkeys), companion animal (e.g. pets such as dogs and cats), laboratory test animal (e.g. mice, rabbits, rats, guinea pigs, drosophila, *C. elegans*, zebrafish), performance animal (e.g. racehorses, camels, greyhounds) or captive wild animal. In one example, the subject or patient is a mammal. In one example, the subject or patient is a human.

The terms "reduced expression", "reduction in expression" or similar, refer to the absence or an observable decrease in the level of protein and/or mRNA product from the target gene e.g., the PABPN1 gene. The decrease does not have to be absolute, but may be a partial decrease sufficient for there to a detectable or observable change as a result of the RNAi effected by the RNA of the disclosure. The decrease can be measured by determining a decrease in the level of mRNA and/or protein product from a target nucleic acid relative to a cell lacking the RNA, ddRNAi construct or expression vector, and may be as little as 1%, 5% or 10%, or may be absolute i.e., 100% inhibition. The effects of the decrease may be determined by examination of the outward properties i.e., quantitative and/or qualitative phenotype of the cell or organism, and may also include detection of the presence or a change in the amount of nuclear aggregates of expPABPN1 in the cell or organism following administration of a RNA, ddRNAi construct or expression vector of the disclosure.

Agents for RNAi

In one example, the present disclosure provides a RNA, i.e., capable of eliciting RNAi, wherein the RNA comprises an effector sequence of at least 17 contiguous nucleotides which is substantially complementary to a region of a RNA transcript corresponding to a PABPN1 protein, wherein the region of the RNA transcript is set forth in any one of SEQ ID NOs: 1-3. Preferably, the RNA of the disclosure will comprise an effector sequence which is less than 30 nucleotides in length. For example, suitable effector sequences may be in the range of 17-29 nucleotides in length.

In one example, the effector sequence is substantially complementary to a region of a RNA transcript corresponding to a PABPN1 protein, wherein the region of the RNA transcript is set forth in SEQ ID NO: 1. For example, the effector sequence may be substantially complementary to a sequence set forth in SEQ ID NO: 1 and contain 6 mismatch bases relative thereto. For example, the effector sequence may be substantially complementary to a sequence set forth in SEQ ID NO: 1 and contain 5 mismatch bases relative thereto. For example, the effector sequence may be substantially complementary to a sequence set forth in SEQ ID NO: 1 and contain 4 mismatch bases relative thereto. For example, the effector sequence may be substantially complementary to a sequence set forth in SEQ ID NO: 1 and contain 3 mismatch bases relative thereto. For example, the effector sequence may be substantially complementary to a sequence set forth in SEQ ID NO: 1 and contain 2 mismatch bases relative thereto. For example, the effector sequence may be substantially complementary to a sequence set forth in SEQ ID NO: 1 and contain 1 mismatch base relative thereto. For example, the effector sequence may be 100% complementary to a sequence set forth in SEQ ID NO: 1.

In one example, the effector sequence is substantially complementary to a region of a RNA transcript corresponding to a PABPN1 protein, wherein the region of the RNA transcript is set forth in SEQ ID NO: 2. For example, the effector sequence may be substantially complementary to a sequence set forth in SEQ ID NO: 2 and contain 6 mismatch bases relative thereto. For example, the effector sequence may be substantially complementary to a sequence set forth in SEQ ID NO: 2 and contain 5 mismatch bases relative thereto. For example, the effector sequence may be substantially complementary to a sequence set forth in SEQ ID NO: 2 and contain 4 mismatch bases relative thereto. For example, the effector sequence may be substantially complementary to a sequence set forth in SEQ ID NO: 2 and contain 3 mismatch bases relative thereto. For example, the effector sequence may be substantially complementary to a sequence set forth in SEQ ID NO: 2 and contain 2 mismatch bases relative thereto. For example, the effector sequence may be substantially complementary to a sequence set forth in SEQ ID NO: 2 and contain 1 mismatch base relative thereto. For example, the effector sequence may be 100% complementary to a sequence set forth in SEQ ID NO: 2.

In one example, the effector sequence is substantially complementary to a region of a RNA transcript corresponding to a PABPN1 protein, wherein the region of the RNA transcript is set forth in SEQ ID NO: 3. For example, the effector sequence may be substantially complementary to a sequence set forth in SEQ ID NO: 3 and contain 6 mismatch bases relative thereto. For example, the effector sequence may be substantially complementary to a sequence set forth in SEQ ID NO: 3 and contain 5 mismatch bases relative thereto. For example, the effector sequence may be substantially complementary to a sequence set forth in SEQ ID NO: 3 and contain 4 mismatch bases relative thereto. For example, the effector sequence may be substantially complementary to a sequence set forth in SEQ ID NO: 3 and contain 3 mismatch bases relative thereto. For example, the effector sequence may be substantially complementary to a sequence set forth in SEQ ID NO: 3 and contain 2 mismatch bases relative thereto. For example, the effector sequence may be substantially complementary to a sequence set forth in SEQ ID NO: 3 and contain 1 mismatch base relative thereto. For example, the effector sequence may be 100% complementary to a sequence set forth in SEQ ID NO: 3.

In one example, the RNA of the disclosure is a single-stranded RNA (ssRNA).

A ssRNA in accordance with the present disclosure may comprise an effector sequence of at least 17 contiguous nucleotides which is substantially complementary to a region of a RNA transcript corresponding to a PABPN1 protein, wherein the region of the RNA transcript is set forth in any one of SEQ ID NOs: 1-3. For example, a ssRNA of the disclosure may comprise an effector sequence comprising or consisting of a sequence which is substantially identical to a sequence set forth in SEQ ID NO: 4, 6 or 8.

In one example, a ssRNA of the disclosure may comprise an effector sequence comprising or consisting of a sequence which is substantially identical to a sequence set forth in SEQ ID NO: 4. For example, the effector sequence may be substantially identical to a sequence set forth in SEQ ID NO: 4 and contain 6 bases which vary relative thereto. For example, the effector sequence may be substantially identical to a sequence set forth in SEQ ID NO: 4 and contain 5 bases which vary relative thereto. For example, the effector sequence may be substantially identical to a sequence set forth in SEQ ID NO: 4 and contain 4 bases which vary relative thereto. For example, the effector sequence may be substantially identical to a sequence set forth in SEQ ID NO: 4 and contain 3 bases which vary relative thereto. For example, the effector sequence may be substantially identical to a sequence set forth in SEQ ID NO: 4 and contain 2 bases which vary relative thereto. For example, the effector sequence may be substantially identical to a sequence set forth in SEQ ID NO: 4 and contain 1 base which varies relative thereto. For example, the effector sequence may be 100% identical to the sequence set forth in SEQ ID NO: 4

In one example, a ssRNA of the disclosure may comprise an effector sequence comprising or consisting of a sequence which is substantially identical to a sequence set forth in SEQ ID NO: 6. For example, the effector sequence may be substantially identical to a sequence set forth in SEQ ID NO: 6 and contain 6 bases which vary relative thereto. For example, the effector sequence may be substantially identical to a sequence set forth in SEQ ID NO: 6 and contain 5 bases which vary relative thereto. For example, the effector sequence may be substantially identical to a sequence set forth in SEQ ID NO: 6 and contain 4 bases which vary relative thereto. For example, the effector sequence may be substantially identical to a sequence set forth in SEQ ID NO: 6 and contain 3 bases which vary relative thereto. For example, the effector sequence may be substantially identical to a sequence set forth in SEQ ID NO: 6 and contain 2 bases which vary relative thereto. For example, the effector sequence may be substantially identical to a sequence set forth in SEQ ID NO: 6 and contain 1 base which varies relative thereto. For example, the effector sequence may be 100% identical to the sequence set forth in SEQ ID NO: 6

In one example, a ssRNA of the disclosure may comprise an effector sequence comprising or consisting of a sequence which is substantially identical to a sequence set forth in SEQ ID NO: 8. For example, the effector sequence may be substantially identical to a sequence set forth in SEQ ID NO: 8 and contain 6 bases which vary relative thereto. For example, the effector sequence may be substantially identical to a sequence set forth in SEQ ID NO: 8 and contain 5 bases which vary relative thereto. For example, the effector sequence may be substantially identical to a sequence set forth in SEQ ID NO: 8 and contain 4 bases which vary relative thereto. For example, the effector sequence may be substantially identical to a sequence set forth in SEQ ID NO: 8 and contain 3 bases which vary relative thereto. For example, the effector sequence may be substantially identical to a sequence set forth in SEQ ID NO: 8 and contain 2 bases which vary relative thereto. For example, the effector sequence may be substantially identical to a sequence set forth in SEQ ID NO: 8 and contain 1 base which varies relative thereto. For example, the effector sequence may be 100% identical to the sequence set forth in SEQ ID NO: 8

In one example, the RNA of the disclosure which is capable of eliciting RNAi is a double-stranded RNA (dsRNA). A dsRNA in accordance with the present disclosure will comprise an effector sequence and an effector complement sequence, wherein the effector sequence comprises at least 17 contiguous nucleotides which is substantially complementary to a region of a RNA transcript corresponding to a PABPN1 protein, wherein the region of the RNA transcript is set forth in any one of SEQ ID NOs: 1-3.

Exemplary dsRNAs in accordance with the present disclosure comprise an effector sequence which is substantially complementary to an effector complement sequence described in the column labelled "Effector complement" in Table 3 i.e., SEQ ID NOs: 5, 7 and 9.

In one example, the present disclosure provides a dsRNA comprising an effector sequence which is substantially complementary to the sequence set forth in SEQ ID NO: 5. For example, the effector sequence may be substantially complementary to a sequence set forth in SEQ ID NO: 5, with the exception of 6 base mismatches. For example, the effector sequence may be substantially complementary to a sequence set forth in SEQ ID NO: 5, with the exception of 5 base mismatches. For example, the effector sequence may be substantially complementary to a sequence set forth in SEQ ID NO: 5, with the exception of 4 base mismatches. For example, the effector sequence may be substantially complementary to a sequence set forth in SEQ ID NO: 5, with the exception of 3 base mismatches. For example, the effector sequence may be substantially complementary to a sequence set forth in SEQ ID NO: 5, with the exception of 2 base mismatches. For example, the effector sequence may be substantially complementary to a sequence set forth in SEQ ID NO: 5, with the exception of a single base mismatch. For example, the effector sequence may be 100% complementary to a sequence set forth in SEQ ID NO: 5.

In one example, the present disclosure provides a dsRNA comprising an effector sequence which is substantially complementary to the sequence set forth in SEQ ID NO: 7. For example, the effector sequence may be substantially complementary to a sequence set forth in SEQ ID NO: 7, with the exception of 6 base mismatches. For example, the effector sequence may be substantially complementary to a sequence set forth in SEQ ID NO: 7, with the exception of 5 base mismatches. For example, the effector sequence may be substantially complementary to a sequence set forth in SEQ ID NO: 7, with the exception of 4 base mismatches. For example, the effector sequence may be substantially complementary to a sequence set forth in SEQ ID NO: 7, with the exception of 3 base mismatches. For example, the effector sequence may be substantially complementary to a sequence set forth in SEQ ID NO: 7, with the exception of 2 base mismatches. For example, the effector sequence may be substantially complementary to a sequence set forth in SEQ ID NO: 7, with the exception of a single base mismatch. For example, the effector sequence may be 100% complementary to a sequence set forth in SEQ ID NO: 7.

In one example, the present disclosure provides a dsRNA comprising an effector sequence which is substantially complementary to the sequence set forth in SEQ ID NO: 9. For example, the effector sequence may be substantially complementary to a sequence set forth in SEQ ID NO: 9, with the exception of 6 base mismatches. For example, the effector sequence may be substantially complementary to a sequence set forth in SEQ ID NO: 9, with the exception of 5 base mismatches. For example, the effector sequence may be substantially complementary to a sequence set forth in SEQ ID NO: 9, with the exception of 4 base mismatches. For example, the effector sequence may be substantially complementary to a sequence set forth in SEQ ID NO: 9, with the exception of 3 base mismatches. For example, the effector sequence may be substantially complementary to a sequence set forth in SEQ ID NO: 9, with the exception of 2 base mismatches. For example, the effector sequence may be substantially complementary to a sequence set forth in SEQ ID NO: 9, with the exception of a single base mismatch. For example, the effector sequence may be 100% complementary to a sequence set forth in SEQ ID NO: 9.

Where a dsRNA of the disclosure comprises an effector sequence which is substantially complementary to a sequence described in the column labelled "Effector complement" in Table 3 with the exception of 1, 2, 3, 4, 5 or 6 mismatches (as described herein), the effector sequence will still be able to form a duplex with the corresponding effector complement sequence in Table 3.

In one example, the present disclosure provides a dsRNA comprising an effector sequence and an effector complement sequence, wherein the effector sequence is a sequence described in the column labelled "Effector" in Table 3 i.e., selected from SEQ ID NOs: 4, 6 and 8, and the effector complement sequence of the dsRNA is substantially complementary to the effector sequence thereof. For example, the effector complement sequence of the RNA may comprise 1, 2, 3, 4, 5 or 6 mismatches relative to the cognate effector sequence, but still be capable of forming a duplex therewith.

In one example, the dsRNA may comprise an effector sequence set forth in SEQ ID NO: 4 and an effector complement sequence which is substantially complementary thereto with the exception of 1, 2, 3, 4, 5 or 6 base mismatches. For example, the effector complement sequence may be substantially complementary to a sequence set forth in SEQ ID NO: 4, with the exception of 6 base mismatches. For example, the effector complement sequence may be substantially complementary to a sequence set forth in SEQ ID NO: 4, with the exception of 5 base mismatches. For example, the effector complement sequence may be substantially complementary to a sequence set forth in SEQ ID NO: 4, with the exception of 4 base mismatches. For example, the effector complement sequence may be substantially complementary to a sequence set forth in SEQ ID NO: 4, with the exception of 3 base mismatches. For example, the effector complement sequence may be substantially complementary to a sequence set forth in SEQ ID NO: 4, with the exception of 2 base mismatches. For example, the effector complement sequence may be substantially complementary to a sequence set forth in SEQ ID NO: 4, with the exception of a single base mismatch For example, the effector complement sequence may be 100% complementary to a sequence set forth in SEQ ID NO: 4.

In one example, the dsRNA may comprise an effector sequence set forth in SEQ ID NO: 6 and an effector complement sequence which is substantially complementary thereto with the exception of 1, 2, 3, 4, 5 or 6 base mismatches. For example, the effector complement sequence may be substantially complementary to a sequence set forth in SEQ ID NO: 6, with the exception of 6 base mismatches. For example, the effector complement sequence may be substantially complementary to a sequence set forth in SEQ ID NO: 6, with the exception of 5 base mismatches. For example, the effector complement sequence may be substantially complementary to a sequence set forth in SEQ ID NO: 6, with the exception of 4 base mismatches. For example, the effector complement sequence may be substantially complementary to a sequence set forth in SEQ ID NO: 6, with the exception of 3 base mismatches. For example, the effector complement sequence may be substantially complementary to a sequence set forth in SEQ ID NO: 6, with the exception of 2 base mismatches. For example, the effector complement sequence may be substantially complementary to a sequence set forth in SEQ ID NO: 6, with the exception of a single base mismatch For example, the effector complement sequence may be 100% complementary to a sequence set forth in SEQ ID NO: 6.

In one example, the dsRNA may comprise an effector sequence set forth in SEQ ID NO: 8 and an effector complement sequence which is substantially complementary thereto with the exception of 1, 2, 3, 4, 5 or 6 base mismatches. For example, the effector complement sequence may be substantially complementary to a sequence set forth in SEQ ID NO: 8, with the exception of 6 base mismatches. For example, the effector complement sequence may be substantially complementary to a sequence set forth in SEQ ID NO: 8, with the exception of 5 base mismatches. For example, the effector complement sequence may be substantially complementary to a sequence set forth in SEQ ID NO: 8, with the exception of 4 base mismatches. For example, the effector complement sequence may be substantially complementary to a sequence set forth in SEQ ID NO: 8, with the exception of 3 base mismatches. For example, the effector complement sequence may be substantially complementary to a sequence set forth in SEQ ID NO: 8, with the exception of 2 base mismatches. For example, the effector complement sequence may be substantially complementary to a sequence set forth in SEQ ID NO: 8, with the exception of a single base mismatch For example, the effector complement sequence may be 100% complementary to a sequence set forth in SEQ ID NO: 8.

Exemplary dsRNAs in accordance with the present disclosure comprise corresponding effector and effector complement sequences as described in the columns of Table 3 labelled "Effector" and "Effector complement", respectively. In one example, the corresponding effector and effector complement sequences of the dsRNA may be provided as separate nucleic acids which are duplexed e.g., by Watson-Crick base pairing.

An exemplary RNA of the disclosure which is a dsRNA comprises an effector sequence consisting of the sequence set forth in SEQ ID NO: 4 and an effector complement sequence consisting of the sequence set forth in SEQ ID NO: 5.

An exemplary RNA of the disclosure which is a dsRNA comprises an effector sequence consisting of the sequence set forth in SEQ ID NO: 6 and an effector complement sequence consisting of the sequence set forth in SEQ ID NO: 7.

An exemplary RNA of the disclosure which is a dsRNA comprises an effector sequence consisting of the sequence set forth in SEQ ID NO: 8 and an effector complement sequence consisting of the sequence set forth in SEQ ID NO: 9.

A RNA of the disclosure which is capable of eliciting RNAi may also be provided as a short hairpin RNA (shRNA). A shRNA in accordance with this example of the disclosure will comprise an effector sequence and an effector complement sequence, wherein the effector sequence comprises at least 17 contiguous nucleotides which is substantially complementary to a region of a RNA transcript corresponding to a PABPN1 protein, wherein the region of the RNA transcript is set forth in any one of SEQ ID NOs: 1-3.

An exemplary shRNA in accordance with the present disclosure comprises an effector sequence and an effector complement sequence, wherein the effector sequence is substantially complementary to an effector complement sequence described in the column labelled "Effector complement" in Table 4 i.e., SEQ ID NOs: 11, 13 and 15.

In one example, the present disclosure provides a shRNA comprising an effector sequence which is substantially complementary to the sequence set forth in SEQ ID NO: 11. For example, the effector sequence may be substantially complementary to a sequence set forth in SEQ ID NO: 11, with the exception of 6 base mismatches. For example, the effector sequence may be substantially complementary to a sequence set forth in SEQ ID NO: 11, with the exception of 5 base mismatches. For example, the effector sequence may be substantially complementary to a sequence set forth in SEQ ID NO: 11, with the exception of 4 base mismatches. For example, the effector sequence may be substantially complementary to a sequence set forth in SEQ ID NO: 11, with the exception of 3 base mismatches. For example, the effector sequence may be substantially complementary to a sequence set forth in SEQ ID NO: 11, with the exception of 2 base mismatches. For example, the effector sequence may be substantially complementary to a sequence set forth in SEQ ID NO: 11, with the exception of a single base mismatch. For example, the effector sequence may be 100% complementary to a sequence set forth in SEQ ID NO: 11.

In one example, the present disclosure provides a shRNA comprising an effector sequence which is substantially complementary to the sequence set forth in SEQ ID NO: 13. For example, the effector sequence may be substantially complementary to a sequence set forth in SEQ ID NO: 13, with the exception of 6 base mismatches. For example, the effector sequence may be substantially complementary to a sequence set forth in SEQ ID NO: 13, with the exception of 5 base mismatches. For example, the effector sequence may be substantially complementary to a sequence set forth in SEQ ID NO: 13, with the exception of 4 base mismatches. For example, the effector sequence may be substantially complementary to a sequence set forth in SEQ ID NO: 13, with the exception of 3 base mismatches. For example, the effector sequence may be substantially complementary to a sequence set forth in SEQ ID NO: 13, with the exception of 2 base mismatches. For example, the effector sequence may be substantially complementary to a sequence set forth in SEQ ID NO: 13, with the exception of a single base mismatch. For example, the effector sequence may be 100% complementary to a sequence set forth in SEQ ID NO: 13.

In one example, the present disclosure provides a shRNA comprising an effector sequence which is substantially complementary to the sequence set forth in SEQ ID NO: 15. For example, the effector sequence may be substantially complementary to a sequence set forth in SEQ ID NO: 15, with the exception of 6 base mismatches. For example, the effector sequence may be substantially complementary to a sequence set forth in SEQ ID NO: 15, with the exception of 5 base mismatches. For example, the effector sequence may be substantially complementary to a sequence set forth in SEQ ID NO: 15, with the exception of 4 base mismatches. For example, the effector sequence may be substantially complementary to a sequence set forth in SEQ ID NO: 15, with the exception of 3 base mismatches. For example, the effector sequence may be substantially complementary to a sequence set forth in SEQ ID NO: 15, with the exception of 2 base mismatches. For example, the effector sequence may be substantially complementary to a sequence set forth in SEQ ID NO: 15, with the exception of a single base mismatch. For example, the effector sequence may be 100% complementary to a sequence set forth in SEQ ID NO: 15.

Where a shRNA of the disclosure comprises an effector sequence which is substantially complementary to a sequence described in the column labelled "Effector complement" in Table 4 with the exception of 1, 2, 3, 4, 5 or 6 mismatches (as described herein), the effector sequence will still be able to form a duplex region with the corresponding effector complement sequence in Table 4.

In another example, the present disclosure provides a shRNA comprising an effector sequence and an effector complement sequence, wherein the effector sequence is a sequence described in the column labelled "Effector" in Table 4 i.e., selected from SEQ ID NOs: 10, 12 and 14, and the effector complement sequence of the shRNA is substantially complementary to the effector sequence thereof. For example, the effector complement sequence of the shRNA may comprise 1, 2, 3, 4, 5 or 6 mismatches relative to the cognate effector sequence, but still be capable of forming a duplex therewith.

In one example, the shRNA may comprise an effector sequence set forth in SEQ ID NO: 10 and an effector complement sequence which is substantially complementary thereto with the exception of 1, 2, 3, 4, 5 or 6 base mismatches. For example, the effector complement sequence may be substantially complementary to a sequence set forth in SEQ ID NO: 10, with the exception of 6 base mismatches. For example, the effector complement sequence may be substantially complementary to a sequence set forth in SEQ ID NO: 10, with the exception of 5 base mismatches. For example, the effector complement sequence may be substantially complementary to a sequence set forth in SEQ ID NO: 10, with the exception of 4 base mismatches. For example, the effector complement sequence may be substantially complementary to a sequence set forth in SEQ ID NO: 10, with the exception of 3 base mismatches. For example, the effector complement sequence may be substantially complementary to a sequence set forth in SEQ ID NO: 10, with the exception of 2 base mismatches. For example, the effector complement sequence may be substantially complementary to a sequence set forth in SEQ ID NO: 10, with the exception of a single base mismatch For example, the effector complement sequence may be 100% complementary to a sequence set forth in SEQ ID NO: 10.

In one example, the shRNA may comprise an effector sequence set forth in SEQ ID NO: 12 and an effector complement sequence which is substantially complementary thereto with the exception of 1, 2, 3, 4, 5 or 6 base mismatches. For example, the effector complement sequence may be substantially complementary to a sequence set forth in SEQ ID NO: 12, with the exception of 6 base mismatches. For example, the effector complement sequence may be substantially complementary to a sequence set forth in SEQ ID NO: 12, with the exception of 5 base mismatches. For example, the effector complement sequence may be substantially complementary to a sequence set forth in SEQ ID NO: 12, with the exception of 4 base mismatches. For example, the effector complement sequence may be substantially complementary to a sequence set forth in SEQ ID NO: 12, with the exception of 3 base mismatches. For example, the effector complement sequence may be substantially complementary to a sequence set forth in SEQ ID NO: 12, with the exception of 2 base mismatches. For example, the effector complement sequence may be substantially complementary to a sequence set forth in SEQ ID NO: 12, with the exception of a single base mismatch For example, the effector complement sequence may be 100% complementary to a sequence set forth in SEQ ID NO: 12.

In one example, the shRNA may comprise an effector sequence set forth in SEQ ID NO: 14 and an effector complement sequence which is substantially complementary thereto with the exception of 1, 2, 3, 4, 5 or 6 base mismatches. For example, the effector complement sequence may be substantially complementary to a sequence set forth in SEQ ID NO: 14, with the exception of 6 base mismatches. For example, the effector complement sequence may be substantially complementary to a sequence set forth in SEQ ID NO: 14, with the exception of 5 base mismatches. For example, the effector complement sequence may be substantially complementary to a sequence set forth in SEQ ID NO: 14, with the exception of 4 base mismatches. For example, the effector complement sequence may be substantially complementary to a sequence set forth in SEQ ID NO: 14, with the exception of 3 base mismatches. For example, the effector complement sequence may be substantially complementary to a sequence set forth in SEQ ID NO: 14, with the exception of 2 base mismatches. For example, the effector complement sequence may be substantially complementary to a sequence set forth in SEQ ID NO: 14, with the exception of a single base mismatch For example, the effector complement sequence may be 100% complementary to a sequence set forth in SEQ ID NO: 14.

Where a RNA of the disclosure is provided as a shRNA, a stem loop sequence will be positioned between the corresponding effector sequence and effector complement sequence such that the respective RNA forms a single contiguous sequence. A stem loop sequence is of sufficient length to permit the effector sequence and the effector complement sequence to anneal to one another i.e., form a duplex region by Watson-Crick base pairing. Suitable stem loop sequences may for instance be selected from those known in the art.

Exemplary shRNAs in accordance with the present disclosure comprise corresponding effector and effector complement sequences as described in the columns of Table 4 labelled "Effector" and "Effector complement", respectively. Such exemplary shRNAs may comprise a sequence set forth in Table 5, optionally modified as described herein.

An exemplary RNA of the disclosure which is a shRNA comprises an effector sequence consisting of the sequence set forth in SEQ ID NO: 10 and an effector complement sequence consisting of the sequence set forth in SEQ ID NO: 11. A shRNA in accordance with this example may comprise or consist of the sequence set forth in SEQ ID NO: 16. Alternatively, a shRNA in accordance with this example may comprise or consist of the sequence set forth in SEQ ID NO: 17.

An exemplary RNA of the disclosure which is a shRNA comprises an effector sequence consisting of the sequence set forth in SEQ ID NO: 12 and an effector complement sequence consisting of the sequence set forth in SEQ ID NO: 13. A shRNA in accordance with this example may comprise or consist of the sequence set forth in SEQ ID NO: 18. Alternatively, a shRNA in accordance with this example may comprise or consist of the sequence set forth in SEQ ID NO: 19.

An exemplary RNA of the disclosure which is a shRNA comprises an effector sequence consisting of the sequence set forth in SEQ ID NO: 14 and an effector complement sequence consisting of the sequence set forth in SEQ ID NO: 15. A shRNA in accordance with this example may comprise or consist of the sequence set forth in SEQ ID NO: 20. Alternatively, a shRNA in accordance with this example may comprise or consist of the sequence set forth in SEQ ID NO: 21.

Each of the shRNAs described herein may optionally further comprise two contiguous uracils (UU) at the 3' end of the shRNA e.g., as a consequence of transcriptional termination from a RNA Pol III promoter.

The present disclosure also provides a plurality of RNAs i.e., capable of eliciting RNAi, wherein each of the RNAs comprises an effector sequence of at least 17 contiguous nucleotides which is substantially complementary to a region of a RNA transcript corresponding to a PABPN1 protein which is causative of OPMD, and at least one RNA of the plurality is a RNA comprising an effector sequence which is substantially complementary to a sequence set forth in any one of SEQ ID NOs: 1-3 as described herein. Preferably, each RNA of the plurality comprises an effector sequence which is less than 30 nucleotides in length. For example, suitable effector sequences may be in the range of 17-29 nucleotides in length.

Exemplary RNAs, including ssRNAs, dsRNAs and shRNAs, comprising an effector sequence which is substantially complementary to a sequence set forth in any one of SEQ ID NOs: 1-3 have been described and shall be taken to apply mutatis mutandis to this example of the disclosure.

A plurality of RNAs in accordance with the present disclosure may comprise two RNAs as described herein. In another example, a plurality of RNAs in accordance with the present disclosure may comprise three of the RNAs described herein.

Thus, the plurality of RNAs in accordance with the present disclosure may comprise one or more of the RNAs described herein comprising an effector sequence having at least 17 contiguous nucleotides which is substantially complementary to a region of a RNA transcript corresponding to a PABPN1 protein which is causative of OPMD as set forth in Table 1.

In one example, the effector sequence of at least one RNA in the plurality is substantially complementary to a sequence set forth in SEQ ID NO: 1.

In one example, the effector sequence of at least one RNA in the plurality is substantially complementary to a sequence set forth in SEQ ID NO: 2.

In one example, the effector sequence of at least one RNA in the plurality is substantially complementary to a sequence set forth in SEQ ID NO: 3.

In one example, the effector sequence of at least one RNA in the plurality is substantially complementary to a sequence set forth in SEQ ID NO: 1 and the effector sequence of another RNA in the plurality is substantially complementary to a sequence set forth in SEQ ID NO: 2.

In one example, the effector sequence of at least one RNA in the plurality is substantially complementary to a sequence set forth in SEQ ID NO: 1 and the effector sequence of another RNA in the plurality is substantially complementary to a sequence set forth in SEQ ID NO: 3.

In one example, the effector sequence of at least one RNA in the plurality is substantially complementary to a sequence set forth in SEQ ID NO: 2 and the effector sequence of another RNA in the plurality is substantially complementary to a sequence set forth in SEQ ID NO: 3.

In one example, the effector sequence of at least one RNA in the plurality is substantially complementary to a sequence set forth in SEQ ID NO: 1 and the effector sequence of another RNA in the plurality is substantially complementary to a sequence set forth in SEQ ID NO: 2 and the effector sequence of yet another RNA in the plurality is substantially complementary to a sequence set forth in SEQ ID NO: 3.

Exemplary RNAs, including ssRNAs, dsRNAs, shRNAs and shmiRNAs, which comprise an effector sequence of at least 17 contiguous nucleotides which is substantially complementary to a sequence set forth in one of SEQ ID NOs: 1-3 are described herein.

In one example, the disclosure provides a plurality of RNAs which are ssRNAs, each comprising an effector sequence which is substantially identical to an effector sequence set forth in the column labelled "Effector sequence" in Table 2.

An exemplary plurality of ssRNAs of the disclosure comprises:

(i) a ssRNA comprising an effector sequence comprising or consisting of the sequence set forth in SEQ ID NO: 4; and (ii) a ssRNA comprising an effector sequence comprising or consisting of the sequence set forth in SEQ ID NO: 6.

An exemplary plurality of ssRNAs of the disclosure comprises:

(i) a ssRNA comprising an effector sequence comprising or consisting of the sequence set forth in SEQ ID NO: 4; and (ii) a ssRNA comprising an effector sequence comprising or consisting of the sequence set forth in SEQ ID NO: 8.

An exemplary plurality of ssRNAs of the disclosure comprises:
(i) a ssRNA comprising an effector sequence comprising or consisting of the sequence set forth in SEQ ID NO: 6; and
(ii) a ssRNA comprising an effector sequence comprising or consisting of the sequence set forth in SEQ ID NO: 8.

An exemplary plurality of ssRNAs of the disclosure comprises:
(i) a ssRNA comprising an effector sequence comprising or consisting of the sequence set forth in SEQ ID NO: 4;
(ii) a ssRNA comprising an effector sequence comprising or consisting of the sequence set forth in SEQ ID NO: 6; and
(iii) a ssRNA comprising an effector sequence comprising or consisting of the sequence set forth in SEQ ID NO: 8.

In one example, the disclosure provides a plurality of RNAs which are dsRNAs, each comprising an effector sequence and an effector complement sequence, wherein the effector sequence of each RNA is substantially complementary to an effector complement sequence set forth in the column labelled "Effector complement" in Table 3. For example, the effector sequence of each dsRNA may comprise or consists of a sequence set forth in the column labelled "Effector" in Table 3. The cognate effector complement sequence may comprise or consist of a sequence set forth in the column labelled "Effector complement" in Table 3.

Exemplary dsRNAs comprising an effector sequence which is substantially complementary to an effector complement sequence set forth in the column labelled "Effector complement" in Table 3 are described herein.

An exemplary plurality of RNAs of the disclosure comprises:
(i) a dsRNA comprising an effector sequence comprising or consisting of the sequence set forth in SEQ ID NO: 4 and an effector complement sequence comprising or consisting of the sequence set forth in SEQ ID NO: 5; and
(ii) a dsRNA comprising an effector sequence comprising or consisting of the sequence set forth in SEQ ID NO: 6 and an effector complement sequence comprising or consisting of the sequence set forth in SEQ ID NO: 7.

An exemplary plurality of RNAs of the disclosure comprises:
(i) a dsRNA comprising an effector sequence comprising or consisting of the sequence set forth in SEQ ID NO: 4 and an effector complement sequence comprising or consisting of the sequence set forth in SEQ ID NO: 5; and
(ii) a dsRNA comprising an effector sequence comprising or consisting of the sequence set forth in SEQ ID NO: 8 and an effector complement sequence comprising or consisting of the sequence set forth in SEQ ID NO: 9.

An exemplary plurality of RNAs of the disclosure comprises:
(i) a dsRNA comprising an effector sequence comprising or consisting of the sequence set forth in SEQ ID NO: 6 and an effector complement sequence comprising or consisting of the sequence set forth in SEQ ID NO: 7; and
(ii) a dsRNA comprising an effector sequence comprising or consisting of the sequence set forth in SEQ ID NO: 8 and an effector complement sequence comprising or consisting of the sequence set forth in SEQ ID NO: 9.

An exemplary plurality of RNAs of the disclosure comprises:
(i) a dsRNA comprising an effector sequence comprising or consisting of the sequence set forth in SEQ ID NO: 4 and an effector complement sequence comprising or consisting of the sequence set forth in SEQ ID NO: 5;
(ii) a dsRNA comprising an effector sequence comprising or consisting of the sequence set forth in SEQ ID NO: 6 and an effector complement sequence comprising or consisting of the sequence set forth in SEQ ID NO: 7; and
(iii) a dsRNA comprising an effector sequence comprising or consisting of the sequence set forth in SEQ ID NO: 8 and an effector complement sequence comprising or consisting of the sequence set forth in SEQ ID NO: 9.

In another example, a plurality of RNAs of the disclosure are provides as a plurality of shRNAs, wherein the effector sequence of each shRNA is substantially complementary to an effector complement sequence set forth in the column labelled "Effector complement" in Table 4. For example, the effector sequence of each shRNA may comprise or consists of a sequence set forth in the column labelled "Effector" in Table 4. The cognate effector complement sequence may comprise or consist of a sequence set forth in the column labelled "Effector complement" in Table 4.

Exemplary shRNAs comprising an effector sequence which is substantially complementary to an effector complement sequence set forth in the column labelled "Effector complement" in Table 4 are described herein.

An exemplary plurality of RNAs of the disclosure comprises:
(i) a shRNA comprising an effector sequence comprising or consisting of the sequence set forth in SEQ ID NO: 10 and an effector complement sequence comprising or consisting of the sequence set forth in SEQ ID NO: 11; and
(ii) a shRNA comprising an effector sequence comprising or consisting of the sequence set forth in SEQ ID NO: 12 and an effector complement sequence comprising or consisting of the sequence set forth in SEQ ID NO: 13.

An exemplary plurality of RNAs of the disclosure comprises:
(i) a shRNA comprising an effector sequence comprising or consisting of the sequence set forth in SEQ ID NO: 10 and an effector complement sequence comprising or consisting of the sequence set forth in SEQ ID NO: 11; and
(ii) a shRNA comprising an effector sequence comprising or consisting of the sequence set forth in SEQ ID NO: 14 and an effector complement sequence comprising or consisting of the sequence set forth in SEQ ID NO: 15.

An exemplary plurality of RNAs of the disclosure comprises:
(i) a shRNA comprising an effector sequence comprising or consisting of the sequence set forth in SEQ ID NO: 12 and an effector complement sequence comprising or consisting of the sequence set forth in SEQ ID NO: 13; and
(ii) a shRNA comprising an effector sequence comprising or consisting of the sequence set forth in SEQ ID NO: 14 and an effector complement sequence comprising or consisting of the sequence set forth in SEQ ID NO: 15.

An exemplary plurality of RNAs of the disclosure comprises:
(i) a shRNA comprising an effector sequence comprising or consisting of the sequence set forth in SEQ ID NO: 10 and an effector complement sequence comprising or consisting of the sequence set forth in SEQ ID NO: 11;
(ii) a shRNA comprising an effector sequence comprising or consisting of the sequence set forth in SEQ ID NO: 12 and an effector complement sequence comprising or consisting of the sequence set forth in SEQ ID NO: 13; and
(iii) a shRNA comprising an effector sequence comprising or consisting of the sequence set forth in SEQ ID NO: 14 and an effector complement sequence comprising or consisting of the sequence set forth in SEQ ID NO: 15.

As described herein, each shRNA of the plurality will comprise a stem loop sequence positioned between the corresponding effector sequence and effector complement sequence such that the shRNA forms a single contiguous sequence. Exemplary shRNAs are described herein e.g., Table 5.

In one example, the disclosure provides a plurality of RNAs, wherein the plurality comprises or consists of:
(i) a shRNA comprising or consisting of the sequence set forth in SEQ ID NO: 16; and
(ii) a shRNA comprising or consisting of the sequence set forth in SEQ ID NO: 18.

In one example, the disclosure provides a plurality of RNAs, wherein the plurality comprises or consists of:
(i) a shRNA comprising or consisting of the sequence set forth in SEQ ID NO: 16; and
(ii) a shRNA comprising or consisting of the sequence set forth in SEQ ID NO: 20.

In one example, the disclosure provides a plurality of RNAs, wherein the plurality comprises or consists of:
(i) a shRNA comprising or consisting of the sequence set forth in SEQ ID NO: 18; and
(ii) a shRNA comprising or consisting of the sequence set forth in SEQ ID NO: 20.

In one example, the disclosure provides a plurality of RNAs, wherein the plurality comprises or consists of:
(i) a shRNA comprising or consisting of the sequence set forth in SEQ ID NO: 16;
(ii) a shRNA comprising or consisting of the sequence set forth in SEQ ID NO: 18; and
(iii) a shRNA comprising or consisting of the sequence set forth in SEQ ID NO: 20.

Each of the shRNAs described herein may optionally further comprise two contiguous uracils (UU) at the 3' end of the shRNA e.g., as a consequence of transcriptional termination from a RNA Pol III promoter.

In another example, a plurality of RNAs of the disclosure are provides as a plurality of shmiRNAs, wherein the effector sequence of each shmiRNA is substantially complementary to an effector complement sequence set forth in the column labelled "Effector complement" in Table 4. For example, the effector sequence of each shmiRNA may comprise or consists of a sequence set forth in the column labelled "Effector" in Table 4. The cognate effector complement sequence may comprise or consist of a sequence set forth in the column labelled "Effector complement" in Table 4.

Exemplary shmiRNAs comprising an effector sequence which is substantially complementary to an effector complement sequence set forth in the column labelled "Effector complement" in Table 4 are described herein.

An exemplary plurality of RNAs of the disclosure comprises:
(i) a shmiRNA comprising an effector sequence comprising or consisting of the sequence set forth in SEQ ID NO: 10 and an effector complement sequence comprising or consisting of the sequence set forth in SEQ ID NO: 11; and
(ii) a shmiRNA comprising an effector sequence comprising or consisting of the sequence set forth in SEQ ID NO: 12 and an effector complement sequence comprising or consisting of the sequence set forth in SEQ ID NO: 13.

An exemplary plurality of RNAs of the disclosure comprises:
(i) a shmiRNA comprising an effector sequence comprising or consisting of the sequence set forth in SEQ ID NO: 10 and an effector complement sequence comprising or consisting of the sequence set forth in SEQ ID NO: 11; and
(ii) a shmiRNA comprising an effector sequence comprising or consisting of the sequence set forth in SEQ ID NO: 14 and an effector complement sequence comprising or consisting of the sequence set forth in SEQ ID NO: 15.

An exemplary plurality of RNAs of the disclosure comprises:
(i) a shmiRNA comprising an effector sequence comprising or consisting of the sequence set forth in SEQ ID NO: 12 and an effector complement sequence comprising or consisting of the sequence set forth in SEQ ID NO: 13; and
(ii) a shmiRNA comprising an effector sequence comprising or consisting of the sequence set forth in SEQ ID NO: 14 and an effector complement sequence comprising or consisting of the sequence set forth in SEQ ID NO: 15.

An exemplary plurality of RNAs of the disclosure comprises:
(i) a shmiRNA comprising an effector sequence comprising or consisting of the sequence set forth in SEQ ID NO: 10 and an effector complement sequence comprising or consisting of the sequence set forth in SEQ ID NO: 11;
(ii) a shmiRNA comprising an effector sequence comprising or consisting of the sequence set forth in SEQ ID NO: 12 and an effector complement sequence comprising or consisting of the sequence set forth in SEQ ID NO: 13; and
(iii) a shmiRNA comprising an effector sequence comprising or consisting of the sequence set forth in SEQ ID NO: 14 and an effector complement sequence comprising or consisting of the sequence set forth in SEQ ID NO: 15.

As described herein, each shmiRNA of the plurality will comprise a stem loop sequence positioned between the corresponding effector sequence and effector complement sequence such that the shmiRNA forms a single contiguous sequence. Exemplary shmiRNAs are described herein e.g., Table 5.

In one example, the disclosure provides a plurality of RNAs, wherein the plurality comprises or consists of:
(i) a shmiRNA comprising or consisting of the sequence set forth in SEQ ID NO: 16; and
(ii) a shmiRNA comprising or consisting of the sequence set forth in SEQ ID NO: 18.

In one example, the disclosure provides a plurality of RNAs, wherein the plurality comprises or consists of:
(i) a shmiRNA comprising or consisting of the sequence set forth in SEQ ID NO: 16; and
(ii) a shmiRNA comprising or consisting of the sequence set forth in SEQ ID NO: 20.

In one example, the disclosure provides a plurality of RNAs, wherein the plurality comprises or consists of:
(i) a shmiRNA comprising or consisting of the sequence set forth in SEQ ID NO: 18; and
(ii) a shmiRNA comprising or consisting of the sequence set forth in SEQ ID NO: 20.

In one example, the disclosure provides a plurality of RNAs, wherein the plurality comprises or consists of:
(i) a shmiRNA comprising or consisting of the sequence set forth in SEQ ID NO: 16;
(ii) a shmiRNA comprising or consisting of the sequence set forth in SEQ ID NO: 18; and
(iii) a shmiRNA comprising or consisting of the sequence set forth in SEQ ID NO: 20.

Each of the shmiRNAs described herein may optionally further comprise two contiguous uracils (UU) at the 3' end of the mishRNA e.g., as a consequence of transcriptional termination from a RNA Pol III promoter.

In accordance with one example, the plurality of RNAs described herein may be provided together as a single composition.

In accordance with another example, the plurality of RNAs described herein may be provided as multiple compositions. For example, each of the RNAs of the plurality may be provided separately. Alternatively, at least one RNA of the plurality may be provided separately and two or more of the plurality provided together in a composition.

A RNA or plurality RNAs of the disclosure may comprise either synthetic RNAs or DNA-directed RNAs (ddRNAs). Synthetic RNAs may be manufactured by methods known in the art such as by typical oligonucleotide synthesis, and may incorporate chemical modifications to increase half-life and/or efficacy of the siRNA agent, and/or to allow for a more robust delivery formulation. Many chemical modifications of oligonucleotides are known and well described in the art.

In one example, substantially all of the nucleotides of a RNA of the disclosure are modified. In other example, all of the nucleotides of a RNA of the disclosure are modified. RNAs of the disclosure in which "substantially all of the nucleotides are modified" are largely but not wholly modified and can include not more than 5, 4, 3, 2, or 1 unmodified nucleotides.

In one example, a RNA of the disclosure comprises one or more overhang regions and/or capping groups at the 3'-end, 5'-end, or both ends of one or both strands of the duplex. The overhang regions can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one example, the nucleotides in the overhang region of the RNA each independently are a modified or unmodified nucleotide including, but no limited to 2'-sugar modified, such as, 2-F, 2'-O-methyl, thymidine (T), deoxy-thymine (dT), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, dTdT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNA can be phosphorylated. In some examples, the overhang region(s) contains two nucleotides having a phosphorothioate between the two nucleotides, where the two nucleotides can be the same or different.

In one example, a RNA of the disclosure contains only a single overhang, which can strengthen the interference activity of the RNA, without affecting its overall stability. For example, the single-stranded overhang is be located at the 3'-terminal end of the effector sequence or, alternatively, at the 3'-terminal end of the effector complement sequence. In one example, the RNA also comprises a blunt end, located at the 5'-end of the effector complement sequence (or the 3'-end of the effector sequence) or vice versa.

Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of RNAs useful in the disclosure include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some example, a modified RNA will have a phosphorus atom in its internucleoside backbone. Representative U.S. patents that teach the preparation of phosphorus-containing linkages include, but are not limited to, U.S. Pat. Nos. 7,015,315; 7,041,816; 7,273,933; 7,321,029; and U.S. Pat. RE39464.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach exemplary forms of these oligonucleosides include, but are not limited to, U.S. Pat. Nos. 5,663,312; 5,633,360; 5,677,437; and 5,677,439.

In other examples, the RNA(s) of the disclosure comprise or are a RNA mimetic, e.g., the backbone, of the nucleotide units are replaced with novel groups. The base units are maintained for hybridization with an appropriate nucleic acid target compound. One such oligomeric compound, a RNA mimetic that has been shown to have excellent hybridization properties, is referred to as a peptide nucleic acid (PNA). In PNA compounds, the sugar backbone of a RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262.

Modified RNAs can also contain one or more substituted sugar moieties. The RNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_1)_nNH_2$, $O(CH_2)_nCH_3$, $O(CH_2)_nONH_2$, and $O(CH_2)_nON[(CH_2)_nCH_3)]_2$, where n and m are from 1 to about 10.

A RNA of the disclosure can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine.

A RNA of the disclosure can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447).

Potentially stabilizing modifications to the ends of RNA can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

In one example, a RNA of the disclosure is chemically synthesized. Oligonucleotides (e.g., certain modified oligonucleotides or portions of oligonucleotides lacking ribonucleotides) are synthesized using protocols known in the art, for example as described in Caruthers et al., (1992), *Methods in Enzymology* 211, 3-19, WO 99/54459, Wincott et al., (1995), *Nucleic Acids Res.* 23, 2677-2684, Wincott et al., (1997), *Methods Mol. Bio.,* 74, 59, Brennan et al., (1998), *Biotechnol Bioeng.,* 61, 33-45, and Brennan, U.S. Pat. No. 6,001,311. The synthesis of oligonucleotides makes use of common nucleic acid protecting and coupling groups, such as dimethoxytrityl at the 5'-end, and phosphoramidites at the 3'-end.

RNAs without modifications are synthesized using procedures as described in Usman et al., (1987), *J. Am. Chem. Soc.,* 109, 7845; Scaringe et al., (1990), *Nucleic Acids Res.,* 18, 5433. These syntheses makes use of common nucleic acid protecting and coupling groups, such as dimethoxytrityl at the 5'-end, and phosphoramidites at the 3'-end that can be used for certain RNAs of the disclosure.

In certain examples, RNAs of the disclosure are synthesized, deprotected, and analyzed according to methods described in U.S. Pat. Nos. 6,995,259, 6,686,463, 6,673,918, 6,649,751, and/or 6,989,442.

In an alternative example, RNAs of the disclosure are synthesized as discrete components and joined together post-synthetically, for example, by ligation (Moore et al., (1992), Science 256, 9923 or WO 93/23569), or by hybridization following synthesis and/or deprotection.

ddRNAi

A RNA of the disclosure which is a shRNA or shmiRNA can be transcribed from a nucleic acid. Accordingly, in one example, the disclosure provides a nucleic acid encoding a RNA of the disclosure.

In one example, the nucleic acid is DNA.

In another example, the disclosure provides a nucleic acid encoding a plurality of RNAs of the disclosure.

In another example, the disclosure provides a plurality of nucleic acids encoding a plurality of RNAs of the disclosure. For example, each nucleic acid of the plurality may encode a single RNA described herein. In another example, one or more nucleic acids encodes a plurality of RNAs e.g., a nucleic acid of the plurality encodes two or more RNAs of the disclosure and another nucleic acid of the plurality encodes one or more RNAs of the disclosure.

In one example, the plurality of nucleic acids described herein are provided together e.g., in a single composition.

In another example, the plurality of nucleic acids described herein are provided as multiple components e.g., multiple compositions. For example, each of the nucleic acids of the plurality may be provided separately. Alternatively, in an example where at least three nucleic acids of the disclosure are provided, at least one of the nucleic acids may be provided separately and two or more of the plurality provided together.

In some examples, a nucleic acid of the disclosure comprises one or more additional elements e.g., to facilitate transcription of the RNA. For example, the nucleic acid may comprise a promoter operably-linked to a sequence encoding a RNA of the disclosure. Other elements e.g., transcriptional terminators, are known in the art and/or described herein.

In one example, the nucleic acid is a DNA-directed RNAi (ddRNAi) construct.

In one example, the ddRNAi construct comprises a sequence encoding a RNA of the disclosure operably-linked to a promoter.

In one example, the ddRNAi construct comprises a sequence encoding a RNA comprising an effector sequence and an effector complement sequence of the disclosure. As described herein, the RNA of the disclosure will comprise an effector sequence comprising at least 17 contiguous nucleotides which is substantially complementary to a region of a RNA transcript corresponding to a PABPN1 protein, wherein the region of the RNA transcript is set forth in any one of SEQ ID NOs: 1-3. Exemplary effector sequences and effector complement sequences are set forth in Table 4.

For example, the sequences may be operably-linked to a promoter e.g., a U6 or H1. In one example, both sequences may be operably-linked to the same promoter. In one example, both sequences may be operably-linked to different promoters.

In one example, the disclosure provides a ddRNAi construct comprising a sequence encoding an effector sequence and a sequence encoding an effector complement sequence, wherein the effector sequence is substantially complementary to an effector complement sequence described in the column labelled "Effector complement" in Table 4. For example, an effector sequence which is substantially complementary to an effector complement sequence described in the column labelled "Effector complement" in Table 4 may comprise 0, 1, 2, 3 or 4 mismatches when duplexed with the corresponding effector complement sequence in Table 4.

In one example, the disclosure provides an ddRNAi construct comprising a sequence encoding an effector sequence which is substantially complementary to a sequence described in the column labelled "Effector complement" in Table 4, with the exception of 4 base mismatches.

In one example, the disclosure provides an ddRNAi construct comprising a sequence encoding an effector sequence which is substantially complementary to a sequence described in the column labelled "Effector complement" in Table 4, with the exception of 3 base mismatches.

In one example, the disclosure provides an ddRNAi construct comprising a sequence encoding an effector sequence which is substantially complementary to a sequence described in the column labelled "Effector complement" in Table 4, with the exception of 2 base mismatches.

In one example, the disclosure provides an ddRNAi construct comprising a sequence encoding an effector sequence which is substantially complementary to a sequence described in the column labelled "Effector complement" in Table 4, with the exception of a single base mismatch.

In one example, the present disclosure provides a ddRNAi construct comprising a sequence encoding an effector sequence and an effector complement sequence, wherein the effector sequence is 100% complementary to a sequence described in the column labelled "Effector complement" in Table 4. In one example, ddRNAi construct comprises a sequence encoding an effector complement sequence which is substantially complementary to the effector sequence encoded by the ddRNAi construct.

Exemplary ddRNAi constructs of the disclosure comprise sequences encoding corresponding effector and effector complement sequences as described in Table 4.

In one example, the disclosure provides a ddRNAi construct comprising a sequence which encodes an effector sequence and a sequence encoding an effector complement sequence, wherein the effector sequence consists of a sequence set forth in the column labelled "Effector" in Table 4. In one example, the effector complement sequence consists of a sequence set forth in the column labelled "Effector complement" in Table 4.

An exemplary ddRNAi construct of the disclosure comprises a sequence encoding an effector sequence consisting of the sequence set forth in SEQ ID NO: 10 and a sequence encoding an effector complement sequence consisting of the sequence set forth in SEQ ID NO: 11.

Another exemplary ddRNAi construct of the disclosure comprises a sequence encoding an effector sequence consisting of the sequence set forth in SEQ ID NO: 12 and a sequence encoding an effector complement sequence consisting of the sequence set forth in SEQ ID NO: 13.

A further exemplary ddRNAi construct of the disclosure comprises a sequence encoding an effector sequence consisting of the sequence set forth in SEQ ID NO: 14 and a sequence encoding an effector complement sequence consisting of the sequence set forth in SEQ ID NO: 15.

In another example, the disclosure provides a ddRNAi construct encoding a plurality of RNAs of the disclosure or comprising a sequence encoding a RNA of the disclosure and at least one other RNA capable of eliciting RNAi.

In one example, the disclosure provides a ddRNAi construct encoding a plurality of RNAs of the disclosure, wherein each RNA comprises an effector sequence and an effector complement sequence, wherein the effector sequence of at least one (or each) RNA is substantially complementary to a sequence described in the column labelled "Effector complement" in Table 4. Exemplary RNAs of the disclosure comprising an effector sequence which is "substantially complementary" to a sequence described in the column labelled "Effector complement" in Table 4 have been described and shall be taken to apply mutatis mutandis to this example of the disclosure. However, in one example, the disclosure provides a ddRNAi construct encoding a plurality of RNAs of the disclosure, wherein each RNA comprises an effector sequence and an effector complement sequence, wherein the effector sequence of at least one (or each) RNA consists of a sequence set forth in the column labelled "Effector" in Table 4. In one example, the effector complement sequence of at least one (or each) RNA consists of a sequence set forth in the column labelled "Effector complement" in Table 4.

In one example, the disclosure provides a ddRNAi construct encoding a plurality of RNAs of the disclosure, each capable of eliciting RNAi, wherein:

(i) at least one RNA comprises an effector sequence and an effector complement sequence, wherein the effector sequence of the RNA consists of a sequence set forth in the column labelled "Effector" in Table 4 (in one example, the effector complement sequence of each RNA consists of a sequence set forth in the column labelled "Effector complement" in Table 4); and (ii) at least one RNA comprises an effector sequence and an effector complement sequence, wherein the effector sequence of the RNA consists of a sequence of at least 17 contiguous nucleotides which is substantially complementary to a region of the RNA transcript corresponding to a PABPN1 protein which is causative of OPMD.

For example, the at least one RNA at (ii) may be different to the RNA at (i), but consist of a sequence set forth in the column labelled "Effector" in Table 4 (in one example, the effector complement sequence of each RNA consists of a sequence set forth in the column labelled "Effector complement" in Table 4).

An exemplary ddRNAi construct of the disclosure comprises:

(i) a sequence encoding a RNA comprising an effector sequence consisting of the sequence set forth in SEQ ID NO: 10 and an effector complement sequence consisting of the sequence set forth in SEQ ID NO: 11; and (ii) a sequence encoding a RNA comprising an effector sequence comprising or consisting of the sequence set forth in SEQ ID NO: 12 and an effector complement sequence comprising or consisting of the sequence set forth in SEQ ID NO: 13.

An exemplary ddRNAi construct of the disclosure comprises:

(i) a sequence encoding a RNA comprising an effector sequence comprising or consisting of the sequence set forth in SEQ ID NO: 10 and an effector complement sequence comprising or consisting of the sequence set forth in SEQ ID NO: 11; and (ii) a sequence encoding a RNA comprising an effector sequence comprising or consisting of the sequence set forth in SEQ ID NO: 14 and an effector complement sequence comprising or consisting of the sequence set forth in SEQ ID NO: 15.

An exemplary ddRNAi construct of the disclosure comprises:

(i) a sequence encoding a RNA comprising an effector sequence comprising or consisting of the sequence set forth in SEQ ID NO: 12 and an effector complement sequence comprising or consisting of the sequence set forth in SEQ ID NO: 13; and (ii) a sequence encoding a RNA comprising an effector sequence comprising or consisting of the sequence set forth in SEQ ID NO: 14 and an effector complement sequence comprising or consisting of the sequence set forth in SEQ ID NO: 15.

Another exemplary ddRNAi of the disclosure comprises:

(i) a sequence encoding a RNA comprising an effector sequence comprising or consisting of the sequence set forth in SEQ ID NO: 10 and an effector complement sequence comprising or consisting of the sequence set forth in SEQ ID NO: 11;

(ii) a sequence encoding a RNA comprising an effector sequence comprising or consisting of the sequence set forth in SEQ ID NO: 12 and an effector complement sequence comprising or consisting of the sequence set forth in SEQ ID NO: 13; and (iii) a sequence encoding a RNA comprising an effector sequence comprising or consisting of the sequence set forth in SEQ ID NO: 14 and an effector complement sequence comprising or consisting of the sequence set forth in SEQ ID NO: 15.

As described herein, shRNAs and/or shmiRNAs of the disclosure will comprise a stem loop sequence positioned between the corresponding effector sequence and effector complement sequence such that the respective RNA forms a single contiguous sequence. Accordingly, a ddRNAi of the disclosure may comprise a sequence encoding a stem loop positioned between the sequences encoding the corresponding effector sequence and effector complement sequence, respectively.

In one example, the ddRNAi construct comprises a sequence encoding a shRNA of the disclosure operably-linked to a promoter. For example, the ddRNAi construct of the disclosure comprises a sequence encoding a shRNA comprising or consisting of a sequence set forth in Table 5 operably-linked to a promoter e.g., a U6 or H1 promoter.

An exemplary ddRNAi construct may comprise a sequence encoding a shRNA comprising or consisting of the sequence set forth in SEQ ID NO: 16 or 17. In one example, the ddRNAi construct comprises a sequence encoding a shRNA comprising or consisting of the sequence set forth in SEQ ID NO: 16. In one example, the ddRNAi construct comprises a sequence encoding a shRNA comprising or consisting of the sequence set forth in SEQ ID NO: 17.

An exemplary ddRNAi construct may comprise a sequence encoding a shRNA comprising or consisting of the sequence set forth in SEQ ID NO: 18 or 19. In one example, the ddRNAi construct comprises a sequence encoding a shRNA comprising or consisting of the sequence set forth in SEQ ID NO: 18. In one example, the ddRNAi construct comprises a sequence encoding a shRNA comprising or consisting of the sequence set forth in SEQ ID NO: 19.

An exemplary ddRNAi construct may comprise a sequence encoding a shRNA comprising or consisting of the sequence set forth in SEQ ID NO: 20 or 21. In one example, the ddRNAi construct comprises a sequence encoding a shRNA comprising or consisting of the sequence set forth in SEQ ID NO: 20. In one example, the ddRNAi construct comprises a sequence encoding a shRNA comprising or consisting of the sequence set forth in SEQ ID NO: 21.

The present disclosure also provides a ddRNAi construct comprising a sequence encoding a plurality of shRNAs comprising at least one shRNA of the disclosure.

In one example, the present disclosure provides a ddRNAi construct comprising a sequence encoding a plurality of shRNAs, wherein each shRNA comprises an effector sequence comprising or consisting of a sequence of at least 17 contiguous nucleotides which is substantially complementary to a region of the RNA transcript corresponding to a PABPN1 protein which is causative of OPMD, and wherein at least one shRNA comprises an effector sequence which is substantially complementary to an effector complement sequence set forth in the column labelled "Effector complement" in Table 4. Exemplary effector sequences which are substantially complementary to effector complement sequences set forth in the column labelled "Effector complement" in Table 4 have been described and shall be taken to apply mutatis mutandis to this example of the disclosure. For example, the effector sequence of at least one shRNA in the plurality encoded by the ddRNAi construct may comprise or consist of a sequence set forth in the column labelled "Effector" in Table 4 (for example, the cognate effector complement sequence may comprise or consist of a sequence set forth in the column labelled "Effector complement" in Table 4).

In another example, the present disclosure provides a ddRNAi construct comprising a sequence encoding a plurality of shRNAs, wherein the effector sequence of each shRNA comprises or consists of an effector sequence set forth in the column labelled "Effector" in Table 4. The cognate effector complement sequence of the respective shRNAs may comprise or consist of a sequence set forth in the column labelled "Effector complement" in Table 4. Exemplary shRNAs comprising an effector sequence which is substantially complementary to an effector complement sequence set forth in the column labelled "Effector complement" in Table 4 are described herein.

An exemplary ddRNAi construct of the disclosure may comprise a sequence encoding a plurality of shRNAs, the plurality comprising:

(i) a shRNA comprising an effector sequence comprising or consisting of the sequence set forth in SEQ ID NO: 10 and an effector complement sequence comprising or consisting of the sequence set forth in SEQ ID NO: 11; and (ii) a shRNA comprising an effector sequence comprising or consisting of the sequence set forth in SEQ ID NO: 12 and an effector complement sequence comprising or consisting of the sequence set forth in SEQ ID NO: 13.

An exemplary ddRNAi construct of the disclosure may comprise a sequence encoding a plurality of shRNAs, the plurality comprising:

(i) a shRNA comprising an effector sequence comprising or consisting of the sequence set forth in SEQ ID NO: 10 and an effector complement sequence comprising or consisting of the sequence set forth in SEQ ID NO: 11; and (ii) a shRNA comprising an effector sequence comprising or consisting of the sequence set forth in SEQ ID NO: 14 and an effector complement sequence comprising or consisting of the sequence set forth in SEQ ID NO: 15.

An exemplary ddRNAi construct of the disclosure may comprise a sequence encoding a plurality of shRNAs, the plurality comprising:

(i) a shRNA comprising an effector sequence comprising or consisting of the sequence set forth in SEQ ID NO: 12 and an effector complement sequence comprising or consisting of the sequence set forth in SEQ ID NO: 13; and (ii) a shRNA comprising an effector sequence comprising or consisting of the sequence set forth in SEQ ID NO: 14 and an effector complement sequence comprising or consisting of the sequence set forth in SEQ ID NO: 15.

An exemplary ddRNAi construct of the disclosure may comprise a sequence encoding a plurality of shRNAs, the plurality comprising:

(i) a shRNA comprising an effector sequence comprising or consisting of the sequence set forth in SEQ ID NO: 10 and an effector complement sequence comprising or consisting of the sequence set forth in SEQ ID NO: 11;

(ii) a shRNA comprising an effector sequence comprising or consisting of the sequence set forth in SEQ ID NO: 12 and an effector complement sequence comprising or consisting of the sequence set forth in SEQ ID NO: 13; and (iii) a shRNA comprising an effector sequence comprising or consisting of the sequence set forth in SEQ ID NO: 14 and an effector complement sequence comprising or consisting of the sequence set forth in SEQ ID NO: 15.

Exemplary shRNAs of the disclosure are described in Table 5. Accordingly, a ddRNAi construct of the disclosure may comprise a sequence encoding a plurality of the shRNAs described in Table 5.

In one example, the disclosure provides a ddRNAi construct comprising a sequence encoding a plurality of shRNAs, wherein the plurality comprises or consists of:
(i) a shRNA comprising or consisting of the sequence set forth in SEQ ID NO: 16; and
(ii) a shRNA comprising or consisting of the sequence set forth in SEQ ID NO: 18.

In one example, the disclosure provides a ddRNAi construct comprising a sequence encoding a plurality of shRNAs, wherein the plurality comprises or consists of:
(i) a shRNA comprising or consisting of the sequence set forth in SEQ ID NO: 16; and
(ii) a shRNA comprising or consisting of the sequence set forth in SEQ ID NO: 20.

In one example, the disclosure provides a ddRNAi construct comprising a sequence encoding a plurality of shRNAs, wherein the plurality comprises or consists of:
(i) a shRNA comprising or consisting of the sequence set forth in SEQ ID NO: 18; and
(ii) a shRNA comprising or consisting of the sequence set forth in SEQ ID NO: 20.

In one example, the disclosure provides a ddRNAi construct comprising a sequence encoding a plurality of shRNAs, wherein the plurality comprises or consists of:
(i) a shRNA comprising or consisting of the sequence set forth in SEQ ID NO: 16;
(ii) a shRNA comprising or consisting of the sequence set forth in SEQ ID NO: 18; and
(iii) a shRNA comprising or consisting of the sequence set forth in SEQ ID NO: 20.

The present disclosure also provides a ddRNAi construct comprising a sequence encoding a plurality of RNAs, the plurality comprising a shRNA comprising or consisting of the sequence set forth in SEQ ID NO: 16 and at least one other shRNA of the disclosure.

The present disclosure also provides a ddRNAi construct comprising a sequence encoding a plurality of RNAs, the plurality comprising a shRNA comprising or consisting of the sequence set forth in SEQ ID NO: 18 and at least one other shRNA of the disclosure.

The present disclosure also provides a ddRNAi construct comprising a sequence encoding a plurality of RNAs, the plurality comprising a shRNA comprising or consisting of the sequence set forth in SEQ ID NO: 20 and at least one other shRNA of the disclosure.

In another example, the present disclosure provides a ddRNAi construct comprising a sequence encoding a shmiRNA operably-linked to a promoter. For example, the ddRNAi construct of the disclosure comprises a sequence encoding a shmiRNA comprising or consisting of a sequence set forth in Table 5 operably-linked to a promoter e.g., a RNA pol II promoter. Exemplary combinations of effector and effector complement sequences have been described in the context of ddRNAi constructs comprising sequences encoding shRNA(s) of the disclosure and shall be taken to apply mutatis mutandis to this example describing ddRNAi constructs comprising sequences encoding shmiRNAs.

As discussed above, a ddRNAi construct generally comprises a sequence encoding a RNA of the disclosure (e.g., a shRNA or shmiRNA of the disclosure) operably-linked to a promoter. For example, a ddRNAi construct comprising a sequence encoding a shRNA or shmiRNA of the disclosure may be operably-linked to a RNA pol III promoter e.g., U6 or H1 promoter. Alternatively, a ddRNAi construct comprising a sequence encoding a shRNA or shmiRNA of the disclosure may be operably-linked to a RNA pol II promoter e.g., UbC, CMV or PGK promoter. Where the ddRNAi construct encodes a plurality of shRNAs, each of the sequences encoding one of the plurality of shRNAs may be operably-linked to a promoter e.g., a U6 or H1 promoter. Alternatively, where the ddRNAi construct encodes a plurality of shRNAs, each of the sequences encoding the plurality of shRNAs may be operably-linked to the same promoter. For example, a Pol II promoter e.g., UbC, CMV or PGK promoter, may be particularly useful for driving expression of a longer construct comprising sequence encoding a plurality of shRNAs or shmiRNAs.

Often the ddRNAi construct is within a vector, e.g., a plasmid or a miniplasmid or a viral vector.

In one example, the sequences encoding a plurality of RNAs of the disclosure (e.g., shRNAs or shmiRNAs) in the ddRNAi construct are operably-linked to the same promoter. For example, the construct may comprise multiple copies of the same promoter with each copy operably-linked to a sequence encoding a different shRNA or shmiRNAs of the disclosure.

In another example, each promoter operably-linked to a sequence encoding a shRNA or shmiRNA of the disclosure is different. For example, in a ddRNAi construct encoding three shRNAs of the disclosure, the three sequences encoding the respective shRNAs are each operably-linked to a different promoter. Similarly, in a ddRNAi construct encoding three shmiRNAs of the disclosure, the three sequences encoding the respective shmiRNAs are each operably-linked to a different promoter.

In a further example, in a ddRNAi construct encoding three or more shRNAs, two (or more) of the sequences encoding the shRNAs or shmiRNAs are linked to the same promoter and one (or more) of the sequences encoding the RNAs is linked to a different promoter.

In one example, the promoter is a constitutive promoter. The term "constitutive" when made in reference to a promoter means that the promoter is capable of directing transcription of an operably-linked nucleic acid sequence in the absence of a specific stimulus (e.g., heat shock, chemicals, light, etc.). Typically, constitutive promoters are capable of directing expression of a coding sequence in substantially any cell and any tissue. The promoters used to transcribe the RNA of the disclosure include a promoter for ubiquitin, CMV, β-actin, histone H4, EF-1α or pgk genes controlled by RNA polymerase II, or promoter elements controlled by RNA polymerase I.

In one example, a Pol II promoter such as CMV, SV40, U1, β-actin or a hybrid Pol II promoter is employed. Other suitable Pol II promoters are known in the art and may be used in accordance with this example of the disclosure. For example, a Pol II promoter system may be preferred in a ddRNAi construct of the disclosure which expresses a pri-miRNA which, by the action of the enzymes Drosha and Pasha, is processed into one or more shmiRNAs. A Pol II promoter system may also be preferred in a ddRNAi construct of the disclosure comprising sequence encoding a plurality of shRNAs or shmiRNAs under control of a single promoter. A Pol II promoter system may also be preferred where tissue specificity is desired.

In another example, a promoter controlled by RNA polymerase III is used, such as a U6 promoter (U6-1, U6-8, U6-9), H1 promoter, 7SL promoter, a human Y promoter (hY1, hY3, hY4 (See e.g., Maraia, et al., (1994) *Nucleic Acids Res* 22(15):3045-52) and hY5 (see Maraia, et al., (1994) *Nucleic Acids Res* 24(18):3552-59), a human MRP-7-2 promoter, an Adenovirus VA1 promoter, a human tRNA promoter, or a 5s ribosomal RNA promoter. Pol III promoters may be preferred in ddRNAi constructs of the disclosure which express shRNA.

Suitable promoters for use in a ddRNAi construct of the disclosure are described in U.S. Pat. Nos. 8,008,468 and 8,129,510.

In one example, the promoter is a RNA pol III promoter. For example, the promoter is a U6 promoter. In another example, the promoter is a H1 promoter.

Where a promoter in a construct is a U6 promoter, it may be a U6-1 promoter, a U6-8 promoter or a U6-9 promoter (See e.g., Domitrovich, et al., (2003) *Nucleic Acids Res,* 31:2344-2352). For example, a promoter in the construct is a U6-1 promoter. For example, a promoter in the construct is a U6-8 promoter. For example, a promoter in the construct is a U6-9 promoter.

In the case of a ddRNAi construct encoding a plurality of shRNAs of the disclosure, a sequence encoding at least one of the shRNAs is operably-linked to a U6 promoter and a sequence encoding at least one other of the RNAs is operably-linked to a H1 promoter.

In the case of a ddRNAi construct encoding three shRNAs of the disclosure, the sequences encoding two of the shRNAs are each operably-linked to a U6 promoter and a sequence encoding the other of the RNAs is operably-linked to a H1 promoter. For example, when considered in a 5' to 3' direction, the first and second sequences are each operably-linked to a U6 promoter and the third sequence is operably-linked to a H1 promoter. For example, when considered in a 5' to 3' direction, the first sequence may be operably-linked to a U6-1 promoter, the second sequence may be operably-linked to a U6-9 promoter and the third sequence may be operably-linked to a H1 promoter.

In another example, sequences encoding two of the RNAs are each operably-linked to a H1 promoter and a sequence encoding the other of the RNAs is operably-linked to a U6 promoter.

In some examples, promoters of variable strength are employed. For example, use of two or more strong promoters (such as a Pol III-type promoter) may tax the cell, by, e.g., depleting the pool of available nucleotides or other cellular components needed for transcription. In addition or alternatively, use of several strong promoters may cause a toxic level of expression of RNAi agents in the cell. Thus, in some examples one or more of the promoters in the multiple-promoter ddRNAi construct is weaker than other promoters in the construct, or all promoters in the construct may express shRNAs at less than a maximum rate. Promoters may also be modified using various molecular techniques, or otherwise, e.g., through modification of various regulatory elements, to attain weaker levels or stronger levels of transcription. One means of achieving reduced transcription is to modify sequence elements within promoters known to control promoter activity. For example the Proximal Sequence Element (PSE) is known to effect the activity of human U6 promoters (See e.g., Domitrovich, et al., (2003) *Nucleic Acids Res* 31: 2344-2352). Replacing the PSE elements present in strong promoters, such as the human U6-1, U6-8 or U6-9 promoters, with the element from a weak promoter, such as the human U6-7 promoter, reduces the activity of the hybrid U6-1, U6-8 or U6-9 promoters.

Promoters useful in some examples of the present disclosure can be tissue-specific or cell-specific. The term "tissue specific" as it applies to a promoter refers to a promoter that is capable of directing selective transcription of a nucleic acid of interest to a specific type of tissue (e.g., tissue of the eye or muscle) in the relative absence of expression of the same nucleotide sequence of interest in a different type of tissue (e.g., liver). The term "cell-specific" as applied to a promoter refers to a promoter which is capable of directing selective transcription of a nucleic acid of interest in a specific type of cell in the relative absence of expression of the same nucleotide sequence of interest in a different type of cell within the same tissue.

In one example, a ddRNAi construct of the disclosure may additionally comprise one or more enhancers to increase expression of the shRNA(s) or shmiRNA(s) of the disclosure. Enhancers appropriate for use in examples of the present disclosure include a CMV enhancer (Xia et al, (2003) *Nucleic Acids Res* 31(17): e100), and other enhancers known to those skilled in the art.

In a further example, a ddRNAi construct of the disclosure may comprise a transcriptional terminator linked to a nucleic acid encoding a shRNA or shmiRNA of the disclosure. In the case of a ddRNAi construct encoding multiple shRNAs or multiple shmiRNA, the terminators linked to each nucleic acid can be the same or different. In one example, the terminator is a contiguous stretch of 4 or more or 5 or more or 6 or more T residues e.g., such as in the case of a ddRNAi construct encoding shRNA(s) under control of one or more pol III promoter(s).

In some examples, where different promoters are used, the terminators can be different and are matched to the promoter from the gene from which the terminator is derived. Such terminators include the SV40 poly A, the AdV VA1 gene, the 5S ribosomal RNA gene, and the terminators for human t-RNAs. In addition, promoters and terminators may be mixed and matched, as is commonly done with RNA pol II promoters and terminators.

In one example, the promoter and terminator in each promoter/RNA encoding sequence/terminator component in a ddRNAi construct encoding multiple RNAs are all different to decrease the likelihood of DNA recombination events between components.

In an example, a ddRNAi construct of the disclosure comprises a sequence encoding a shRNA of the disclosure operably-linked to a U6 promoter and linked to a terminator comprising at least four thymidine residues e.g., 4 or 5 or 6 thymidine residues. Optionally, the sequence encoding the shRNA may also be linked to a transcription initiator comprising a single guanine.

In an example, a ddRNAi construct of the disclosure comprises a sequence encoding a shRNA consisting of a sequence set forth in Table 5 operably-linked to a promoter, e.g., a U6 or H1 promoter. In one example, the sequence encoding the shRNA is linked to a terminator e.g., comprising at least four thymidine residues, such as 4 or 5 or 6 thymidine residues.

One exemplary ddRNAi construct comprises a sequence encoding a shRNA comprising or consisting of the sequence set forth in SEQ ID NO: 16 operably-linked to a U6 promoter e.g., a U6-1 promoter, and a terminator sequence comprising six contiguous thymidine residues.

Another exemplary ddRNAi construct comprises a sequence encoding a shRNA comprising or consisting of the sequence set forth in SEQ ID NO: 18 operably-linked to a U6 promoter e.g., a U6-9 promoter, and a terminator comprising six contiguous thymidine residues.

Another exemplary ddRNAi construct comprises a sequence encoding a shRNA comprising or consisting of the sequence set forth in SEQ ID NO: 20 operably-linked to a H1 promoter and a terminator comprising five contiguous thymidine residues.

In another example, the disclosure provides a ddRNAi construct comprising a sequence encoding a plurality of shRNAs, wherein the ddRNAi construct comprises (i) a sequence encoding a shRNA comprising or consisting of a sequence set forth in Table 5 operably-linked to a promoter e.g., a U6 or H1 promoter, and (ii) a sequence encoding at least one other shRNA of the disclosure operably-linked to a promoter. In one example, the sequence at (i) is linked to a terminator e.g., comprising at least five contiguous thymidine residues. In one example, the sequence at (ii) is linked to a terminator e.g., comprising at least five thymidine residues. In one example, the sequences at (i) and (ii) are each linked to a terminator e.g., comprising at least five thymidine residues.

In one example, the disclosure provides a ddRNAi construct comprising a sequence encoding a plurality of shRNAs, wherein the ddRNAi construct comprises: (i) a sequence encoding a shRNA comprising or consisting of the sequence set forth in SEQ ID NO: 16 operably-linked to a U6 promoter e.g., a U6-1 promoter, and a terminator comprising six contiguous thymidine residues; and (ii) a sequence encoding at least one other shRNA of the disclosure operably-linked to a promoter and a terminator comprising at least four thymidine residues.

In one example, the disclosure provides a ddRNAi construct comprising a sequence encoding a plurality of shRNAs, wherein the ddRNAi construct comprises: (i) a sequence encoding a shRNA comprising or consisting of the sequence set forth in SEQ ID NO: 18 operably-linked to a U6 promoter e.g., a U6-9 promoter, and a terminator comprising six contiguous thymidine residues; and (ii) a sequence encoding at least one other shRNA of the disclosure operably-linked to a promoter and a terminator comprising at least four thymidine residues.

In one example, the disclosure provides a ddRNAi construct comprising a sequence encoding a plurality of shRNAs, wherein the ddRNAi construct comprises: (i) a sequence encoding a shRNA comprising or consisting of the sequence set forth in SEQ ID NO: 20 operably-linked to a H1 promoter and a terminator comprising five contiguous thymidine residues; and (ii) a sequence encoding at least one other shRNA of the disclosure operably-linked to a promoter and a terminator comprising at least four thymidine residues.

The present disclosure also provides a ddRNAi construct comprising a sequence encoding a plurality of shRNAs, wherein the ddRNAi construct comprises:
(i) a sequence encoding a shRNA comprising or consisting of the sequence set forth in SEQ ID NO: 16 operably-linked to a U6 promoter e.g., a U6-1 promoter, and a terminator comprising six contiguous thymidine residues; and
(ii) a sequence encoding a shRNA comprising or consisting of the sequence set forth in SEQ ID NO: 18 operably-linked to a U6 promoter e.g., a U6-9 promoter, and a terminator comprising six contiguous thymidine residues.

The present disclosure also provides a ddRNAi construct comprising a sequence encoding a plurality of shRNAs, wherein the ddRNAi construct comprises:
(i) a sequence encoding a shRNA comprising or consisting of the sequence set forth in SEQ ID NO: 16 operably-linked to a U6 promoter e.g., a U6-1 promoter, and a terminator comprising six contiguous thymidine residues; and
(ii) a sequence encoding a shRNA comprising or consisting of the sequence set forth in SEQ ID NO: 20 operably-linked to a H1 promoter and a terminator comprising five contiguous thymidine residues.

The present disclosure also provides a ddRNAi construct comprising a sequence encoding a plurality of shRNAs, wherein the ddRNAi construct comprises:
(i) a sequence encoding a shRNA comprising or consisting of the sequence set forth in SEQ ID NO: 18 operably-linked to a U6 promoter e.g., a U6-1 promoter, and a terminator comprising six contiguous thymidine residues; and
(ii) a sequence encoding a shRNA comprising or consisting of the sequence set forth in SEQ ID NO: 20 operably-linked to a H1 promoter and a terminator comprising five contiguous thymidine residues.

The present disclosure also provides a ddRNAi construct comprising a sequence encoding a plurality of shRNAs, wherein the ddRNAi construct comprises:
(i) a sequence encoding a shRNA comprising or consisting of the sequence set forth in SEQ ID NO: 16 operably-linked to a U6 promoter e.g., a U6-1 promoter, and a terminator comprising six contiguous thymidine residues;
(ii) a sequence encoding a shRNA comprising or consisting of the sequence set forth in SEQ ID NO: 18 operably-linked to a U6 promoter e.g., a U6-9 promoter, and a terminator comprising six contiguous thymidine residues; and
(iii) a sequence encoding a shRNA comprising or consisting of the sequence set forth in SEQ ID NO: 20 operably-linked to a H1 promoter and a terminator comprising five contiguous thymidine residues.

In another example, the present disclosure provides a plurality of ddRNAi constructs each encoding a shRNA, wherein at least one of the ddRNAi constructs in the plurality is a ddRNAi construct comprising a sequence encoding a shRNA of the disclosure. Exemplary shRNAs of the disclosure have been described and shall be taken to apply mutatis mutandis to this example.

In one example, the present disclosure provides a plurality of ddRNAi constructs each comprising a sequence encoding a shRNA, wherein at least one of the ddRNAi constructs in the plurality is a ddRNAi construct comprising a sequence encoding a shRNA comprising an effector sequence which is substantially complementary to an effector complement sequence set forth in the column labelled "Effector complement" in Table 4. Exemplary effector sequences which are substantially complementary to effector complement sequences set forth in the column labelled "Effector complement" in Table 4 have been described and shall be taken to apply mutatis mutandis to this example of the disclosure. For example, the effector sequence of the shRNA encoded by the at least one ddRNAi construct may comprise or consist of a sequence set forth in the column labelled "Effector" in Table 4 (the cognate effector complement sequence of the shRNA encoded by the at least one ddRNAi construct may, for example, comprise or consist of a sequence set forth in the column labelled "Effector complement" in Table 4).

In another example, the present disclosure provides a plurality of ddRNAi constructs each comprising a sequence encoding a shRNA, wherein each of the ddRNAi constructs comprises a sequence encoding a shRNA which comprises or consists of an effector sequence set forth in the column labelled "Effector" in Table 4. The cognate effector complement sequence of the respective shRNAs may comprise or consist of a sequence set forth in the column labelled "Effector complement" in Table 4. Exemplary ddRNAi constructs in the plurality of ddRNAi constructs comprise a sequence encoding a shRNA comprising an effector sequence which is substantially complementary to an effector complement sequence set forth in the column labelled "Effector complement" in Table 4 are described herein.

An exemplary plurality of ddRNAi constructs of the disclosure comprises:

(i) a ddRNAi construct comprising a sequence encoding a shRNA comprising an effector sequence comprising or consisting of the sequence set forth in SEQ ID NO: 10 and an effector complement sequence comprising or consisting of the sequence set forth in SEQ ID NO: 11; and (ii) a ddRNAi construct comprising a sequence encoding a shRNA comprising an effector sequence comprising or consisting of the sequence set forth in SEQ ID NO: 12 and an effector complement sequence comprising or consisting of the sequence set forth in SEQ ID NO: 13.

An exemplary plurality of ddRNAi constructs of the disclosure comprises:

(i) a ddRNAi construct comprising a sequence encoding a shRNA comprising an effector sequence comprising or consisting of the sequence set forth in SEQ ID NO: 10 and an effector complement sequence comprising or consisting of the sequence set forth in SEQ ID NO: 11; and (ii) a ddRNAi construct comprising a sequence encoding a shRNA comprising an effector sequence comprising or consisting of the sequence set forth in SEQ ID NO: 14 and an effector complement sequence comprising or consisting of the sequence set forth in SEQ ID NO: 15.

An exemplary plurality of ddRNAi constructs of the disclosure comprises:

(i) a ddRNAi construct comprising a sequence encoding a shRNA comprising an effector sequence comprising or consisting of the sequence set forth in SEQ ID NO: 12 and an effector complement sequence comprising or consisting of the sequence set forth in SEQ ID NO: 13; and (ii) a ddRNAi construct comprising a sequence encoding a shRNA comprising an effector sequence comprising or consisting of the sequence set forth in SEQ ID NO: 14 and an effector complement sequence comprising or consisting of the sequence set forth in SEQ ID NO: 15.

An exemplary plurality of ddRNAi constructs of the disclosure comprises:

(i) a ddRNAi construct comprising a sequence encoding a shRNA comprising an effector sequence comprising or consisting of the sequence set forth in SEQ ID NO: 10 and an effector complement sequence comprising or consisting of the sequence set forth in SEQ ID NO: 11;

(ii) a ddRNAi construct comprising a sequence encoding a shRNA comprising an effector sequence comprising or consisting of the sequence set forth in SEQ ID NO: 12 and an effector complement sequence comprising or consisting of the sequence set forth in SEQ ID NO: 13; and (iii) a ddRNAi construct comprising a sequence encoding a shRNA comprising an effector sequence comprising or consisting of the sequence set forth in SEQ ID NO: 14 and an effector complement sequence comprising or consisting of the sequence set forth in SEQ ID NO: 15.

In accordance with the examples described herein, at least one ddRNAi construct of the plurality may comprises a sequence encoding a shRNA described in Table 5. The sequence encoding a shRNA described in Table 5 may be operably-linked to a promoter e.g., a U6 or H1 promoter. Each of the shRNAs described Table 5 may optionally further comprise two contiguous uracils (UU) at the 3' end of the shRNA e.g., as a consequence of transcriptional termination from a RNA Pol III promoter.

In one example, the present disclosure provides a plurality of ddRNAi constructs comprising two or more ddRNAi constructs, each comprising a sequence encoding a shRNA of the disclosure. For example, each ddRNAi construct of the plurality may comprise a sequence encoding a shRNA described in Table 5 operably-linked to a promoter e.g., a U6 or H1 promoter.

In one example, the plurality of ddRNA constructs comprises:

(i) a ddRNAi construct comprising a sequence encoding a shRNA comprising or consisting of the sequence set forth in SEQ ID NO: 16 operably-linked to a U6 promoter e.g., a U6-1 promoter, and a terminator sequence comprising six contiguous thymidine residues; and (ii) a ddRNAi construct comprising a sequence encoding a shRNA comprising or consisting of the sequence set forth in SEQ ID NO: 18 operably-linked to a U6 promoter e.g., a U6-9 promoter, and a terminator sequence comprising six contiguous thymidine residues.

In one example, the plurality of ddRNA constructs comprises:

(i) a ddRNAi construct comprising a sequence encoding a shRNA comprising or consisting of the sequence set forth in SEQ ID NO: 16 operably-linked to a U6 promoter e.g., a U6-1 promoter, and a terminator sequence comprising six contiguous thymidine residues; and (ii) a ddRNAi construct comprising a sequence encoding a shRNA comprising or consisting of the sequence set forth in SEQ ID NO: 20 operably-linked to a H1 promoter and a terminator sequence comprising five contiguous thymidine residues.

In one example, the plurality of ddRNA constructs comprises:

(i) a ddRNAi construct comprising a sequence encoding a shRNA comprising or consisting of the sequence set forth in SEQ ID NO: 18 operably-linked to a U6 promoter e.g., a U6-9 promoter, and a terminator sequence comprising six contiguous thymidine residues; and (ii) a ddRNAi construct comprising a sequence encoding a shRNA comprising or consisting of the sequence set forth in SEQ ID NO: 20 operably-linked to a H1 promoter and a terminator sequence comprising five contiguous thymidine residues.

In one example, the plurality of ddRNA constructs comprises:

(i) a ddRNAi construct comprising a sequence encoding a shRNA comprising or consisting of the sequence set forth in SEQ ID NO: 16 operably-linked to a U6 promoter e.g., a U6-1 promoter, and a terminator sequence comprising six contiguous thymidine residues;

(ii) a ddRNAi construct comprising a sequence encoding a shRNA comprising or consisting of the sequence set forth in SEQ ID NO: 18 operably-linked to a U6 promoter e.g., a U6-9 promoter, and a terminator sequence comprising six contiguous thymidine residues; and (iii) a ddRNAi construct comprising a sequence encoding a shRNA comprising or consisting of the sequence set forth in SEQ ID NO: 20 operably-linked to a H1 promoter and a terminator sequence comprising five contiguous thymidine residues.

In addition, the or each ddRNAi construct can comprise one or more multiple cloning sites and/or unique restriction sites that are located strategically, such that the promoter, shRNA encoding sequence and/or terminator elements are easily removed or replaced. The or each ddRNAi construct can be assembled from smaller oligonucleotide components using strategically located restriction sites and/or complementary sticky ends. The base vector for one approach according to the present disclosure comprises plasmids with a multilinker in which all sites are unique (though this is not an absolute requirement). Sequentially, each promoter is inserted between its designated unique sites resulting in a base cassette with one or more promoters, all of which can have variable orientation. Sequentially, again, annealed primer pairs are inserted into the unique sites downstream of each of the individual promoters, resulting in a single-, double- or multiple-expression cassette construct. The insert can be moved into, e.g. an AVV backbone using two unique restriction enzyme sites (the same or different ones) that flank the single-, double- or multiple-expression cassette insert.

Generation of the or each construct can be accomplished using any suitable genetic engineering techniques known in the art, including without limitation, the standard techniques of PCR, oligonucleotide synthesis, restriction endonuclease digestion, ligation, transformation, plasmid purification, and DNA sequencing. If the or each construct is a viral construct, the construct comprises, for example, sequences necessary to package the ddRNAi construct into viral particles and/or sequences that allow integration of the ddRNAi construct into the target cell genome. In some examples, the or each viral construct additionally contains genes that allow for replication and propagation of virus, however such genes will be supplied in trans. Additionally, the or each viral construct cam contain genes or genetic sequences from the genome of any known organism incorporated in native form or modified. For example, a viral construct may comprise sequences useful for replication of the construct in bacteria.

The or each construct also may contain additional genetic elements. The types of elements that may be included in the construct are not limited in any way and may be chosen by one with skill in the art. For example, additional genetic elements may include a reporter gene, such as one or more genes for a fluorescent marker protein such as GFP or RFP; an easily assayed enzyme such as beta-galactosidase, luciferase, beta-glucuronidase, chloramphenical acetyl transferase or secreted embryonic alkaline phosphatase; or proteins for which immunoassays are readily available such as hormones or cytokines.

Other genetic elements that may find use in embodiments of the present disclosure include those coding for proteins which confer a selective growth advantage on cells such as adenosine deaminase, aminoglycodic phosphotransferase, dihydrofolate reductase, hygromycin-B-phosphotransferase, drug resistance, or those genes coding for proteins that provide a biosynthetic capability missing from an auxotroph. If a reporter gene is included along with the or each construct, an internal ribosomal entry site (IRES) sequence can be included. In one example, the additional genetic elements are operably-linked with and controlled by an independent promoter/enhancer. In addition a suitable origin of replication for propagation of the construct in a bacterial or cell culture may be employed. The sequence of the origin of replication generally is separated from the ddRNAi construct and other genetic sequences. Such origins of replication are known in the art and include the pUC, ColE1, 2-micron or SV40 origins of replication.

Expression Constructs

In one example, a ddRNAi construct of the disclosure is included within an expression construct.

In one example, the expression construct is an expression vector.

In one example, the expression vector is a plasmid, e.g., as is known in the art. In one example, a suitable plasmid expression vector is a pAAV vector e.g., a self-complementary pAAV (pscAAV) plasmid vector or single-stranded pAAV (pssAAV) plasmid vector. As described herein, the plasmid may comprise one or more RNA pol III promoter(s) e.g., to drive expression of one or more RNAs of the disclosure. Suitable RNA pol III promoters for inclusion in an expression vector have been described herein.

In one example, the expression vector is mini-circle DNA. Mini-circle DNA is described in U.S. Patent Publication No. 2004/0214329. Mini-circle DNA are useful for persistently high levels of nucleic acid transcription. The circular vectors are characterized by being devoid of expression-silencing bacterial sequences. For example, mini-circle vectors differ from bacterial plasmid vectors in that they lack an origin of replication, and lack drug selection markers commonly found in bacterial plasmids, e.g. β-lactamase, tet, and the like. Consequently, minicircle DNA becomes smaller in size, allowing more efficient delivery.

In one example, the expression vector is a viral vector.

A viral vector based on any appropriate virus may be used to deliver a ddRNAi of the disclosure. In addition, hybrid viral systems may be of use. The choice of viral delivery system will depend on various parameters, such as the tissue targeted for delivery, transduction efficiency of the system, pathogenicity, immunological and toxicity concerns, and the like.

Commonly used classes of viral systems used in gene therapy can be categorized into two groups according to whether their genomes integrate into host cellular chromatin (retroviruses and lentiviruses) or persist in the cell nucleus predominantly as extrachromosomal episomes (adeno-associated virus, adenoviruses and herpesviruses). In one example, a viral vector of the disclosure integrates into a host cell's chromatin. In another example, a viral vector of the disclosure persists in a host cell's nucleus as an extrachromosomal episome.

In one example, a viral vector is from the Parvoviridae family. The Parvoviridae is a family of small single-stranded, non-enveloped DNA viruses with genomes approximately 5000 nucleotides long. Included among the family members is adeno-associated virus (AAV). In one example, a viral vector of the disclosure is an AAV. AAV is a dependent parvovirus that generally requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells. Because progeny virus is not produced from AAV infection in the absence of helper virus, the extent of transduction is restricted only to the initial cells that are infected with the virus. It is this feature which makes AAV a desirable vector for the present disclosure. Furthermore, unlike retrovirus, adenovirus, and herpes simplex virus, AAV appears to lack human pathogenicity and toxicity (Kay, et al., (2003) *Nature*. 424: 251). Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as shRNA.

In one example, a viral vector is an adenoviral (AdV) vector. Adenoviruses are medium-sized double-stranded, non-enveloped DNA viruses with linear genomes that are between 26-48 kbp. Adenoviruses gain entry to a target cell by receptor-mediated binding and internalization, penetrating the nucleus in both non-dividing and dividing cells. Adenoviruses are heavily reliant on the host cell for survival and replication and are able to replicate in the nucleus of vertebrate cells using the host's replication machinery.

Another viral delivery system useful with the ddRNAi constructs of the disclosure is a system based on viruses from the family Retroviridae. Retroviruses comprise single-stranded RNA animal viruses that are characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome.

In some examples, a viral vector is a lentivirus. Lentivirus vectors are often pseudotyped with vesicular steatites virus glycoprotein (VSV-G), and have been derived from the human immunodeficiency virus (HIV); visan-maedi, which causes encephalitis (visna) or pneumonia in sheep; equine infectious anemia virus (EIAV), which causes autoimmune hemolytic anemia and encephalopathy in horses; feline immunodeficiency virus (FIV), which causes immune deficiency in cats; bovine immunodeficiency virus (BIV) which causes lymphadenopathy and lymphocytosis in cattle; and simian immunodeficiency virus (SIV), which causes immune deficiency and encephalopathy in non-human primates. Vectors that are based on HIV generally retain <5% of the parental genome, and <25% of the genome is incorporated into packaging constructs, which minimizes the possibility of the generation of reverting replication-competent HIV. Biosafety has been further increased by the development of self-inactivating vectors that contain deletions of the regulatory elements in the downstream long-terminal-repeat sequence, eliminating transcription of the packaging signal that is required for vector mobilization. One of the main advantages to the use of lentiviral vectors is that gene transfer is persistent in most tissues or cell types, even following cell division of the transduced cell.

A lentiviral-based construct used to express a RNA of the disclosure comprises sequences from the 5' and 3' long terminal repeats (LTRs) of a lentivirus. In one example, the viral construct comprises an inactivated or self-inactivating 3' LTR from a lentivirus. The 3' LTR may be made self-inactivating by any method known in the art. For example, the U3 element of the 3' LTR contains a deletion of its enhancer sequence, e.g., the TATA box, Sp1 and NF-kappa B sites. As a result of the self-inactivating 3' LTR, the provirus that is integrated into the host genome will comprise an inactivated 5' LTR. The LTR sequences may be LTR sequences from any lentivirus from any species. The lentiviral-based construct also may incorporate sequences for MMLV or MSCV, RSV or mammalian genes. In addition, the U3 sequence from the lentiviral 5' LTR may be replaced with a promoter sequence in the viral construct. This may increase the titer of virus recovered from the packaging cell line. An enhancer sequence may also be included.

Other viral or non-viral systems known to those skilled in the art may be used to deliver the ddRNAi or nucleic acid of the present invention to cells of interest, including but not limited to gene-deleted adenovirus-transposon vectors (see Yant, et al., (2002) *Nature Biotech.* 20:999-1004); systems derived from Sindbis virus or Semliki forest virus (see Perri, et al., (2002) *J. Virol.* 74(20):9802-9807); systems derived from Newcastle disease virus or Sendai virus.

Testing a RNA or ddRNAi Construct of the Disclosure

Cell Culture Models

An example of cell line useful as a cell culture model for OPMD is the HEK293T cell line (HEK293T, ATCC, Manassas, USA) described in Example 3 which has been transfected with a vector expressing normal Ala10-human-PABPN1-FLAG (Ala10) or mutant Ala17-humanPABPN1-FLAG (Ala17), the latter being hallmark of OPMD.

Another example of a cell line useful as a cell culture model for OPMD is the primary mouse myoblast (IM2) cell line stably transfected to express either normal Ala10-humanPABPN1-FLAG (Ala10) or mutant Ala17-human-PABPN1-FLAG (Ala17). An exemplary IM2 derived cell line which stably expresses mutant Ala17-humanPABPN1-FLAG (Ala17) is the H2kB-D7e cell line described in Example 3. The H2kB-D7e cell line is also described in Raz et al., (2011) *American Journal of Pathology*, 179(4):1988-2000.

Other cell lines suitable for cell culture models of OPMD are known in the art, such as described in Fan et al., (2001) *Human Molecular Genetics*, 10:2341-2351, Bao et al., (2002) *The Journal of Biological Chemistry*, 277:12263-12269, and Abu-Baker et al., (2003) *Human Molecular Genetics*, 12: 2609-2623.

As exemplified herein, activity of a RNA or ddRNAi construct of the disclosure is determined by administering the RNA or ddRNAi construct to the cell and subsequently measuring the level of expression of a RNA or protein encoded by the PABPN1 gene. For example, intracellular PABPN1 gene expression can be assayed by any one or more of RT-PCR, quantitative PCR, semi-quantitative PCR, or in-situ hybridization under stringent conditions, using one or more probes or primers which are specific for PABPN1. Extracellular PABPN1 can also be assayed either by PCR using one or more probes or primers which are specific for PABPN1 DNA or ELISA for PABPN1 protein.

Polynucleotides which may be used in RT-PCR, quantitative PCR or semi-quantitative PCR techniques for detecting PABPN1 expression are known and commercially available (Thermo Fisher). However, polynucleotides useful for PCR-based detection methods can be designed based on sequence information available for PABPN1 using method and/or software known in the art. In one example, the presence or absence of PABPN1 mRNA may be detected using RT-PCR using standard methodologies known in the art. In one example, the presence or absence or relative amount of PABPN1 polypeptide or protein may be detected using any one or more of Western blotting, ELISA, or other standard quantitative or semiquantitative techniques available in the art, or a combination of such techniques. Techniques relying on antibody recognition of PABPN1 are contemplated and are described herein e.g., in Examples 3-5. In one example, the presence or absence or relative abundance of PABPN1 polypeptide may be detected with techniques which comprise antibody capture of PABPN1 polypeptides in combination with electrophoretic resolution of captured PABPN1 polypeptides, for example using the Isonostic™ Assay (Target Discovery, Inc.). Antibodies are commercially available for PABPN1 protein.

Various means for normalizing differences in transfection or transduction efficiency and sample recovery are known in the art.

A RNA or ddRNAi construct of the disclosure that reduces expression of a mRNA or protein encoded by PABPN1 or that reduces the presence of nuclear aggregates of PABPN1 protein, relative to a level of mRNA expression or protein encoded by PABPN1 or an amount of nuclear aggregates of PABPN1 protein in the absence of the RNA of the disclosure, is considered to be useful for therapeutic applications e.g., such as treating OPMD by reducing expression of endogenous PABPN1 and replacing some or all of the endogenous PABPN1 with a PABPN1 protein which is not causative of OPMD as described herein.

Animal Models

There are several small animal models available for studying OPMD, examples of which are described in Uyama et al., (2005) *Acta Myologica,* 24(2):84-88 and Chartier and Simonelig (2013) *Drug Discovery Today: technologies,* 10:e103-107. An exemplary animal model is the A17.1 transgenic mouse model described in Examples 4 and 5 herein and which has been described previously in Davies et al., (2005) Nature Medicine, 11:672-677 and Trollet et al., (2010) *Human Molecular Genetics,* 19(11):2191-2207.

Any of the foregoing animal models can be used to determine the efficacy of a RNA or ddRNAi construct of the disclosure to knockdown, reduce or inhibit expression of a RNA or protein encoded by the PABPN1 gene.

Methods for assaying intracellular and extracellular PABPN1 gene expression have been described herein with respect to cell models and shall be taken to apply mutatis mutandis to this example of the disclosure.

Agents for Replacement of Functional PABPN1

In one example, the present disclosure provides an agent for replacement of functional PABPN1 protein e.g., to a cell or animal. The functional PABPN1 protein will not be causative of OPMD, nor will it be encoded by a mRNA transcript which is targeted by the RNA(s) of the disclosure.

In one example, the agent for replacement of functional PABPN1 protein to a cell or animal is a nucleic acid e.g., such as DNA or cDNA, encoding the functional PABPN1 protein. For example, the nucleic acid encoding the functional PABPN1 protein may be codon optimised e.g., contain one or more degenerate or wobble bases relative to the wild type PABPN1 nucleic acid but which encodes for identical amino acids, so that the corresponding mRNA sequence coding for the functional PABPN1 protein is not recognised by the RNA(s) of the disclosure. For example, a codon optimised nucleic acid encoding the functional PABPN1 protein may comprise one or more degenerate or wobble bases relative to the wild type PABPN1 nucleic acid within the region targeted by the RNA(s) of the disclosure. In one example, the one or more degenerate or wobble bases resides within a seed region of the RNA of the disclosure.

In one example, nucleic acid encoding the functional PABPN1 protein is codon optimised such that its corresponding mRNA sequence is not recognised by the RNA(s) of the disclosure. For example, the functional PABPN1 protein encoded by the codon optimised nucleic acid sequence may comprise the amino acid sequence set forth in SEQ ID NO: 25 i.e., the amino acid sequence of the wild-type human PABPN1 protein. In one example, the agent for replacement of functional PABPN1 protein e.g., a PABPN1 protein having the amino acid sequence set forth in SEQ ID NO: 25, is a nucleic acid comprising the sequence set forth in SEQ ID NO: 24. In one example, the nucleic acid encoding the functional PABPN1 protein may also comprise a kozak sequence.

In one example, the functional PABPN1 protein is be appended to or comprises an epitope tag e.g., a Myc-tag. For example, a functional PABPN1 protein comprising a Myc-tag may comprise the amino acid sequence set forth in SEQ ID NO: 27. According to this example, the agent for replacement of functional PABPN1 protein may be a nucleic acid comprising the sequence set forth in SEQ ID NO: 26.

In one example, the codon-optimised nucleic acid encoding the functional PABPN1 protein is operably-linked to a promoter suitable for expression of the functional PABPN1 protein. One exemplary promoter suitable for use with the nucleic acid encoding the functional PABPN1 protein is a SpC512 promoter. However, any suitable promoter known in the art may be used. For example, other suitable promoters for use with the nucleic acid encoding the functional PABPN1 protein are described in US 20110212529 A1.

As described herein, promoters useful in some examples of the present disclosure can be tissue-specific or cell-specific.

In one example, a codon-optimised nucleic acid encoding the functional PABPN1 protein of the disclosure may additionally comprise one or more enhancers to increase expression of the functional PABPN1 protein and its corresponding mRNA transcript. Enhancers appropriate for use in this example of the present disclosure will be known to those skilled in the art.

A nucleic acid encoding the functional PABPN1 protein may be comprised within an expression vector. Exemplary expression vectors have been described in the context of RNAs and ddRNAi constructs of the disclosure and shall be taken to apply mutatis mutandis to this example.

Accordingly, in one example, an agent for replacement of functional PABPN1 protein to a cell or animal may be an expression vector comprising a codon-optimised nucleic acid encoding the functional PABPN1 protein. For example, an expression vector of the disclosure may comprise the codon-optimised nucleic acid encoding the functional PABPN1 protein e.g., the sequence set forth in SEQ ID NO: 24, and a promoter for expression therefor e.g., a SpC512 promoter. In one example, the codon optimised nucleic acid encoding the functional PABPN1 protein may also comprise a kozak sequence. Thus, an expression vector of the disclosure may comprise a sequence set forth in SEQ ID NO: 24 with a kozak sequence at the 5' end thereof.

In one example, the agent for replacement of functional PABPN1 protein e.g., having a sequences set forth in SEQ ID NO: 25, is a codon-optimised nucleic acid comprising or consisting of the sequence set forth in SEQ ID NO: 24. In one example, the codon optimised nucleic acid further comprises a kozak sequence. Thus, the agent for replacement of functional PABPN1 protein may be a nucleic acid comprising or consisting of the sequence set forth in SEQ ID NO: 24 with a kozak sequence at the 5' end thereof.

In one example, the nucleic acid encoding the functional PABPN1 protein as described herein may be comprised within a plasmid expression vector. Suitable plasmid expression vectors have been described herein and will be known in the art. In one example, a suitable plasmid expression vector is a pAAV vector e.g., a pscAAV plasmid vector or pssAAV plasmid vector.

In one example, the expression vector is mini-circle DNA. Mini-circle DNA vectors have been described herein.

In one example, the expression vector is a viral vector. For example, a viral vector based on any appropriate virus may be used to deliver a codon optimised nucleic acid encoding the functional PABPN1 protein of the disclosure. In addition, hybrid viral systems may be of use. The choice of viral delivery system will depend on various parameters, such as the tissue targeted for delivery, transduction efficiency of the system, pathogenicity, immunological and toxicity concerns, and the like.

Exemplary viral systems for delivery of genetic material to a cell or animal have been described in the context of the RNAs and ddRNAi constructs of the disclosure and shall be taken to apply mutatis mutandis to this example.

In one example, the viral vector is an AAV.

In one example, the viral vector is an AdV vector.

In one example, the viral vector is a lentivirus.

Other viral or non-viral systems known to those skilled in the art may be used to deliver the codon-optimised nucleic acid encoding functional PABPN1 protein of the present disclosure to cells of interest, including but not limited to gene-deleted adenovirus-transposon vectors (see Yant, et al., (2002) *Nature Biotech.* 20:999-1004); systems derived from Sindbis virus or Semliki forest virus (see Perri, et al, (2002) *J. Virol.* 74(20):9802-07); systems derived from Newcastle disease virus or Sendai virus.

In accordance with an example in which the codon-optimised nucleic acid encoding the functional PABPN1 protein as described herein is provided with a ddRNAi construct of the disclosure, the codon-optimised nucleic acid encoding the functional PABPN1 protein may be comprised within the same expression vector as the ddRNAi construct.

In an alternative example in which a codon-optimised nucleic acid encoding functional PABPN1 protein of the disclosure and a ddRNAi construct of the disclosure are to be provided together, the codon-optimised nucleic acid encoding functional PABPN1 protein and the ddRNAi construct may be comprised within different expression vectors. Where the codon-optimised nucleic acid encoding functional PABPN1 protein and the ddRNAi construct are comprised within different expression vectors, the respective expression vectors may be the same type of vector or be different types of vectors.

Testing for Functional PABPN1

Cell Culture Models

Exemplary cell culture models of OPMD have been described herein and are described in Example 3. Such cell culture models of OPMD may be used for assessing the ability of an agent of the disclosure to replace functional PABPN1 protein in the presence of one or more RNAs of the disclosure targeting endogenous PABPN1.

Exemplary methods of detecting the presence or absence or relative amount of PABPN1 protein have also been described and apply mutatis mutandis to this example. For example, the presence or absence or relative amount of PABPN1 protein may be detected using any one or more of Western blotting, ELISA, or other standard quantitative or semiquantitative techniques available in the art, or a combination of such techniques. Techniques relying on antibody recognition of PABPN1 are contemplated and are described herein (such as in Example 3). The mutant and functional PABPN1 proteins may be expressed with appropriate protein tags e.g., myc or flag tags, to facilitate differential detection of mutant and functional PABPN1 proteins using appropriate antibodies which are commercially available. For example, the mutant human PABPN1 protein may be expressed with a FLAG tag and comprise the amino acid sequence set forth in SEQ ID NO: 29. In this way, the presence or absence or relative amount of both mutant and functional PABPN1 protein may be detected independently in a cell following transfection or transduction of the cell with a RNA of the disclosure and an agent for replacing functional PABPN1 protein of the disclosure.

In one example, the presence or absence or relative abundance of PABPN1 polypeptide may be detected with techniques which comprise antibody capture of PABPN1 polypeptides in combination with electrophoretic resolution of captured PABPN1 polypeptides, for example using the Isonostic™ Assay (Target Discovery, Inc.). Antibodies are commercially available for PABPN1 protein.

An agent of the disclosure that expresses a PABPN1 protein which is not causative of OPMD in a cell in the presence of the RNA(s) of the disclosure (i.e., in the presence of a RNAi reagent described herein) is considered to be useful for treating OPMD.

Animal Models

Exemplary animal models for studying OPMD have been described. Exemplary animal models for studying OPMD are also described in Examples 4 and 5.

Any of the foregoing animal models can be used to determine the efficacy of an agent of the disclosure to replace functional PABPN1 protein in vivo in the presence a RNA or ddRNAi construct of the disclosure.

Methods for assaying intracellular and extracellular PABPN1 expression have been described herein with respect to cell models and shall be taken to apply mutatis mutandis to this example of the disclosure.

In one example, histological and morphological analyses described in Example 5 may be used to determine the efficacy of an agent of the disclosure to replace functional PABPN1 protein in vivo in the presence a RNA or ddRNAi construct of the disclosure. Further assays which may be used to determine efficacy of an agent of the disclosure to replace functional PABPN1 protein in vivo are described in Trollet et al., (2010) *Human Molecular Genetics,* 19(11): 2191-2207.

Compositions and Carriers

In some examples, a RNA or ddRNAi construct or expression vector of the disclosure is provided in a composition. In some examples, a nucleic acid encoding a functional PABPN1 protein of the disclosure is provided in a composition. In some example, a RNA or ddRNAi construct or expression vector of the disclosure is provided in a composition together with a nucleic acid encoding a functional PABPN1 protein of the disclosure.

As described herein, the expression vector may comprise a ddRNAi construct of the disclosure alone or in combination with a codon-optimised nucleic acid encoding the functional PABPN1 protein of the disclosure. Reference herein to an expression vector and/or a composition comprising same will therefore be understood to encompass: (i) an expression vector comprising a ddRNAi construct of the disclosure or a composition comprising same; (ii) an expression vector comprising a ddRNAi construct of the disclosure and a codon-optimised nucleic acid encoding the functional PABPN1 protein of the disclosure or a composition comprising same; or (iii) an expression vector comprising a codon-optimised nucleic acid encoding the functional PABPN1 protein of the disclosure or a composition comprising same.

According to one example, a composition of the disclosure may comprise (i) an expression vector comprising a ddRNAi construct of the disclosure, and (ii) an expression vector comprising a codon-optimised nucleic acid encoding the functional PABPN1 protein of the disclosure.

Alternatively, a composition of the disclosure may comprise an expression vector comprising ddRNAi construct of the disclosure and a codon-optimised nucleic acid encoding the functional PABPN1 protein of the disclosure.

In yet another example, an expression vector comprising a ddRNAi construct of the disclosure may be provided in one composition and an expression vector comprising a codon-optimised nucleic acid encoding the functional PABPN1 protein of the disclosure may be provided within another composition e.g., which are packaged together.

A composition of the disclosure may also comprise one or more pharmaceutically acceptable carriers or diluents. For example, the composition may comprise a carrier suitable for delivery of a RNA or ddRNAi construct or expression vector of the disclosure to muscle of a subject following administration thereto.

In some examples, the carrier is a lipid-based carrier, cationic lipid, or liposome nucleic acid complex, a liposome, a micelle, a virosome, a lipid nanoparticle or a mixture thereof.

In some examples, the carrier is a biodegradable polymer-based carrier, such that a cationic polymer-nucleic acid complex is formed. For example, the carrier may be a cationic polymer microparticle suitable for delivery of a RNA or ddRNAi construct or expression vector of the disclosure to muscle cells. Use of cationic polymers for delivery compositions to cells is known in the art, such as described in Judge et al. (2005) Nature 25: 457-462, the contents of which is incorporated herein by reference. An exemplary cationic polymer-based carrier is a cationic DNA binding polymer, such as polyethylenimine. Other cationic polymers suitable for complexing with, and delivery of, RNAs or ddRNAi constructs or expression vectors of the disclosure include poly(L-lysine) (PLL), chitosan, PAMAM dendrimers, and poly(2-dimethylamino)ethyl methacrylate (pDMAEMA) These are other suitable cationic polymers are known in the art and are described in Mastrobattista and Hennink, (2012) Nature Materials, 11:10-12, WO/2003/097107 and WO/2006/041617, the full contents of which are incorporated herein by reference. Such carrier formulations have been developed for various delivery routes including parenteral subcutaneous injection, intravenous injection and inhalation.

In a further example, the carrier is a cyclodextrin-based carrier such as a cyclodextrin polymer-nucleic acid complex.

In a further example, the carrier is a protein-based carrier such as a cationic peptide-nucleic acid complex.

In another example, the carrier is a lipid nanoparticle. Exemplary nanoparticles are described, for example, in U.S. Pat. No. 7,514,099.

In some examples, a RNA or ddRNAi or expression construct of the disclosure is formulated with a lipid nanoparticle composition comprising a cationic lipid/Cholesterol/PEG-C-DMA/DSPC (e.g., in a 40/48/2/10 ratio), a cationic lipid/Cholesterol/PEG-DMG/DSPC (e.g., in a 40/48/2/10 ratio), or a cationic lipid/Cholesterol/PEG-DMG (e.g., in a 60/38/2 ratio). In some examples, the cationic lipid is Octyl CL in DMA, DL in DMA, L-278, DLinKC2DMA, or MC3.

In another example, a RNA or ddRNAi or expression construct of the disclosure is formulated with any of the cationic lipid formulations described in WO 2010/021865; WO 2010/080724; WO 2010/042877; WO 2010/105209 or WO 2011/022460.

In another example, a RNA or ddRNAi or expression construct of the disclosure is conjugated to or complexed with another compound, e.g., to facilitate delivery of the RNA or ddRNAi or expression construct. Non-limiting, examples of such conjugates are described in US 2008/0152661 and US 2004/0162260 (e.g., CDM-LBA, CDM-Pip-LBA, CDM-PEG, CDM-NAG, etc.).

In another example, polyethylene glycol (PEG) is covalently attached to a RNA or ddRNAi or expression vector of the disclosure. The attached PEG can be any molecular weight, e.g., from about 100 to about 50,000 daltons (Da).

In yet other example, a RNA or ddRNAi construct or expression vector of the disclosure is formulated with a carrier comprising surface-modified liposomes containing poly(ethylene glycol) lipids (PEG-modified, or long-circulating liposomes or stealth liposomes), such as is disclosed in for example, WO 96/10391; WO 96/10390; or WO 96/10392.

In some examples, a RNA or ddRNAi construct or expression vector of the disclosure can also be formulated or complexed with polyethyleneimine or a derivative thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-tri-GAL) derivatives.

In other examples, a RNA or ddRNAi construct or expression vector of the disclosure is complexed with membrane disruptive agents such as those described in U.S. Patent Application Publication No. 2001/0007666.

Other carriers include cyclodextrins (see for example, Gonzalez et al., (1999), Bioconjugate Chem., 10, 1068-1074; or WO 03/46185), poly(lactic-co-glycolic)acid (PLGA) and PLCA microspheres (see for example US 2002130430).

Compositions will desirably include materials that increase the biological stability of the RNA or ddRNAi construct or expression vector of the disclosure and/or materials that increase the ability of the compositions to localise to and/or penetrate muscle cells selectively. The therapeutic compositions of the disclosure may be administered in pharmaceutically acceptable carriers (e.g., physiological saline), which are selected on the basis of the mode and route of administration, and standard pharmaceutical practice. One having ordinary skill in the art can readily formulate a pharmaceutical composition that comprises a RNA or ddRNAi construct or expression vector of the disclosure. In some cases, an isotonic formulation is used. Generally, additives for isotonicity can include sodium chloride, dextrose, mannitol, sorbitol and lactose. In some cases, isotonic solutions such as phosphate buffered saline are preferred. Stabilizers include gelatin and albumin. In some examples, a vasoconstriction agent is added to the formulation. The compositions according to the present disclosure are provided sterile and pyrogen free. Suitable pharmaceutical carriers, as well as pharmaceutical necessities for use in pharmaceutical formulations, are described in Remington:

The Science and Practice of Pharmacy (formerly Remington's Pharmaceutical Sciences), Mack Publishing Co., a standard reference text in this field, and in the USP/NF.

The volume, concentration, and formulation of the pharmaceutical composition, as well as the dosage regimen may be tailored specifically to maximize cellular delivery while minimizing toxicity such as an inflammatory response e.g, relatively large volumes (5, 10, 20, 50 ml or more) with corresponding low concentrations of active ingredients, as well as the inclusion of an anti-inflammatory compound such as a corticosteroid, may be utilized if desired.

Compositions of the disclosure may be formulated for administration by any suitable route. For example, routes of administration include, but are not limited to, intramuscular, intraperitoneal, intradermal, subcutaneous, intravenous, intraarterially, intraoccularly and oral as well as transdermal or by inhalation or suppository. Exemplary routes of administration include intravenous (IV), intramuscular (IM), oral, intraperitoneal, intradermal, intraarterial and subcutaneous injection. In one example, the composition of the disclosure is formulated for IM administration. Such compositions are useful for pharmaceutical applications and may readily be formulated in a suitable sterile, non-pyrogenic vehicle, e.g., buffered saline for injection, for parenteral administration e.g., IM, intravenously (including intravenous infusion), SC, and for intraperitoneal administration. Some routes of administration, such as IM, IV injection or infusion, may achieve effective delivery to muscle tissue and transfection of a ddRNAi constructs and/or codon-optimised nucleic acids encoding PABPN1 of the disclosure, and expression of RNA and/or the codon-optimised nucleic acid therein.

Methods of Treatment

In one example, a RNA or ddRNAi construct or expression vector or composition of the disclosure may be used for inhibiting expression of endogenous PABPN1 protein, including a PABPN1 protein which is causative of OPMD, in a subject.

In one example, a RNA or ddRNAi construct or expression vector or composition of the disclosure may be used to treat OPMD in a subject suffering therefrom. Similarly, a RNA or ddRNAi construct or expression vector or composition of the disclosure may be used to prevent the development or progression of one or more symptoms of OPMD in a subject suffering therefrom or predisposed thereto.

In each of the foregoing examples, the expression vector and/or composition of the disclosure may comprise both a ddRNAi construct of the disclosure and a codon-optimised nucleic acid encoding functional PABPN1 protein of the disclosure. Accordingly, administration of the expression vector or composition may be effective to (i) inhibit, reduce or knockdown expression of endogenous PABPN1, including the PABPN1 protein comprising an expanded polyalanine tract which is causative of OPMD, and (ii) provide for expression of a functional PABPN1 protein which is not targeted by RNAs which inhibit, reduce or knockdown expression of endogenous PABPN1. A composition of the disclosure may thus restore PABPN1 protein function e.g., post-transcriptional processing of RNA, in a cell or animal to which it is administered.

In another example, treatment of OPMD may comprise administering separately to a subject (i) one or more agents for inhibiting expression of a PABPN1 protein which is causative of OPMD, and (ii) an expression vector comprising a codon-optimised nucleic acid encoding functional PABPN1 protein of the disclosure or composition comprising same. As described herein, the one or more agents for inhibiting expression of a PABPN1 protein which is causative of OPMD may be a RNA or ddRNAi construct or expression vector or composition comprising of the disclosure. The subject may be administered components (i) and (ii) together, simultaneously or consecutively.

For example, treatment of OPMD may comprise administering to a subject a codon-optimised nucleic acid encoding a functional PABPN1 protein of the disclosure, wherein the subject has previously been administered one or more agents for inhibiting expression of a PABPN1 protein which is causative of OPMD but which does not inhibit expression of the codon-optimised nucleic acid. For example, the subject may have been previously administered a RNA, a plurality of RNAs, a ddRNAi construct, a plurality of ddRNAi constructs, an expression vector, a plurality of expression vectors and/or composition of the disclosure.

As discussed above, routes of administration include, but are not limited to, intramuscular, intraperitoneal, intradermal, subcutaneous, intravenous, intraarterially, intraoccularly and oral as well as transdermal or by inhalation or suppository. Exemplary routes of administration include intravenous (IV), intramuscular (IM), oral, intraperitoneal, intradermal, intraarterial and subcutaneous injection. Some routes of administration, such as IM, IV injection or infusion, may achieve effective delivery to muscle tissue and transfection of a ddRNAi constructs and/or codon-optimised nucleic acids encoding PABPN1 of the disclosure, and expression of RNA and/or the codon-optimised nucleic acid therein.

One skilled in the art would be able, by routine experimentation, to determine an effective, non-toxic amount of a RNA or ddRNAi construct or expression vector(s) or composition(s) of the disclosure which would be required to treat a subject suffering from OPMD. The therapeutically effective dose level for any particular patient will depend upon a variety of factors including: the composition employed; the age, body weight, general health, sex and diet of the patient; the time of administration; the route of administration; the rate of sequestration of the RNA or ddRNAi construct or expression vector(s) or composition(s) of the disclosure; the duration of the treatment, together with other related factors well known in medicine.

Efficacy of a RNA or ddRNAi construct or expression vector(s) or composition(s) of the disclosure to reduce or inhibit expression of the PABPN1 protein causative of OPMD and to express functional PABPN1 protein which is not causative of OPMD in an amount sufficient to restore PABPN1 function, may be determined by evaluating muscle contractile properties and/or swallowing difficulties in the subject treated. Methods for testing swallowing ability and muscle contractile properties are known in the art. For example, swallowing difficulties may be evaluated using videofluoroscopy, UGI endoscopy or oesophageal manometry and impedance testing. Other methods for assessing clinical features of OPMD are described in Rüegg et al., (2005) *Swiss Medical Weekly*, 135:574-586.

Kits

The present disclosure also provides a RNA or a ddRNAi construct or expression vector(s) or composition(s) of the disclosure in a kit. The kit may comprise a container. The kit typically contains a RNA or a ddRNAi construct or expression vector(s) or composition(s) of the disclosure with instructions for its administration. In some examples, the kit contains more than one RNA or ddRNAi or expression vector or composition of the disclosure. In one example, the kit comprises (i) a RNA or a ddRNAi construct or expression vector(s) or composition(s) of the disclosure as first kit component, and (ii) an expression vector comprising a codon-optimised nucleic acid encoding the functional PABPN1 protein of the disclosure or composition comprising same as a second kit component. The first and second kit components may be packaged together in a kit.

TABLE 1

Target regions within PABPN1 mRNA transcript

| Region ID | Region sequence (5' - 3') | SEQ ID NO: |
|---|---|---|
| Region 1 | UUGAGGAGAAGAUGGAGGCUGAU | SEQ ID NO: 1 |
| Region 2 | AGGAAGAAGCUGAGAAGCUAA | SEQ ID NO: 2 |
| Region 3 | GAGGUAGAGAAGCAGAUGAAUAUGAGU | SEQ ID NO: 3 |

TABLE 2 ssRNAs

| ssRNA ID | Effector sequence (5' - 3') | SEQ ID NO: |
|---|---|---|
| ssRNA1 | AUCAGCCUCCAUCUUCUCCUCAA | SEQ ID NO: 4 |
| ssRNA2 | UUAGCUUCUCAGCUUCUUCCU | SEQ ID NO: 6 |
| ssRNA3 | ACUCAUAUUCAUCUGCUUCUCUACCUC | SEQ ID NO: 8 |

TABLE 3 dsRNA duplexes

| dsRNA ID | Effector (5' - 3') | SEQ ID NO: | Effector complement (5' - 3') | SEQ ID NO: |
|---|---|---|---|---|
| dsRNA1 | AUCAGCCUCCAUCUUCUCCUCAA | SEQ ID NO: 4 | UUGAGGAGAAGAUGGAGGCUGAU | SEQ ID NO: 5 |
| dsRNA2 | UUAGCUUCUCAGCUUCUUCCU | SEQ ID NO: 6 | AGGAAGAAGCUGAGAAGCUAA | SEQ ID NO: 7 |
| dsRNA3 | ACUCAUAUUCAUCUGCUUCUCUACCUC | SEQ ID NO: 8 | GAGGUAGAGAAGCAGAUGAAUAUGAGU | SEQ ID NO: 9 |
| shRNA1 | AUCAGCCUCCAUCUUCUCCUCAA | SEQ ID NO: 10 | UUGAGGAGAAGAUGGAGGCUGAU | SEQ ID NO: 11 |
| shRNA2 | UUAGCUUCUCAGCUUCUUCCU | SEQ ID NO: 12 | AGGAAGAAGCUGAGAAGCUAA | SEQ ID NO: 13 |
| shRNA3 | ACUCAUAUUCAUCUGCUUCUCUACCUC | SEQ ID NO: 14 | GAGGUAGAGAAGCAGAUGAAUAUGAGU | SEQ ID NO: 15 |

TABLE 5 shRNAs

| shRNA ID | shRNA sequence (5' - 3') | SEQ ID NO: |
|---|---|---|
| shRNA1 | GAGGAGAAGAUGGAGGCUGAUCAAGAGAAUCAGCCUCCAUCUUCUCCUC | SEQ ID NO: 16 |
| shRNA2 | AUCAGCCUCCAUCUUCUCCUCCAAGAGAGGAGAAGAUGGAGGCUGAU | SEQ ID NO: 17 |
| shRNA3 | GGAAGAAGCUGAGAAGCUAACAAGAGAUUAGCUUCUCAGCUUCUUCC | SEQ ID NO: 18 |
| shRNA4 | UUAGCUUCUCAGCUUCUUCCCAAGAGAGGAAGAAGCUGAGAAGCUAA | SEQ ID NO: 19 |
| shRNA5 | GAGGUAGAGAAGCAGAUGAAUAUGAGUUCAAGAGACUCAUAUUCAUCUGCUUCUCUACCUC | SEQ ID NO: 20 |

TABLE 5-continued shRNAs

| shRNA ID | shRNA sequence (5' - 3') | SEQ ID NO: |
|---|---|---|
| shRNA6 | CUCAUAUUCAUCUGCUUCUCUACCUCCAAGAGAGGUAGAGAAGCAGAUGAAUAUGAGU | SEQ ID NO: 21 |

EXAMPLES

Example 1—Design of dsRNAs and shRNAs Targeting PABPN1

Sequences representing potential targets for design of ddRNAi constructs were identified from the PABPN1 mRNA sequence using publicly available siRNA design algorithms (including Ambion, Promega, Invitrogen, Origene and MWG): sequences were chosen which were conserved in the human, bovine and mouse. siRNAs were synthesised and tested in vitro on these and three active siRNAs were selected for conversion to ddRNAi constructs. The mRNA transcripts corresponding to regions chosen as targets for design of double-stranded RNAs (dsRNAs) and short hairpin RNAs (shRNA) are presented in Table 1.

dsRNAs comprising effector sequences substantially complementary to the target regions described in Table 1 were designed and validated (Table 3). Screening of siRNA sequences to downregulate human PABPN1 was performed in HeLa cells where endogenous human PABPN1 is constitutively expressed. Transfection of siRNA was carried out using Oligofectamine (Life Technologies). Briefly, on the day of transfection, the media in 12 wells plate was replaced with 400 µl of serum-free media without antibiotic and 100 µl of Oligofectamine-siRNA complex. In 100 µl of Oligofectamine-siRNA complex, 3 µl of Oligofectamine in 7 µl of Opti-Mem (Gibco) and 60 pmol siRNA in 87 µl of Opti-Mem were mixed together for a final volume of 100 µl. The mixture was incubated at room temperature for 20 min. 4 hours after transfection, 250 µl of medium with 30% FBS was added in each well. The final siRNA concentration was 80 nM. RNA extraction was performed 48 hours after transfection. All the siRNA sequences tested against the target regions set forth in Table 1 showed a substantial knock down of PABPN1 in HeLa cells. Of the siRNAs tested, three sequences showing different degree of efficacy (dsRNAs 1, 2 and 3 in Table 3). These were also evaluated in human myoblasts from healthy or OPMD affected individuals.

Briefly, human myoblasts from healthy or OPMD affected individuals were transfected with dsRNA1, dsRNA 2 or dsRNA3 in accordance with the method described above. Quantitative RT-PCR was then performed and showed significant level of knock down for each of the dsRNAs (FIG. 1).

shRNAs corresponding to dsRNA 1-3 comprising effector sequences which are substantially complementary to the target regions described in Table 1 were designed and are presented in Table 4. Complete sequences for the shRNAs in Table 4, inclusive of effector sequences, stem loop sequences and effector complement sequences respectively (5'-3' orientation), are presented in Table 5.

Example 2—Generation of Self-Complementary AAV-Based Plasmid Constructs and Viruses Expressing shRNAs Targeting PABPN1

Self-complementary adeno-associated virus type 2 (scAAV2) plasmids expressing one or three of the shRNAs targeting PABPN1 (as presented in Table 5) were generated by subcloning a single or three shRNAs targeting PABPN1 into a scAAV2 backbone.

Briefly, a single shRNA construct comprising DNA coding shRNA5 (SEQ ID NO: 20) under control of a H1 promoter was cloned into a pAAV2 vector backbone (pAAV-shRNA5). Two triple shRNA constructs were also produced comprising DNA coding for shRNA1 (SEQ ID NO: 16), shRNA3 (SEQ ID NO: 18) and shRNA5 (SEQ ID NO: 20) under control of RNA polymerase III promoters U61, U69 and H1, respectively, cloned into a pAAV2 vector backbone. These triple constructs were pAAV-shRNAx3-short (SEQ ID NO: 22) and pAAV-shRNAx3-long (SEQ ID NO: 23). Both variants included the tricistronic shRNA construct described, however, the construct in pAAV-shRNAx3-long also included a stuffer DNA sequence to create an optimal insert size for AAV packaging. Similarly, an AAV viral plasmid expressing shRNA against HBV polymerase gene (pAAV-HBVpol) was constructed for use as a control.

A further two plasmids were produced, one coding for a FLAG-tagged mutant human PABPN1 including the 7 alanine-expansion (pAAV mut-PABPN1-FLAG; SEQ ID NO: 27), and the other comprising codon-optimised sequence coding for wild-type human PABPN1 with a MYC tag (pAAV Opt-hPABPN1-MYC; SEQ ID NO: 26).

Each of the AAV vectors were produced by pseudotyping in AAV8 capsid.

Recombinant pseudotyped AAV vector stocks were then generated. Briefly, HEK293T cells were cultured in roller bottles in Dulbecco's modified Eagle's medium, supplemented with 10% FBS, and incubated at 37° C. and 5% $CO_2$. Each of the pAAV-shRNA viral plasmids described in this example and a pAAVhelpercap8 plasmid (pDP8r) or pAAVhelpercap9 plasmid (pDP9rs) were complexed with polyethyleneimine (PEI) according to the manufacturer's instructions. Double-transfections were then performed with one of pAAV-shRNA5, pAAV-shRNAx3-short or pAAV-shRNAx3-long and pDP8r (or pDP9rs) in the HEK293T cells. The HEK293T cells were cultured for a period of 72 hours at 37° C. and 5% $CO_2$, after which time the cells were lysed and scAAV shRNA-expressing particles for each of the viral plasmids were purified by iodixanol (Sigma-Aldrich) step-gradient ultracentrifugation. The number of vector genomes was quantified by dot blot hybridization and quantitative polymerase chain reaction (Q-PCR).

For viral plasmids designated pAAV-shRNA5, pAAV-shRNAx3-short, pAAV-shRNAx3-long, pAAV-HBVpol, pAAV mut-PABPN1-FLAG and pAAV Opt-hPABPN1-MYC, the corresponding scAAV8 viral preparations were designated scAAV8-shRNA5, scAAV8-shRNAx3-short, scAAV8-shRNAx3-long, scAAV8-HBVpol, ssAAV8 mut-PABPN1-FLAG and ssAAV9-Opt-hPABPN1-MYC, respectively.

Example 3—Gene Silencing of PABPN1 In Vitro

This example demonstrates the ability of the PABPN1 pAAV-shRNA plasmids produced in Example 2 to knockdown expression of PABPN1 in vitro.

Cells

Human embryonic kidney cells (HEK293T, ATCC, Manassas, USA) were grown in Dulbecco's modified Eagle's medium (DMEM) containing 20 mM HEPES, 10% foetal bovine serum (FBS) and 2 mM glutamine (PAA laboratories, Yeovil, UK).

Primary mouse myoblasts (clone IM2) immortalised with a temperature-sensitive SV40 large T-antigen (tsA58) transgene and derived from the Immorto-Mouse H2kB-IM2 (parental cell line), H2kB-WTA (coding for human wild type PABPN1) and H2kB-D7e (coding for 7 alanine-expanded PABPN1) were provided by Dr Michael Antoniou, King's College London. The IM2 cells were grown in DMEM containing 20 mM HEPES, 2 mM glutamine and supplemented with 20% FBS, 0.5% chicken embryo extract, 100 U/ml penicillin-streptomycin, 2 mmol/L L-glutamine and 20 U/ml interferon-γ.

Treatment

Briefly, HEK293T cells were seeded at $3\times10^5$ cells/well and transfected the next day with one of pAAV-shRNA5, pAAV-shRNAx3-short or pAAV-shRNAx3-long (4 μg/well), with or without AAV plasmids expressing mutant hPABPN1-FLAG (pAAV mut-PABPN1-FLAG) (4 μg/well) (SEQ ID NO: 27) or codon-optimised PABPN1 (pAAV Opt-hPABPN1-MYC) (4 μg/well) (SEQ ID NO: 26). As a control, HEK293T cells were transfected with the pAAV-HBVpol plasmid expressing shRNA against the HBV polymerase gene (4 μg/well). The HEK293T cells were incubated at 33° C. in DMEM 10% FCS in the absence of antibiotics for 48 hours, after which time the cells were harvested and cell lysates produced for analysis by western blotting.

Similarly, H2kB-D7e mouse myoblasts ($10^6$ cells/well) were transfected by nucleofection with pAAV-HBVpol, AAV-shRNAx3-short or pAAV-shRNAx3-long, with or without AAV plasmids expressing mutant hPABPN1-FLAG or Opt-hPABPN1-MYC (1 μg/well). The H2kB-D7e mouse myoblasts were then incubated at 33° C. in DMEM 10% FCS in the absence of antibiotics for 48 hours and then switched to differentiation by incubation in DMEM/5% horse serum for a further 72 hours. 5 days post-transfection, myotubes were harvested and cell lysates produced for analysis by western blotting.

Western Blot Analysis

Cell lysates were prepared by homogenising cells in RIPA buffer containing: NaCl 0.15M, 0.1% SDS, 50 mM Tris (pH8), 2 mM EDTA and 10% Triton-X-100 with protease inhibitor cocktail (Complete, Roche Diagnostics).

Proteins were separated on 4-12% Bis-Tris gel (Invitrogen) and transferred onto a nitrocellulose membrane (Hybond ECL membrane; Amersham Biosciences), which was blocked by incubation in 5% milk in 0.1M PBS, 0.1% Tween-20. The nitrocellulose membrane was stained with primary antibodies raised against PABPN1 (abcam, 1/10,000) and human GAPDH (abcam, 1/10,000) or mouse GAPDH (abcam, 1/2500) as a house-keeping control.

To detect the expanded mutant PABPN1 protein expressed by the pAAV mut-PABPN1-FLAG vector and the codon-optimised PABPN1 protein expressed by the pAAV opt-hPABPN1-MYC vector, the nitrocellulose membrane was stained with anti-FLAG antibody (Sigma, 1/10,000) and an anti-cMYC antibody (Abcam, 1/10,000), respectively.

The nitrocellulose membrane was further incubated with HRP-conjugated anti-rabbit and anti-mouse secondary antibodies (Sigma, 1/2000 and 1/1000, respectively). Immunoreactive bands were detected with enhanced chemiluminescencereagent (ECL; Amersham Biosciences) and visualised by exposing the membrane to ECL Hyperfilm (Amersham Biosciences).

Figure 2:
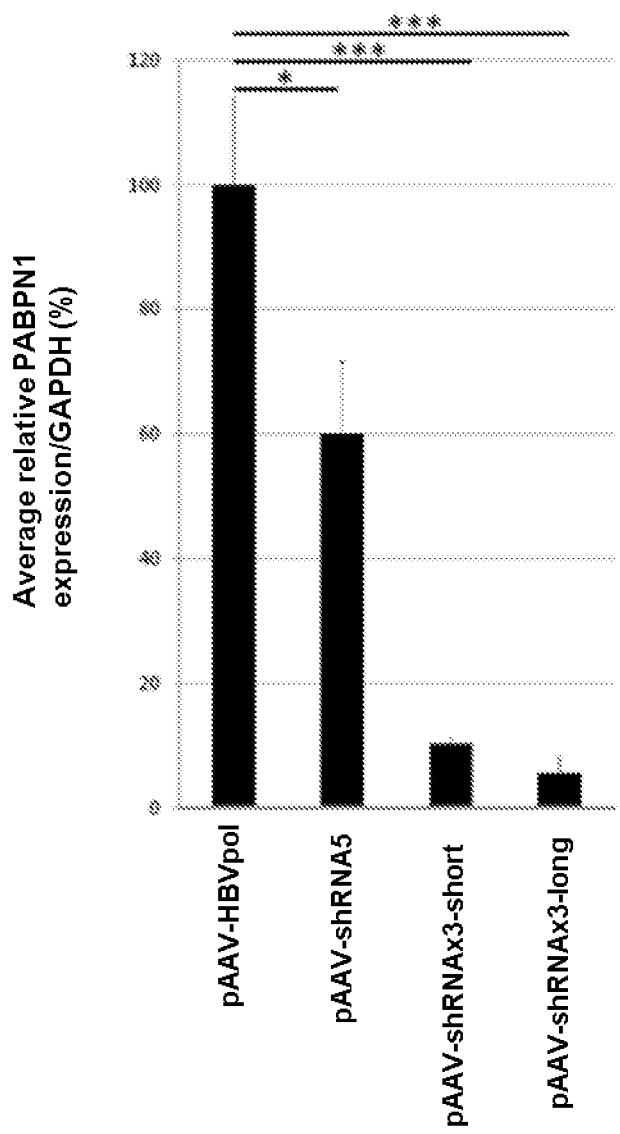
FIG. 2 illustrates PABPN1 knockdown efficiency in HEK293T cells following transfection with AAV plasmids expressing single and tricistronic shRNA(s) against PABPN1 mRNA. PABPN1 expression expressed relative to GAPDH expression ($*p<0.05$, $***p<0.005$).

Quantification of total knockdown for PABPN1 relative to GAPDH using ImageJ is shown in FIG. 2. As is apparent from FIG. 2, averages of 40%, 90% and 95% knockdown of PABPN1 expression were achieved with the single shRNA vector (pAAV-shRNA5), the tricitronic-short vector (pAAV-shRNAx3-short) and the tricitronic-long vector (pAAV-shRNAx3-long) respectively. Both the short (~1 Kb insert size) and long (~1.5 kb insert size) tricitronic shRNA constructs resulted in a similar extent of PABPN1 knockdown, due to a similarity in sequence compositions directed against the same targets within the PABPN1 gene. In this regard, the addition of the stuffer sequence to the pAAV-shRNAx3-long construct did not adversely affect PABPN1 knockdown efficiency, but rather resulted in slightly higher knockdown.

Figure 3:
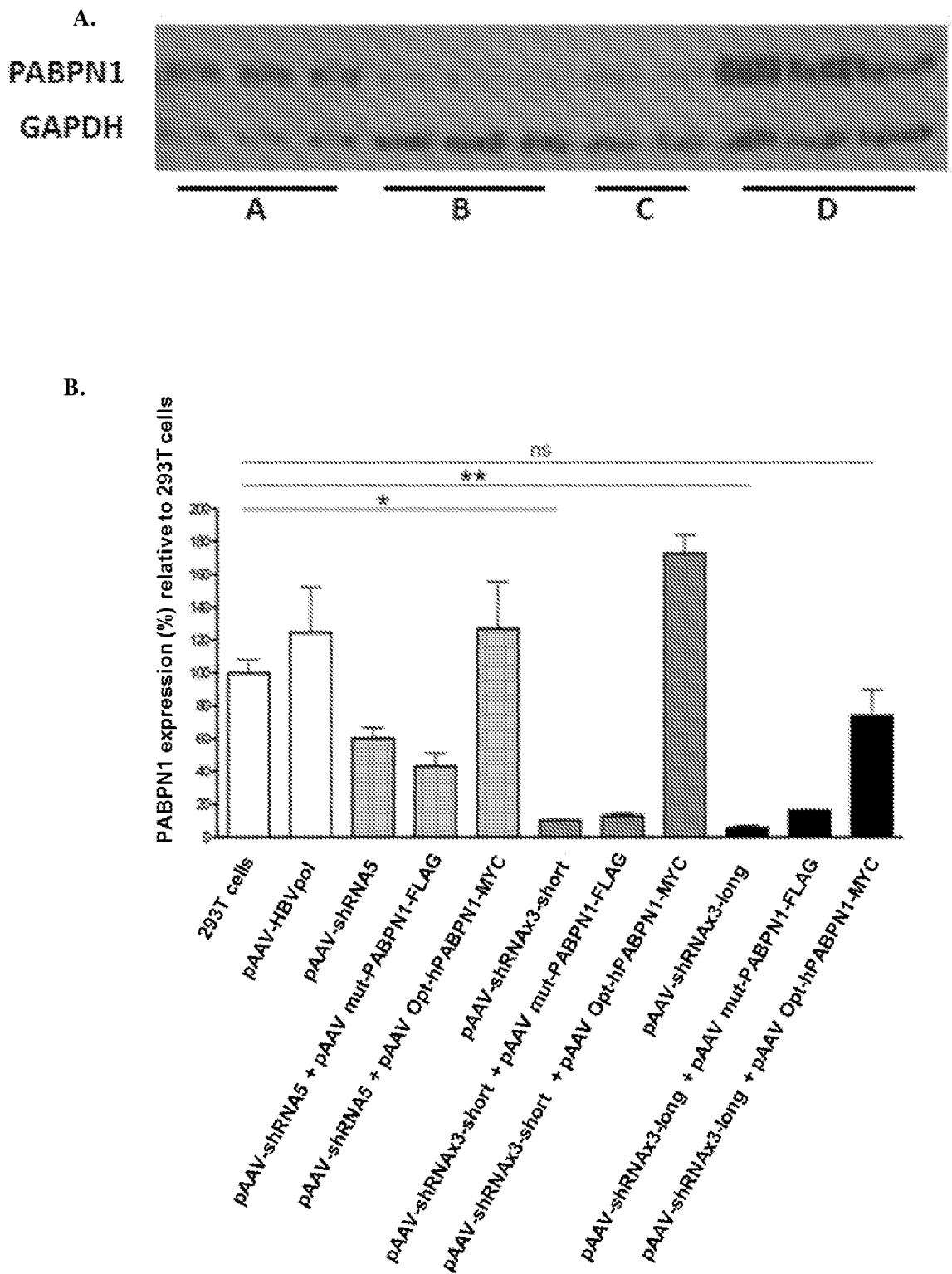
FIG. 3(A) is a western blot showing the level of PABPN1 protein relative to GAPDH protein expressed in HEK293T cells transfected with (A) pAAV-HBVpol, (B) pAAV-shRNAx3-long, (C) pAAV mut-PABPN1-FLAG, or (D) pAAV Opt-hPABPN1-MYC.
FIG. 3(B) illustrates, from left to right, average PABPN1 expression normalised to PABPN1 expression in untransfected HEK293T cells in (i) untransfected control HEK293T cells, (ii) HEK293T cells transfected with pAAV-HBVpol, (iii) HEK293T cells transfected with pAAV-shRNA5, (iv) HEK293T cells transfected with pAAV-shRNA5 and pAAV mut-PABPN1-FLAG, (v) HEK293T cells transfected with pAAV-shRNA5 and pAAV Opt-hPABPN1-MYC, (vi) HEK293T cells transfected with pAAV-shRNAx3-short, (vii) HEK293T cells transfected with pAAV-shRNAx3-short and pAAV mut-PABPN1-FLAG, (viii) HEK293T cells transfected with pAAV-shRNAx3-short and pAAV Opt-hPABPN1-MYC, (ix) HEK293T cells transfected with pAAV-shRNAx3-long, (x) HEK293T cells transfected with pAAV-shRNAx3-long and pAAV mut-PABPN1-FLAG, and (xi) HEK293T cells transfected with pAAV-shRNAx3-long and pAAV Opt-hPABPN1-MYC (p<0.01, *p<0.005).
FIG. 3(C) is a western blot showing levels of Myc-tagged PABPN1 protein relative to GAPDH protein expressed in HEK293T cells transfected with, from left to right, (i) pAAV-HBVpol, (ii) pAAV mut-PABPN1-FLAG and pAAV-HBVpol, (iii) pAAV Opt-hPABPN1-MYC and pAAV-HBVpol, (iv) pAAV-shRNAx3-long, (v) pAAV mut-PABPN1-FLAG and pAAV-shRNAx3-long, or (vi) pAAV Opt-hPABPN1-MYC and pAAV-shRNAx3-long.
Figure 3:
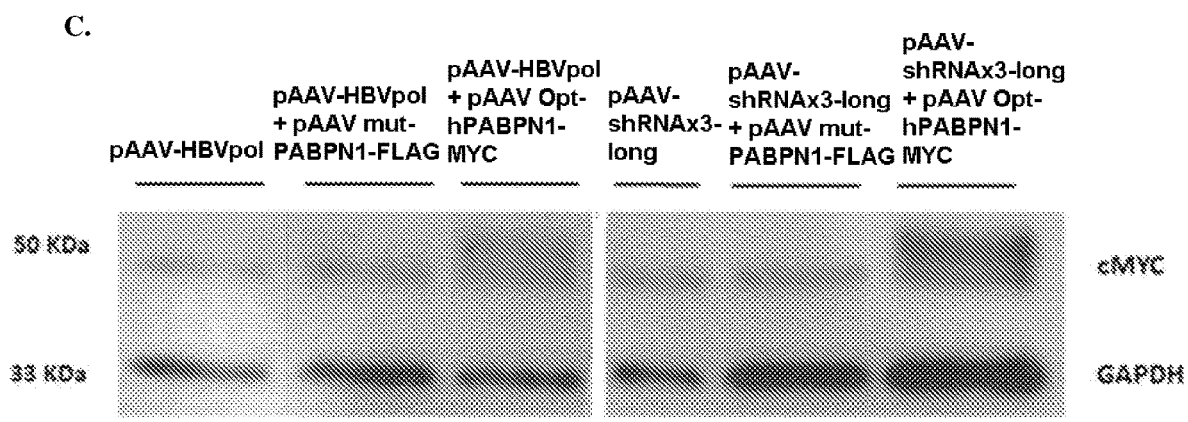
Figure 4:
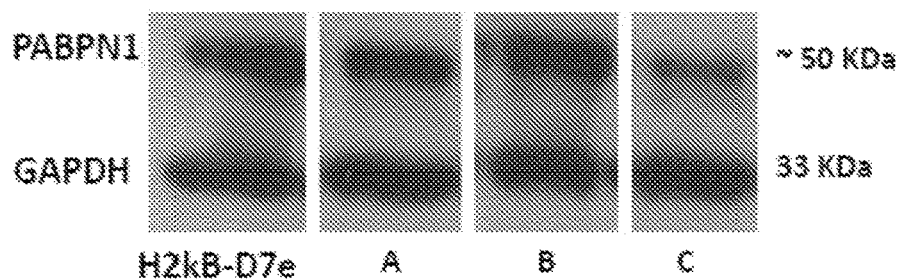
FIG. 4(A) is a western blot showing levels of PABPN1 protein relative to GAPDH protein in control H2kB-D7e cells and in H2kB-D7e cells transfected with (A) pAAV-HBVpol, (B) pAAV-shRNAx3-long or (C) pAAV mut-PABPN1-FLAG and pAAV-shRNAx3-long.
FIG. 4(B) is a western blot showing levels of Myc-tagged PABPN1 protein relative to GAPDH protein in H2kB-D7e cells transfected with (B) pAAV-shRNAx3-long, (D) pAAV Opt-hPABPN1-MYC and pAAV-shRNAx3-long, (A) pAAV-HBVpol, or (C) pAAV mut-PABPN1-FLAG and pAAV-shRNAx3-long.
FIG. 4(C) illustrates the average level of Myc-tagged codon-optimised PABPN1 expression relative to GAPDH expression (expressed as a percentage) in H2kB-D7e cells transfected with (i) pAAV Opt-hPABPN1-MYC, (ii) pAAV-HBVpol, (iii) pAAV-shRNAx3-long, and (iv) pAAV-shRNAx3-long and pAAV Opt-hPABPN1-MYC.
FIG. 4(D) is a western blot showing the level of FLAG-tagged mutant PABPN1 protein (comprising an expanded polyalanine tract) relative to GAPDH protein in H2kB-D7e cells transfected with (A) pAAV-HBVpol, (C) pAAV mut-PABPN1-FLAG, and pAAV-shRNAx3-long, (B) pAAV-shRNAx3-long, or (D) pAAV Opt-hPABPN1-MYC and pAAV-shRNAx3-long.
FIG. 4(E) illustrates the average level of FLAG-tagged mutant PABPN1 protein (comprising an expanded polyalanine tract) relative to GAPDH expression (expressed as a percentage) in H2kB-D7e cells transfected with, from left to right, (A) pAAV-HBVpol, (B) pAAV-shRNAx3-long, (C) pAAV-shRNAx3-long, or (D) pAAV-shRNAx3-long and pAAV-shRNAx3-long.
Figure 4:
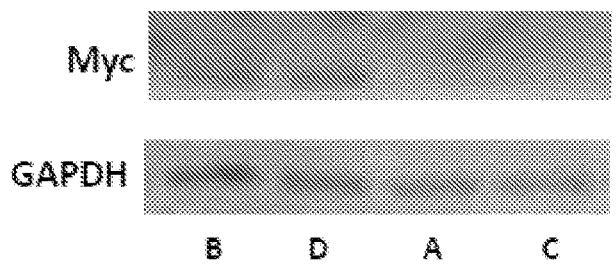
Figure 4:
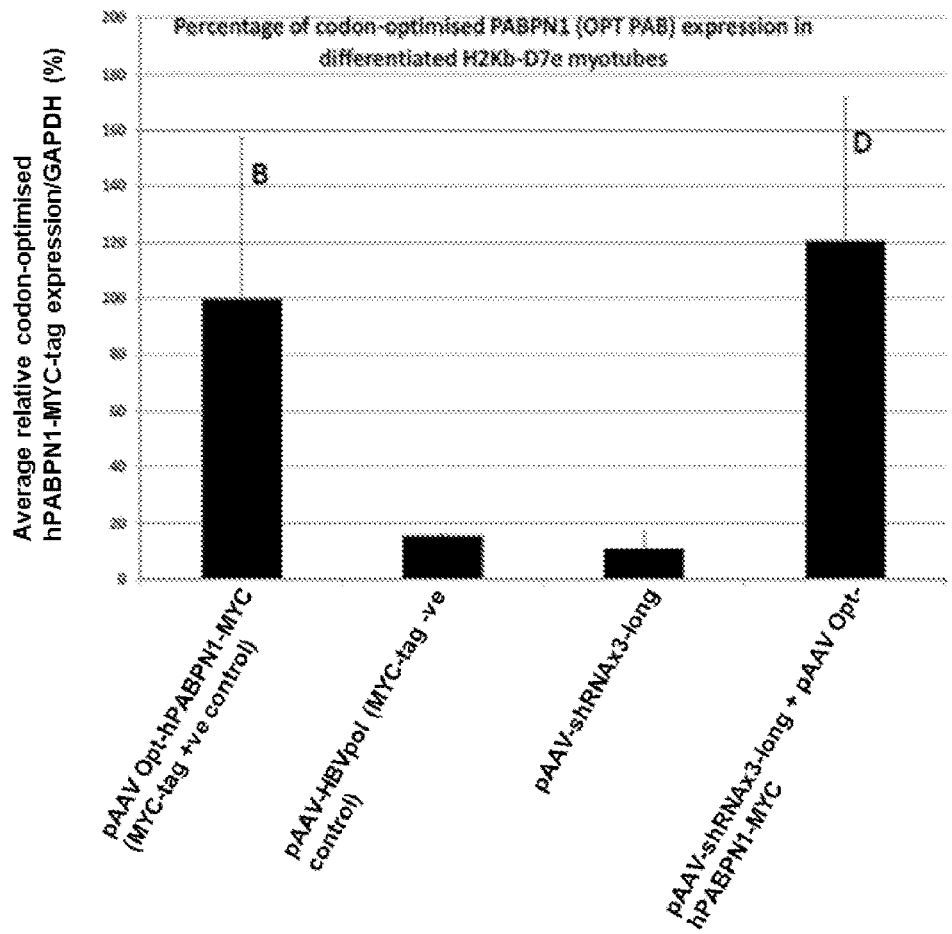
Figure 4:
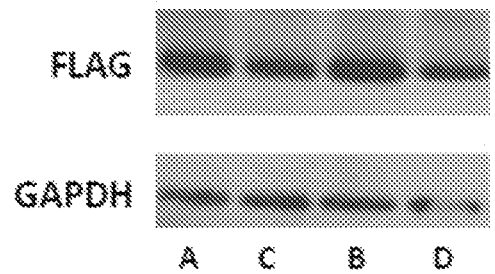
Figure 4:
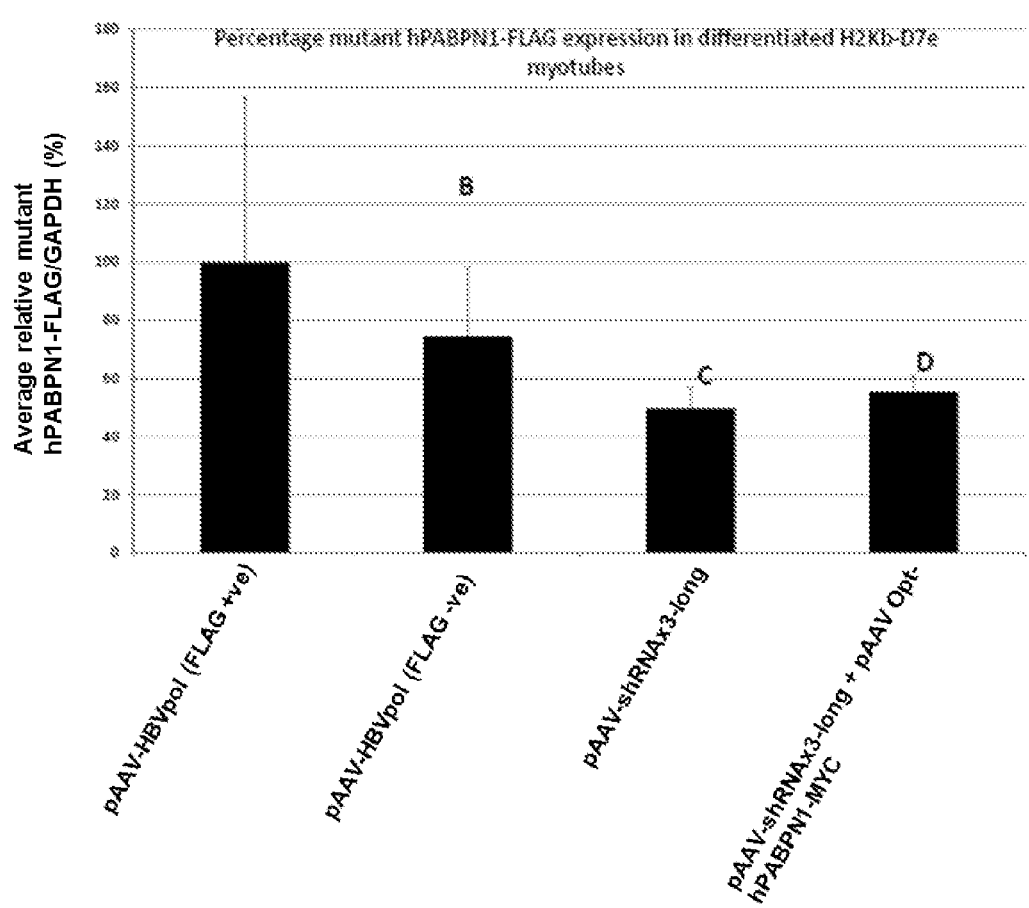

The single shRNA vector (pAAV-shRNA5) and both tricitronic vectors (pAAV-shRNAx3-short and pAAV-shRNAx3-long) were able to knock-down wild type and mutant PABPN1 in HEK293 cells co-transfected with pAAV mut-PABPN1-FLAG expressing mutant PABPN1, but the overall knock-down was more statistically significant for the triple shRNA constructs than it was for the single shRNA construct. On the other hand, no knock-down was observed in HEK293 cells co-transfected with the pAAV mut-PABPN1-FLAG vector expressing mutant PABPN1 and the pAAV-HBV-pol control vector targeting the HBV polymerase gene (FIGS. 3a and 3b).

Furthermore, compared with HEK293 cells co-transfected with the pAAV mut-PABPN1-FLAG vector expressing expanded mutant PABPN1 protein, cells co-transfected with the pAAV Opt-hPABPN1-MYC vector expressing codon-optimised PABPN1 showed good levels of PABPN1 protein. These data demonstrate that the codon-optimised PABPN1 protein is resistance to degradation by shRNAs expressed by the single and tricitronic shRNA constructs (FIGS. 3a and 3b). In order to confirm this observation, a cMYC antibody was used to detect expression of codon-optimised PABPN1 protein comprising cMYC peptide tag (FIG. 3c).

Similar results were obtained in H2kB-D7e mouse myoblasts transfected with either (i) the pAAV-HBV-pol control vector, (ii) pAAV Opt-hPABPN1-MYC vector expressing codon-optimised PABPN1, (iii) pAAV-shRNAx3-long vector, or (iv) pAAV Opt-hPABPN1-MYC vector and pAAV-shRNAx3-long vector. As is apparent from FIGS. 4a-4e, the pAAV-shRNAx3-long vector was able to knock-down mutant expanded PABPN1 protein expressed by the differentiated H2kB-D7e mouse myoblasts, whereas the codon-optimised PABPN1 protein was resistant to degradation by shRNAs expressed by the tricistronic shRNA construct.

All data are presented as mean values±standard error of the mean. All statistical analyses were performed using the Student t-test or ANOVA. A difference was considered to be significant at *P<0.05, P<0.01 or *P<0.001.

Based on these data, the pAAV8-shRNAx3-long construct was taken forward for virus production and further assessment.

Example 4—Gene Silencing of Endogenous PABPN1 and Replacement with Codon Optimised PABPN1 In Vivo This example demonstrates the ability of the scAAV8-shRNAx3-long recombinant virus produced in Example 2 to knockdown expression of endogenous PABPN1 in vivo and its replacement with a codon optimised human PABPN1. The physiological consequences of knockdown of mutant PABPN1 and replacement with a non-mutated form of the gene are also demonstrated.

Treatment

A17.1 transgenic mice have previously been described (Davies, Wang et al., 2005, Trollet, Anvar et al., 2010). A17.1 mice and WT FvB controls were generated by crossing the heterozygous carrier strain A17.1 (Davies, Wang et al., 2005) with the FvB background mice. Mice were genotyped for bovine PABPN1 4 weeks after birth and were housed in minimal disease facilities (Royal Holloway-University of London) with food and water ad libitum.

Briefly, 10-12 week-old A17 mice were placed in treatment groups 1-4 below (n=5 per treatment group). WT FvB mice, also 10-12 weeks old, were used as healthy controls and placed in group 5 (n=5). All mice were anesthetised with 2-4% isoflurane and treated as follows:

Group 1 (A17): a single 50 µl bolus of physiological saline containing 2.5E+10 scAAV8-shRNAx3-long viral particles to both TA muscles by IM injection.

Group 2 (A17): a single 50 µl bolus of physiological saline containing 1.3E+11 ssAAV9-Opt-hPABPN1 viral particles (expressing codon-optimised hPABPN1) to both TA muscles by IM injection.

Group 3 (A17): a single 50 µl bolus of physiological saline containing 2.5E+10 scAAV8-shRNAx3-long viral particles and 1.3E+11 ssAAV9-Opt-hPABPN1 viral particles to both TA muscles by IM injection.

Group 4 (A17): a single 50 µl bolus of physiological saline only.

Group 5 (FvB): a single 50 µl bolus of physiological saline only.

Muscle Contractile Properties

Measurements of TA muscle contractile properties, including isometric maximal and specific force, were performed 18 weeks post-injection using the methodology described previously in Trollet et al., (2010) *Human Molecular Genetics*, 19(11): 2191-2207. These data are presented in FIG. 4.

Mice were then sacrificed by overdose of anaesthetic, after which time the TA muscles were excised from tendon-to-tendon, weighed and rapidly frozen in liquid nitrogen-cooled isopentane for further histological and molecular analysis.

PABPN1 mRNA Expression

Total RNA was extracted from skeletal muscles samples using Trizol (Invitrogen) according to the manufacturer's instructions. RNA samples were quantified using a ND-1000 NanoDrop spectrophotometer (NanoDrop Technologies). RNA (50-250 ng for muscle biopsies, 1-3 µg for cell pellet) was reverse transcribed using M-MLV reverse transcriptase (Invitrogen) according to the manufacturer's instructions. cDNA was used for quantitative PCR reaction using SYBR green mix buffer (LightCycler® 480 Sybr green I Master) in a total of 9 ul reaction volume. PCR reaction was carried out as follows: 8 minutes at 95° C. followed by 50 cycles: 15 seconds at 95° C., 15 seconds at 60° C. and 15 seconds at 72° C. Specificity of the PCR products was checked by melting curve analysis using the following program: 65° C. increasing by 0.11° C./second to 97° C.

The expression level of each mRNA was normalized to that of murine RPLP0 mRNA (large ribosomal protein, subunit P0) expression. Expression levels were calculated according to the ΔΔCt method.

The sequences of primers used for RT-PCR and for Real-time RT-PCR are as follows:

```
PABPN1-FWD
5'-TGACCCGGGGGACGGCGC-3'

PABPN1-REV
5'-ACTCGAGCTTTGATAGCTTCCAGC-3'

RPLP0-FWD
5'-GAGGACCTCACTGAGATTCGG-3'

PRLP0-REV
5'-TTCTGAGCTGGCACAGTGAC-3'
```

Immunohistochemistry

Immunohistochemistry was performed on sections of TA muscle (10 µm) excised from mice to detect the presence of nuclear aggregates of PABPN1 protein. Briefly, sections of TA muscle were incubated in 1M KCl, 30 mM HEPES, 65 mM PIPES, 10 mM EDTA, 2 mM $MgCl_2$ (pH 6.9) for 1 hour to remove any soluble proteins. Sections were then blocked with 1% normal goat serum in 0.1M PBS, 0.1% Triton X100 and incubated overnight at 4° C. with anti-PABPN1 primary antibody, diluted to 1:200 in the same buffer. Sections were then further incubated with an Antibody for Laminin for 1 h RT and then with secondary antibodies for 1 h at room temperature. Finally sections were stained with Hoechst to visualize nuclei.

Histological and Morphological Analyses

Figure 5:
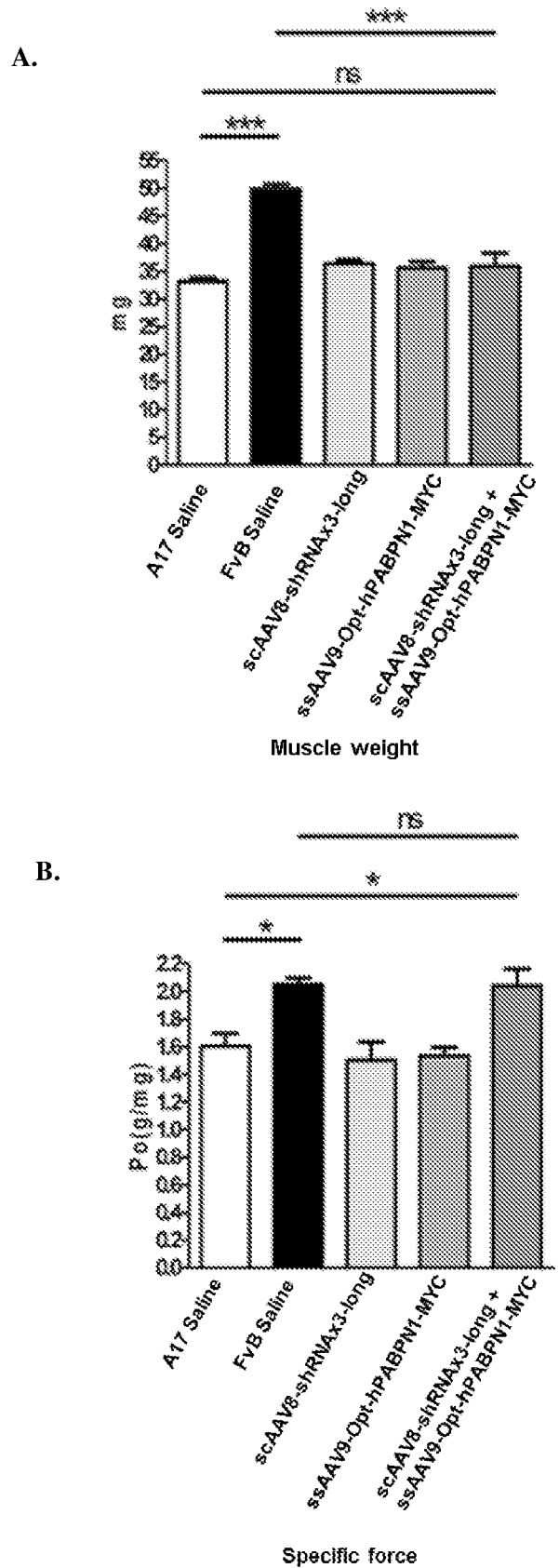
FIG. 5 shows (A) weight, (B) specific force, and (C) isometric maximal force, of Tibialis anterior (TA) muscles excised from (i) A17 mice treated with saline, (ii) FvB mice treated with saline, (iii) A17 treated with scAAV8-shRNAx3-long, (iv) A17 treated with ssAAV9 Opt-hPABPN1-MYC and (v) A17 treated with scAAV8-shRNAx3-long and ssAAV9 Opt-hPABPN1-MYC. All muscle measurement were taken 18 weeks post-injection.
Figure 5:
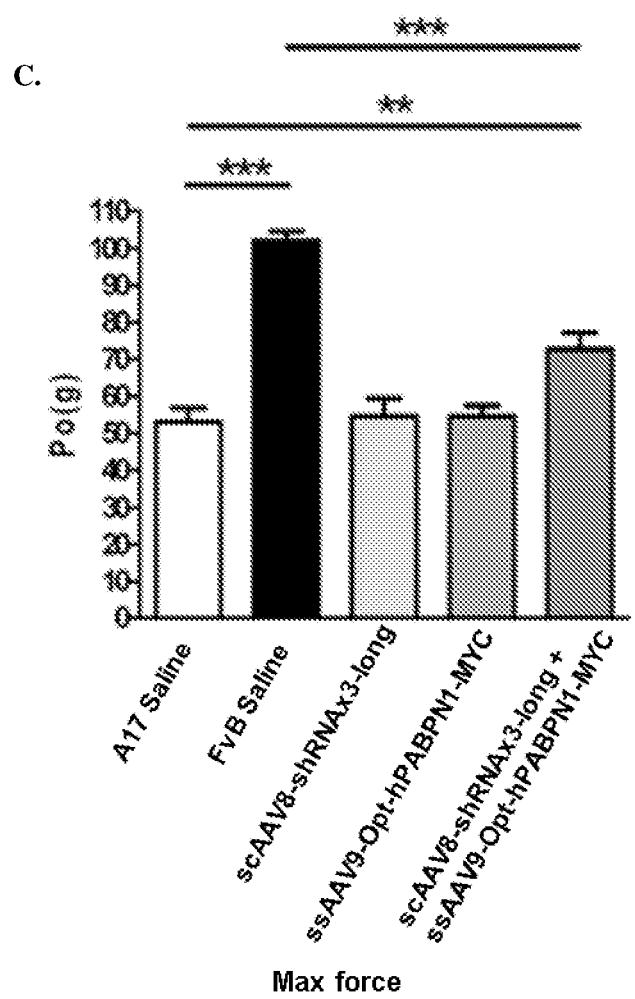

Staining was carried out on transverse serial cryosections of TA muscles (10 µm). The TA muscles were sectioned at 10-12 different intervals along the length of the muscle, allowing the maximal cross-sectional area (CSA) to be determined. For the assessment of tissue morphology and visualization of fibrosis and connective tissue, transverse sections of muscles were stained, respectively, with H&E and collagen VI for further examination under fluorescent light. To assess central nucleation, five random areas were assessed in each section. Images were visualized using an Olympus BX60 microscope (Olympus Optical, Hamburg, Germany), digitalized using a CCD camera (Photometrics CoolSNAP fx; Roper Scientific, Tucson, Ariz., USA) and analysed using MetaView image analysis system (Universal Imaging, Downington, Pa., USA). The total number of fibres in these areas was counted and the number of centrally nucleated fibres was expressed as a percentage of the total number of fibres (FIG. 5).

Western Blot Analysis

Western blot analysis was then performed on tissues to detect PABPN1. Briefly, muscle lysates were prepared by homogenising tissue in RIPA solution (NaCl 0.15M, HEPES 0.05M, NP-40 1%, sodium dehoxycholate 0.5%, SDS 0.10%, EDTA 0.01M) with protease inhibitor cocktail. Proteins were separated on 4-12% Bis-Tris gel (Invitrogen) and transferred onto a nitrocellulose membrane (Hybond ECL membrane; Amersham Biosciences), which was blocked by incubation in 5% milk in 0.1M PBS, 0.1% Tween-20. The nitrocellulose membrane was stained with primary antibodies raised against PABPN1 (abcam, 1/10,000) or mouse vinculin (Sigma, 1/10,000) as a house-keeping control. The nitrocellulose membrane was further incubated with HRP-conjugated anti-rabbit and anti-mouse secondary antibodies (Sigma, 1/2000 and 1/1000, respectively). Immunoreactive bands were detected with enhanced chemiluminescencereagent (ECL; Amersham Biosciences) and visualised by exposing the membrane to ECL Hyperfilm (Amersham Biosciences).

All data are presented as mean values±standard error of the mean (SEM) (cohort size stated per experiment). All statistical analyses were performed using the Student t-test. A difference was considered to be significant at $*P<0.05$, $P<0.01$ or $*P<0.001$.

Results

It was determined that whilst muscle mass (FIG. 5B) was not restored over the 4 month of treatment, overall muscle strength (FIG. 5A) was shown to be improved and specific muscle strength (FIG. 5C) normalised for mice in Group 3 administered (i) the scAAV8-shRNAx3-long viral particles expressing the three shRNAs targeting endogenous PABPN1 and (ii) the ssAAV8 Opt-hPABPN1 viral particles expressing replacement codon-optimised human PABN1 not targeted by the shRNAs (FIG. 5).

Figure 6:
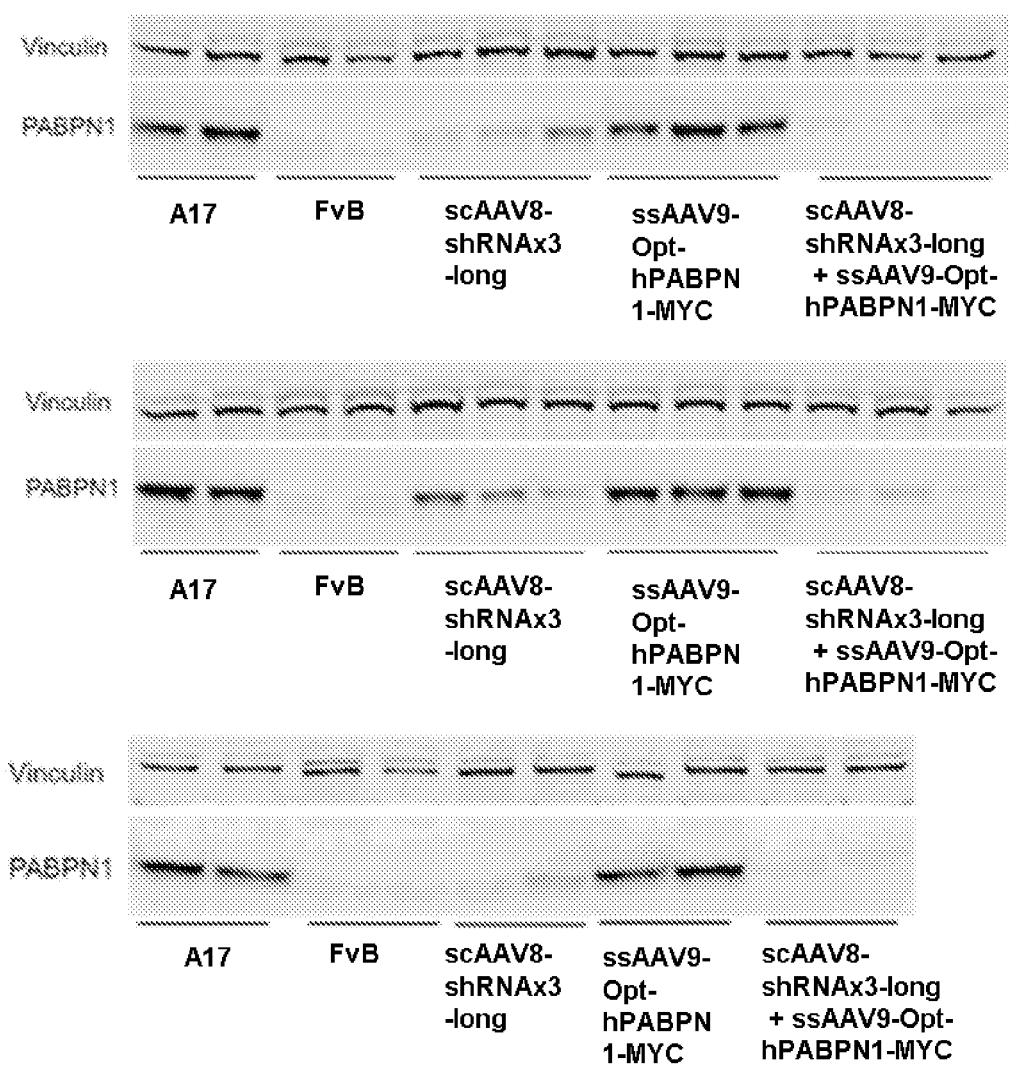
FIG. 6(A) is a western blot showing the average level of PABPN1 protein expression relative to vinculin protein expression in Tibialis anterior (TA) muscles from (i) A17 mice treated with saline, (ii) FvB mice treated with saline, (iii) A17 treated with scAAV8-shRNAx3-long, (iv) A17 treated with ssAAV9 Opt-hPABPN1-MYC and (v) A17 treated with scAAV8-shRNAx3-long and ssAAV9 Opt-hPABPN1-MYC.
FIG. 6(B) illustrates the level of PABPN1 protein expression in Tibialis anterior (TA) muscles from (i) A17 mice treated with saline, (ii) FvB mice treated with saline, (iii) A17 treated with scAAV8-shRNAx3-long, (iv) A17 treated with ssAAV9 Opt-hPABPN1-MYC and (v) A17 treated with scAAV8-shRNAx3-long and ssAAV9 Opt-hPABPN1-MYC, as determined by densiometric analysis of the western blot at FIG. 6(A).
FIG. 6(C) is a western blot showing the average level of MYC protein expression relative to vinculin protein expression in Tibialis anterior (TA) muscles from (i) A17 mice treated with saline, (ii) FvB mice treated with saline, (iii) A17 treated with scAAV8-shRNAx3-long, (iv) A17 treated with ssAAV9 Opt-hPABPN1-MYC and (v) A17 treated with scAAV8-shRNAx3-long and ssAAV9 Opt-hPABPN1-MYC. This western blot illustrates that the myc-epitope is detected in all muscles treated with ssAAV9 Opt-hPABPN1-MYC alone or in combination with scAAV8-shRNAx3-long. The arrow shows the band detected at the correct molecular weight.
FIG. 6(D) illustrates the level of Myc-tag detected in Tibialis anterior (TA) muscles from A17 mice 18 weeks post-injection with ssAAV9 Opt-hPABPN1-MYC alone or in combination with scAAV8-shRNAx3-long, as determined by densiometric analysis of the western blot at FIG. 6(C). This graph shows that scAAV8-shRNAx3-long does not affect optPABPN1 protein amount when co-expressed in muscles injected with both scAAV8-shRNAx3-long and ssAAV9 Opt-hPABPN1-MYC.
Figure 6:
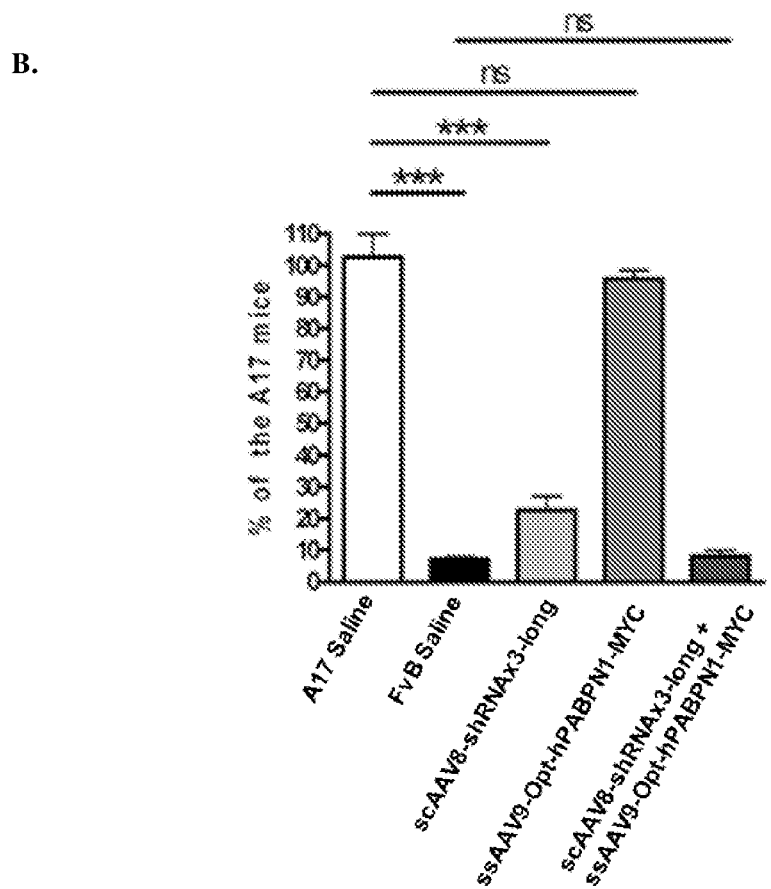
Figure 6:
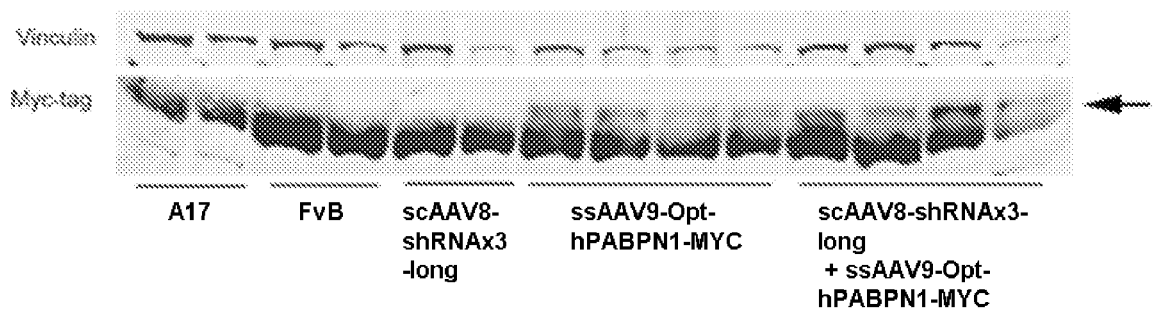
Figure 6:
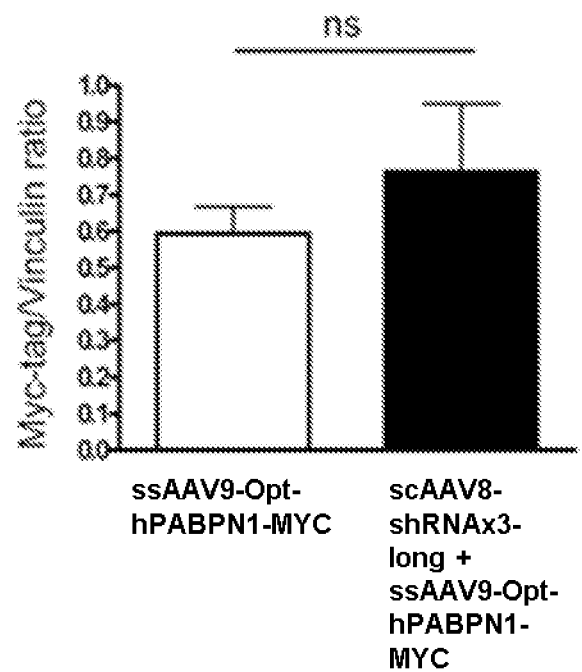

As is apparent from the western blot data presented in FIG. 6, A17 mice administered scAAV8-shRNAx3-long alone and in combination with ssAAV9 opt hPABPN1-myc showed significantly reduced levels of mutant expanded PABPN1 protein relative to mice administered saline only, demonstrating the ability of the scAAV-shRNAx3-long viral particles to inhibit expression of the endogenous mutant PABPN1 protein in vivo. Furthermore Myc-tag was equally expressed in mice treated with ssAAV9-optPABPN1-myc or with the combination of scAAV8-shRNAx3-long and ssAAV9-opt hPABPN1-myc.

Quantitative PCR confirmed these results, showing that scAAV8-shRNAx3-long resulted in 80% knock down in PABPN1 expression compare with mice administered saline only, and scAAV8-shRNAx3-long administered in combination with ssAAV9 opt hPABPN1-myc resulted in 90% knock down in PABPN1 expression compare with mice administered saline only.

Figure 7:
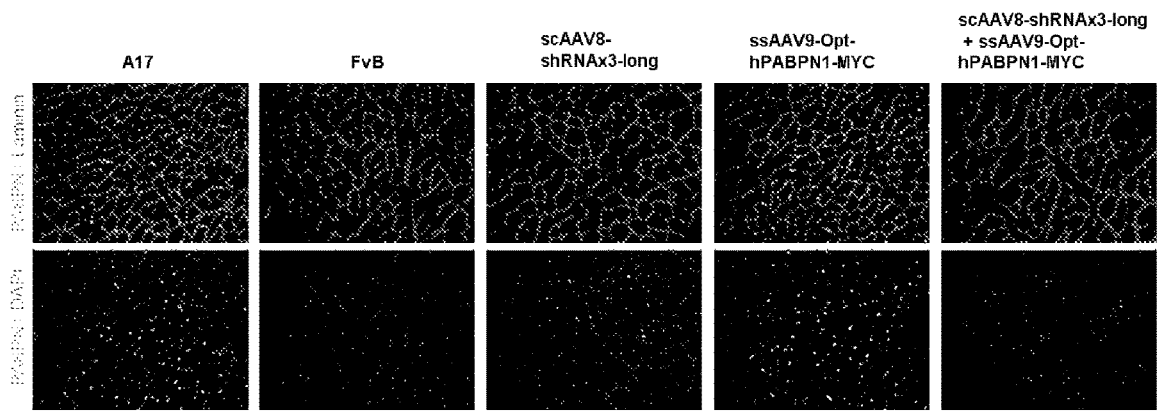
FIG. 7A shows immunofluorescence histochemistry for PABPN1 and laminin detection in sections of Tibialis anterior (TA) muscles from (i) A17 mice treated with saline, (ii) FvB mice treated with saline, (iii) A17 treated with scAAV8-shRNAx3-long, (iv) A17 treated with ssAAV9 Opt-hPABPN1-MYC and (v) A17 treated with scAAV8-shRNAx3-long and ssAAV9 Opt-hPABPN1-MYC. Sections were pre-treated with 1M KCl to discard all soluble PABPN1 from the tissue. The number of PABPN1 positive intranuclear inclusions (INIs) is significantly reduced in scAAV8-shRNAx3-long treated muscles. All muscle sections were taken 18 weeks post-injection.
FIG. 7B illustrates the level of nuclei containing INIs (expressed as a percentage) in sections of Tibialis anterior (TA) muscles from (i) A17 mice treated with saline, (ii) FvB mice treated with saline, (iii) A17 treated with scAAV8-shRNAx3-long, (iv) A17 treated with ssAAV9 Opt-hPABPN1-MYC and (v) A17 treated with scAAV8-shRNAx3-long and ssAAV9 Opt-hPABPN1-MYC. This graph illustrates that treatments with either scAAV8-shRNAx3-long, or both scAAV8-shRNAx3-long and ssAAV9 Opt-hPABPN1-MYC, reduces the amount of INIs to about 10% and 5% respectively compared to saline injected A17 muscles (CNF=35%) (One-way Anova test with Bonferroni post-doc test ***p<0.001).
Figure 7:
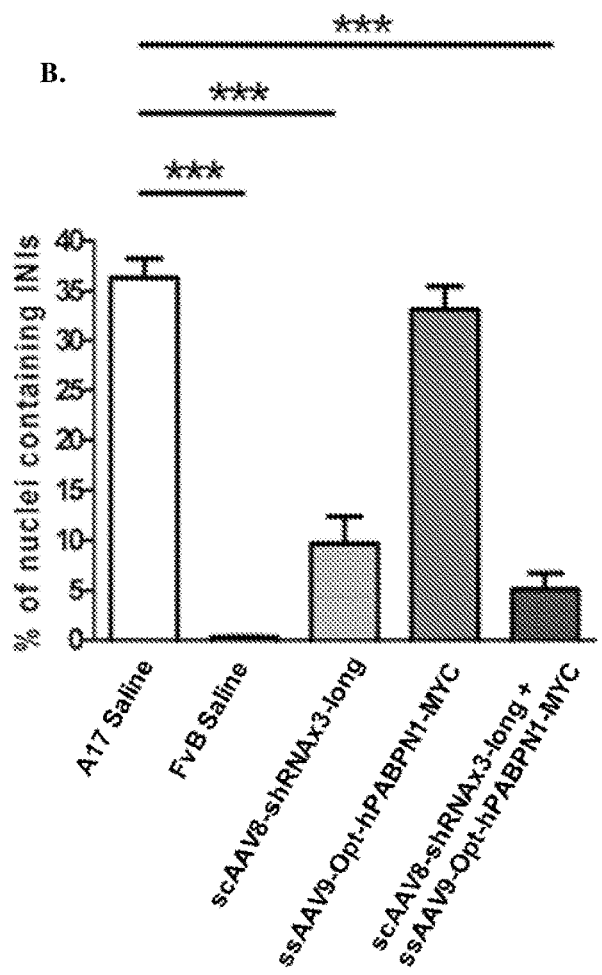
Figure 8:
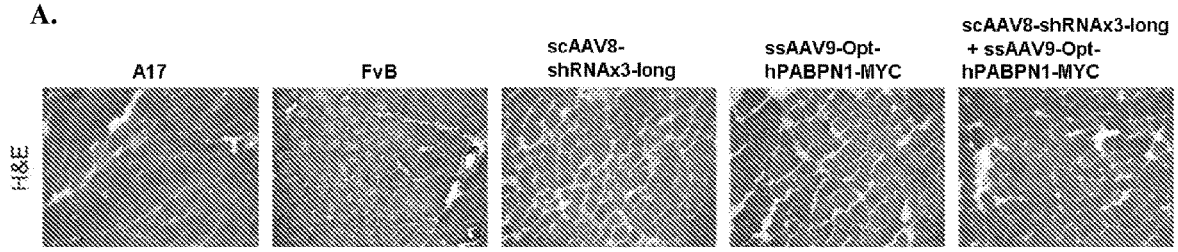
FIG. 8A shows images of Hematoxylin & Eosin (H&E) stained sections of Tibialis anterior (TA) muscle excised from (i) A17 mice injected with saline, (ii) FvB mice injected with saline, ((iii) A17 treated with scAAV8-shRNAx3-long, (iv) A17 treated with ssAAV9 Opt-hPABPN1-MYC and (v) A17 treated with scAAV8-shRNAx3-long and ssAAV9 Opt-hPABPN1-MYC. These images show that depleting endogenous PABPN1 in A17 muscles increases the amount of centrally nucleated fibres, whereas co-injecting ssAAV9-opt hPABPN1-MYC preserved the amount of fibres with central nuclei to the same level observed in saline injected A17 muscles, indicating that the co-expression of the codon-optimised hPABPN1 prevents muscle degeneration. All muscle sections were taken 18 weeks post-injection.
FIG. 8B provides representative images of immunostaining for Collagen VI in sections of Tibialis anterior (TA) muscle excised from (i) A17 mice injected with saline, (ii) FvB mice injected with saline, ((iii) A17 treated with scAAV8-shRNAx3-long, (iv) A17 treated with ssAAV9 Opt-hPABPN1-MYC and (v) A17 treated with scAAV8-shRNAx3-long and ssAAV9 Opt-hPABPN1-MYC. All muscle sections were taken 18 weeks post-injection.
FIG. 8C illustrates the percentage centrally nucleated (CN) fibres for sections of Tibialis anterior (TA) muscle excised from (i) A17 mice injected with saline, (ii) FvB mice injected with saline, ((iii) A17 treated with scAAV8-shR-NAx3-long, (iv) A17 treated with ssAAV9 Opt-hPABPN1-MYC and (v) A17 treated with scAAV8-shRNAx3-long and ssAAV9 Opt-hPABPN1-MYC. All muscle sections were taken 18 weeks post-injection.
FIG. 8D illustrates the percentage of Collagen VI positive area in sections of Tibialis anterior (TA) muscle excised from (i) A17 mice injected with saline, (ii) FvB mice injected with saline, ((iii) A17 treated with scAAV8-shR-NAx3-long, (iv) A17 treated with ssAAV9 Opt-hPABPN1-MYC and (v) A17 treated with scAAV8-shRNAx3-long and ssAAV9 Opt-hPABPN1-MYC. This graph shows a significant reduction in fibrosis in muscles treated with scAAV8-shRNAx3-long and ssAAV9 Opt-hPABPN1-MYC.
FIG. 8E illustrate average myofibre size per group and shows that myofibres of muscles treated with ssAAV9-opt hPABPN1-MYC alone or in combination with scAAV8-shRNAx3-long are larger than myofibres of muscles treated with saline (mean±SEM n=5-8, One-way Anova test with Bonferroni post-doc test, or Chi-squared analysis, *p<0.05, ***p<0.001, ns: non-significant)
FIG. 8F illustrates the distribution of myofiber cross sectional area (CSA) sections of Tibialis anterior (TA) muscle excised from (i) A17 mice injected with saline, (ii) FvB mice injected with saline, ((iii) A17 treated with scAAV8-shRNAx3-long, (iv) A17 treated with ssAAV9 Opt-hPABPN1-MYC and (v) A17 treated with scAAV8-shRNAx3-long and ssAAV9 Opt-hPABPN1-MYC. Comparison of different groups by Chi-squared analysis indicates changes in myofibre distribution for muscles treated with scAAV8-shRNAx3-long alone and in combination with ssAAV9 Opt-hPABPN1-MYC compared with animals administered saline only.
Figure 8:
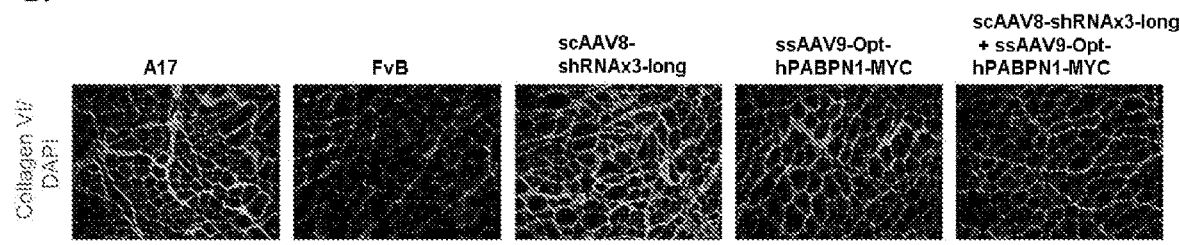
Figure 8:
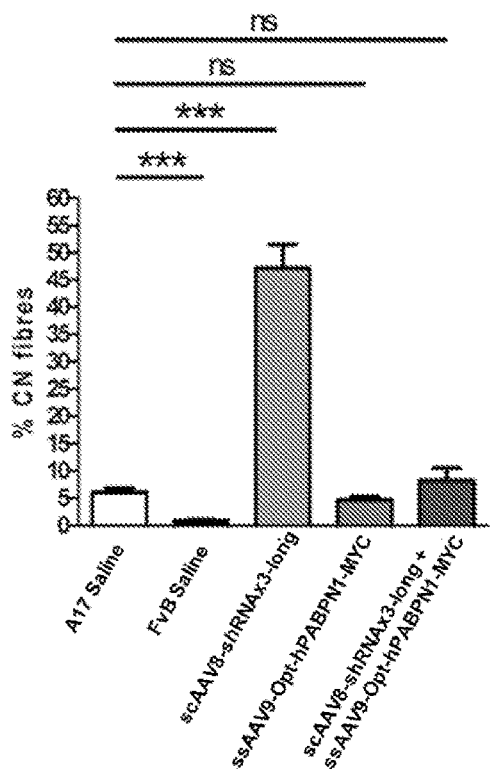
Figure 8:
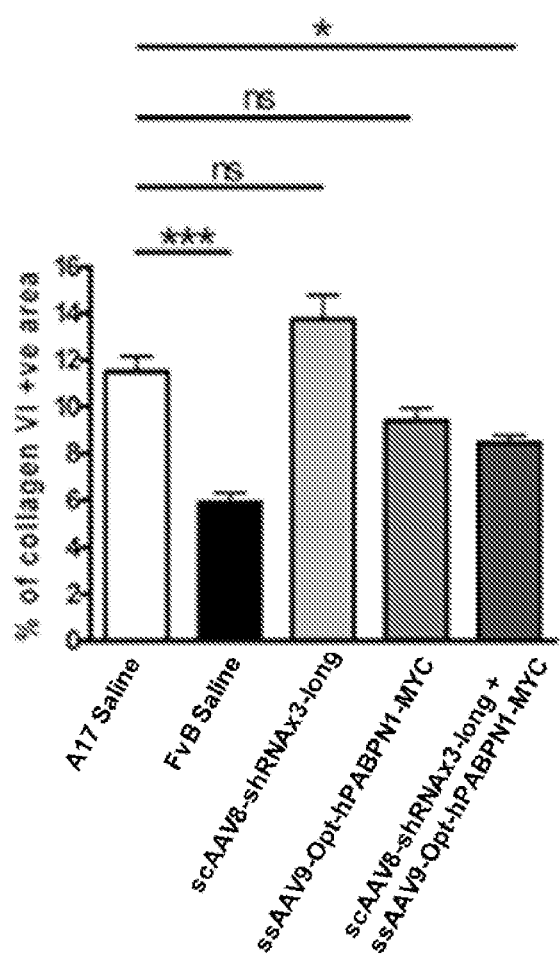
Figure 8:
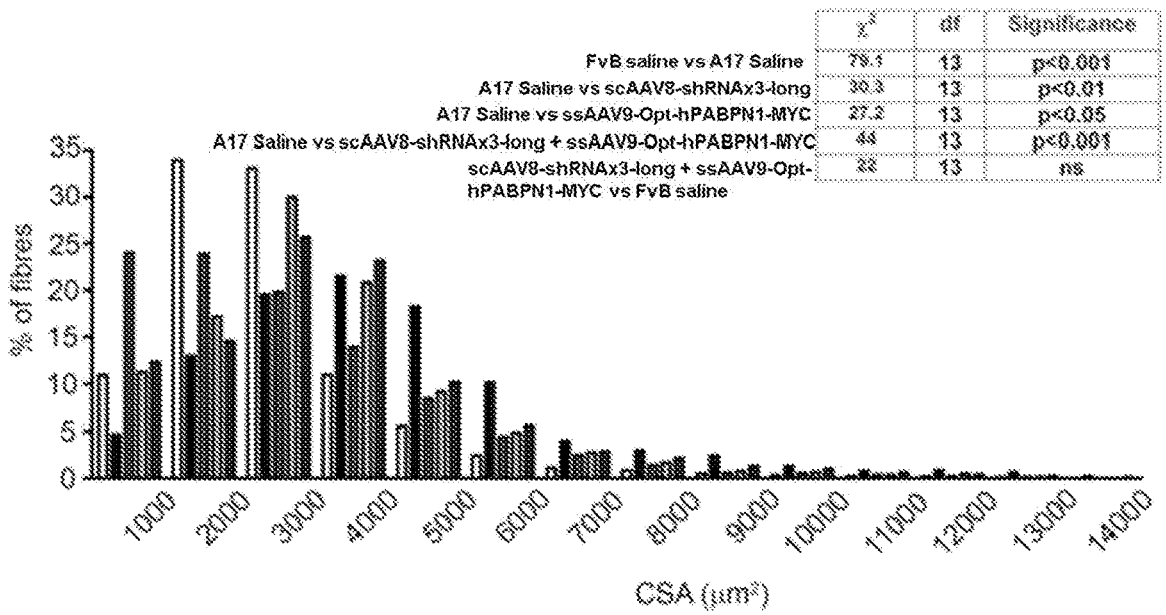
Figure 8:
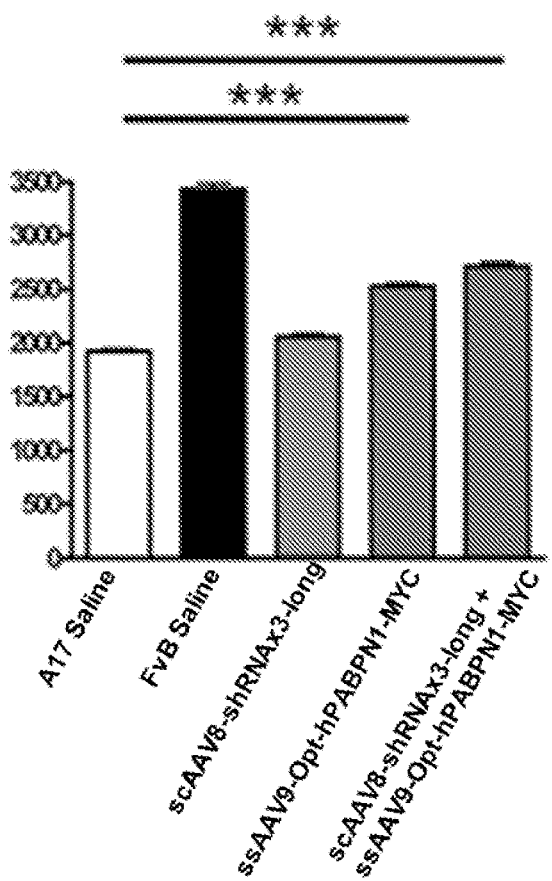

Histological and molecular analyses showed that silencing of endogenous PABPN1 almost abolishes nuclear aggregates (FIGS. 7A-B) and induce muscle degeneration as shown by increased amount of centrally nucleated fibres (FIG. 8A, C). In this regard, nuclear aggregates were detected in 35% of myonuclei in A17 mice while myonuclei from FvB mice contained virtually no aggregates. Whilst the expression of optPABPN1 did not modify the formation of insoluble aggregates in muscle of A17 mice, treatment with scAAV8-shRNAx3-long decreased the amount of myonuclei containing aggregates to 10%. The amount of myonucontaining aggregates was reduced to just 5% when scAAV8-shRNAx3-long was co-administered with ssAAV9-opt hPABPN1-myc expression the codon optimised PABPN1. Muscle degeneration was, however, shown to be reversed by co-expression of codon-optimised human PABPN1.

In the muscles from A17 mice treated with the combination of scAAV8-shRNAx3-long and ssAAV9 opt hPABPN1-myc, a significant reduction in fibrotic tissue was observed compared with muscles from A17 mice administered saline (FIG. 8B, D). Finally the analysis of myofibre cross sectional area (CSA) indicated that while injection of scAAV-shRNAx3-long alone did not modify the CSA of myofibres, the treatment with ssAAV9 Opt-hPABPN1-myc alone or in combination with scAAV-shRNAx3-long markedly increased the myofibre CSA (FIG. 8E-F).

Collectively, these data show that the shRNAx3-long construct delivered by AAV efficiently down-regulates PABPN1 in vivo and greatly reduces nuclear aggregates formation. Importantly, it has also been shown that a sequence-optimized PABPN1 can be expressed by rAAV in vivo to produce a transcript that is resistant to degradation and which restores muscle function. Taken together, these in vivo data demonstrate that suppression and replacement therapy is efficacious in restoring muscle functions in OPMD.

We claim:

1. A composition comprising:
   (a) a DNA-directed RNA interference (ddRNAi) construct comprising a nucleic acid comprising a DNA sequence encoding a hairpin RNA interference (RNAi) agent comprising an effector sequence and an effector complement sequence, wherein the effector sequence comprises a sequence of at least 17 contiguous nucleotides which is substantially complementary to a region of corresponding length in a RNA transcript corresponding to a PABPN1 protein, wherein the region of the RNA transcript is set forth in any one of SEQ ID NOs: 3, 1 or 2; and
   (b) a nucleic acid encoding a functional PABPN1 protein having a mRNA transcript which is not targeted by the RNAi agent encoded by the nucleic acid in the ddRNAi construct, wherein said nucleic acid encoding the functional PABPN1 protein is codon optimised and the functional PABPN1 protein comprises a sequence set forth in SEQ ID NO: 25.

2. The composition according to claim 1, wherein the RNAi agent is selected from the group consisting of:
   a RNAi agent comprising an effector sequence set forth in SEQ ID NO:4 and an effector complement sequence which is substantially complementary to the sequence set forth in SEQ ID NO:4;
   a RNAi agent comprising an effector sequence set forth in SEQ ID NO:6 and an effector complement sequence which is substantially complementary to the sequence set forth in SEQ ID NO:6; and
   a RNAi agent comprising an effector sequence set forth in SEQ ID NO:8 and an effector complement sequence which is substantially complementary to the sequence set forth in SEQ ID NO:8.

3. The composition according to claim 1, wherein the RNAi agent is selected from the group consisting of:
   a RNAi agent comprising an effector sequence set forth in SEQ ID NO:4 and an effector complement sequence set forth in SEQ ID NO:5;
   a RNAi agent comprising an effector sequence set forth in SEQ ID NO:6 and an effector complement sequence set forth in SEQ ID NO:7; and
   a RNAi agent comprising an effector sequence set forth in SEQ ID NO:8 and an effector complement sequence set forth in SEQ ID NO:9.

4. The composition according to claim 1, comprising a loop sequence positioned between the effector sequence and the effector complement sequence, optionally wherein the RNAi agent is a short hairpin RNA (shRNA).

5. The composition according to claim 4, encoding a shRNA comprising a sequence set forth in any one of SEQ ID NOs: 16-21.

6. The composition according to claim 1, wherein the ddRNAi agent comprises a DNA sequence encoding an shRNA comprising a sequence set forth in any one of SEQ ID NOs: 20, 21 or 16-19.

7. The composition according to claim 1, wherein the ddRNAi agent comprises a DNA sequence encoding an shRNA sequence set forth in SEQ ID NO: 20 or 21.

8. The composition according to claim 4, wherein the ddRNAi agent comprises a promoter upstream of the or each DNA sequence encoding a shRNA sequence, optionally wherein the promoter is a RNA pol III promoter selected from a U6 and a H1 promoter.

9. The composition according to claim 1, further comprising one or more pharmaceutically acceptable carriers.

10. The composition according to claim 1, wherein the ddRNAi construct is comprised within an expression vector, optionally wherein the expression vector is a viral vector selected from the group consisting of: an adeno-associated viral (AAV) vector, a retroviral vector, an adenoviral (AdV) vector and a lentiviral (LV) vector.

11. The composition according to claim 1, wherein the nucleic acid encoding the functional PABPN1 protein is set forth in SEQ ID NO: 24.

12. The composition according to claim 1, wherein the nucleic acid encoding the functional PABPN1 protein is comprised within an expression vector.

13. The composition according to claim 12, wherein the nucleic acid encoding the functional PABPN1 protein is comprised within the same expression vector as the nucleic acid encoding the RNAi agent, optionally wherein the expression vector is a viral vector selected from the group consisting of: an adeno-associated viral (AAV) vector, a retroviral vector, an adenoviral (AdV) vector and a lentiviral (LV) vector.

14. The composition according to claim 12, wherein the nucleic acid encoding the functional PABPN1 protein and the nucleic acid encoding the RNAi agent are comprised within different expression vectors, optionally wherein the expression vectors are viral vectors selected from the group consisting of: adeno-associated viral (AAV) vectors, retroviral vectors, adenoviral (AdV) vectors, lentiviral (LV) vectors and combinations thereof.

15. A method of inhibiting expression of a PABPN1 protein which is causative of oculopharyngeal muscular dystrophy (OPMD) in a subject, said method comprising administering to the subject a composition according to claim 1.

16. A method of treating oculopharyngeal muscular dystrophy (OPMD) in a subject suffering therefrom, said method comprising administering to the subject a composition according to claim 13.

17. A method of treating oculopharyngeal muscular dystrophy (OPMD) in a subject suffering therefrom, said method comprising administering to the subject the composition according to claim 14.

18. The method according to claim 17, wherein the nucleic acid encoding the functional PABPN1 protein is set forth in SEQ ID NO: 24.

19. The method according to claim 17, wherein the expression vector comprising the nucleic acid encoding the functional PABPN1 protein and expression vector comprising the nucleic acid encoding the RNAi agent are administered to the subject together, simultaneously or consecutively.

20. An expression vector comprising:
  (a) a DNA-directed RNA interference (ddRNAi) construct comprising a nucleic acid comprising a DNA sequence encoding a hairpin RNA interference (RNAi) agent comprising an effector sequence and an effector complement sequence, wherein the effector sequence comprises a sequence of at least 17 contiguous nucleotides which is substantially complementary to a region of corresponding length in a RNA transcript corresponding to a PABPN1 protein, wherein the region of the RNA transcript is set forth in any one of SEQ ID NOs: 3, 1 or 2; and
  (b) a nucleic acid encoding a functional PABPN1 protein having a mRNA transcript which is not targeted by the RNAi agent encoded by the nucleic acid in the ddRNAi construct, wherein said nucleic acid encoding the functional PABPN1 protein is codon optimised and the functional PABPN1 protein comprises a sequence set forth in SEQ ID NO: 25.

21. The expression vector of claim 20, wherein the expression vector is a viral vector selected from the group consisting of: an adeno-associated viral (AAV) vector, a retroviral vector, an adenoviral (AdV) vector and a lentiviral (LV) vector.

* * * * *

```
                         SEQUENCE LISTING

<160> NUMBER OF SEQ ID NOS: 29

<210> SEQ ID NO 1
<211> LENGTH: 23
<212> TYPE: RNA
<213> ORGANISM: Homo sapiens

<400> SEQUENCE: 1
uugaggagaa gauggaggcu gau                                          23

<210> SEQ ID NO 2
<211> LENGTH: 21
<212> TYPE: RNA
<213> ORGANISM: Homo sapiens

<400> SEQUENCE: 2
aggaagaagc ugagaagcua a                                            21

<210> SEQ ID NO 3
<211> LENGTH: 27
<212> TYPE: RNA
<213> ORGANISM: Homo sapiens

<400> SEQUENCE: 3
gagguagaga agcagaugaa uaugagu                                      27

<210> SEQ ID NO 4
<211> LENGTH: 23
<212> TYPE: RNA
<213> ORGANISM: artificial sequence
<220> FEATURE:
<223> OTHER INFORMATION: Effector sequence for ssRNA1 and dsRNA1

<400> SEQUENCE: 4
aucagccucc aucuucuccu caa                                          23

<210> SEQ ID NO 5
<211> LENGTH: 23
<212> TYPE: RNA
<213> ORGANISM: artificial sequence
<220> FEATURE:
<223> OTHER INFORMATION: Effector complement sequence for dsRNA1

<400> SEQUENCE: 5
uugaggagaa gauggaggcu gau                                          23

<210> SEQ ID NO 6
<211> LENGTH: 21
<212> TYPE: RNA
<213> ORGANISM: artificial sequence
<220> FEATURE:
```

<223> OTHER INFORMATION: Effector sequence for ssRNA2 and dsRNA2

<400> SEQUENCE: 6
uuagcuucuc agcuucuucc u                                         21

<210> SEQ ID NO 7
<211> LENGTH: 21
<212> TYPE: RNA
<213> ORGANISM: artificial sequence
<220> FEATURE:
<223> OTHER INFORMATION: Effector complement sequence for dsRNA2

<400> SEQUENCE: 7
aggaagaagc ugagaagcua a                                         21

<210> SEQ ID NO 8
<211> LENGTH: 27
<212> TYPE: RNA
<213> ORGANISM: artificial sequence
<220> FEATURE:
<223> OTHER INFORMATION: Effector sequence for ssRNA3 and dsRNA3

<400> SEQUENCE: 8
acucauauuc aucugcuucu cuaccuc                                   27

<210> SEQ ID NO 9
<211> LENGTH: 27
<212> TYPE: RNA
<213> ORGANISM: artificial sequence
<220> FEATURE:
<223> OTHER INFORMATION: Effector complement sequence for dsRNA3

<400> SEQUENCE: 9
gagguagaga agcagaugaa uaugagu                                   27

<210> SEQ ID NO 10
<211> LENGTH: 23
<212> TYPE: RNA
<213> ORGANISM: artificial sequence
<220> FEATURE:
<223> OTHER INFORMATION: Effector sequence for shRNA1 and shRNA2

<400> SEQUENCE: 10
aucagccucc aucuucuccu caa                                       23

<210> SEQ ID NO 11
<211> LENGTH: 23
<212> TYPE: RNA
<213> ORGANISM: artificial sequence
<220> FEATURE:
<223> OTHER INFORMATION: Effector complement sequence for shRNA1 and
      shRNA2

<400> SEQUENCE: 11
uugaggagaa gauggaggcu gau                                       23

<210> SEQ ID NO 12
<211> LENGTH: 21
<212> TYPE: RNA
<213> ORGANISM: artificial sequence
<220> FEATURE:
<223> OTHER INFORMATION: Effector sequence for shRNA3 and shRNA4

<400> SEQUENCE: 12
uuagcuucuc agcuucuucc u                                         21

<210> SEQ ID NO 13
<211> LENGTH: 21
<212> TYPE: RNA
<213> ORGANISM: artificial sequence
<220> FEATURE:
<223> OTHER INFORMATION: Effector complement sequence for shRNA3 and shRNA4

<400> SEQUENCE: 13
aggaagaagc ugagaagcua a                                              21

<210> SEQ ID NO 14
<211> LENGTH: 27
<212> TYPE: RNA
<213> ORGANISM: artificial sequence
<220> FEATURE:
<223> OTHER INFORMATION: Effector sequence for shRNA5 and shRNA6

<400> SEQUENCE: 14
acucauauuc aucugcuucu cuaccuc                                        27

<210> SEQ ID NO 15
<211> LENGTH: 27
<212> TYPE: RNA
<213> ORGANISM: artificial sequence
<220> FEATURE:
<223> OTHER INFORMATION: Effector complement sequence for shRNA5 and shRNA6

<400> SEQUENCE: 15
gagguagaga agcagaugaa uaugagu                                        27

<210> SEQ ID NO 16
<211> LENGTH: 49
<212> TYPE: RNA
<213> ORGANISM: artificial sequence
<220> FEATURE:
<223> OTHER INFORMATION: shRNA1 sequence

<400> SEQUENCE: 16
gaggagaaga uggaggcuga ucaagagaau cagccuccau cuucuccuc                49

<210> SEQ ID NO 17
<211> LENGTH: 49
<212> TYPE: RNA
<213> ORGANISM: artificial sequence
<220> FEATURE:
<223> OTHER INFORMATION: shRNA2 sequence

<400> SEQUENCE: 17
aucagccucc aucuucuccu ccaagagaga ggagaagaug gaggcugau                49

<210> SEQ ID NO 18
<211> LENGTH: 47
<212> TYPE: RNA
<213> ORGANISM: artificial sequence
<220> FEATURE:
<223> OTHER INFORMATION: shRNA3 sequence

<400> SEQUENCE: 18
ggaagaagcu gagaagcuaa caagagauua gcuucucagc uucuucc                  47

<210> SEQ ID NO 19
<211> LENGTH: 47
<212> TYPE: RNA
<213> ORGANISM: artificial sequence

```
<220> FEATURE:
<223> OTHER INFORMATION: shRNA4 sequence

<400> SEQUENCE: 19
uuagcuucuc agcuucuucc caagagagga agaagcugag aagcuaa         47

<210> SEQ ID NO 20
<211> LENGTH: 60
<212> TYPE: RNA
<213> ORGANISM: artificial sequence
<220> FEATURE:
<223> OTHER INFORMATION: shRNA5 sequence

<400> SEQUENCE: 20
gagguagaga agcagaugaa uaugagucaa gagacucaua uucaucugcu ucucuaccuc    60

<210> SEQ ID NO 21
<211> LENGTH: 60
<212> TYPE: RNA
<213> ORGANISM: artificial sequence
<220> FEATURE:
<223> OTHER INFORMATION: shRNA6 sequence

<400> SEQUENCE: 21
cucauauuca ucugcuucuc uaccuccaag agagagguag agaagcagau gaauaugagu    60

<210> SEQ ID NO 22
<211> LENGTH: 1068
<212> TYPE: DNA
<213> ORGANISM: artificial sequence
<220> FEATURE:
<223> OTHER INFORMATION: OPMD Triple construct short

<400> SEQUENCE: 22
ctcgagacgc gtggtaccga gctcgctagc agcgcttacg tatttaaatg gcaggaagag    60
ggcctatttc ccatgattcc ttcatatttg catatacgat acaaggctgt tagagagata   120
attagaatta atttgactgt aaacacaaag atattagtac aaaatacgtg acgtagaaag   180
taataatttc ttgggtagtt tgcagtttta aaattatgtt ttaaaatgga ctatcatatg   240
cttaccgtaa cttgaaagta tttcgatttc ttggctttat atatcttgtg aaaggacga   300 aacaccgagg agaagatgga ggctgatcaa gagaatcagc ctccatcttc tcctcttttt   360
tatgcgcacg tttaaacagg gcggtgcggc tcaggctctg ccccgcctcc ggggctattt   420
gcatacgacc atttccagta attcccagca gccaccgtag ctatatttgg tagaacaacg   480
agcactttct caactccagt caataactac gttagttgca ttacacattg gctaatata    540 aatagaggtt aaatctctag gtcatttaag agaagtcggc ctatgtgtac agacatttgt   600
tccaggggct ttaaatagct ggtggtggaa ctcaatattc ggaagaagct gagaagctaa   660
caagagatta gcttctcagc ttcttccttt tttgtatacg ataccatca attcgaacgc    720 tgacgtcatc aaccccgctcc aaggaatcgc gggcccagtg tcactaggcg gaacaccca   780 gcgcgcgtgc gccctggcag gaagatggct gtgagggaca ggggagtggc gccctgcaat   840
atttgcatgt cgctatgtgt tctgggaaat caccataaac gtgaaatgtc tttggatttg   900
ggaatcttat aagttctgta tgagaccaca gatccccgag gtagagaagc agatgaatat   960
gagttcaaga gactcatatt catctgcttc tctacctctt tttgacacac gtcctgcagc  1020
gttaaccaat gccacggggt tggggtacca cgcgtgagc tcctcgag              1068

<210> SEQ ID NO 23
```

<211> LENGTH: 1527
<212> TYPE: DNA
<213> ORGANISM: artificial sequence
<220> FEATURE:
<223> OTHER INFORMATION: OPMD Triple construct long

<400> SEQUENCE: 23

```
ctcgagacgc gtggtaccga gctcgctagc agcgcttacg tatttaaatg gcaggaagag      60
ggcctatttc ccatgattcc ttcatatttg catatacgat acaaggctgt tagagagata     120
attagaatta atttgactgt aaacacaaag atattagtac aaaatacgtg acgtagaaag     180
taataatttc ttgggtagtt tgcagtttta aaattatgtt ttaaaatgga ctatcatata     240
agatgggctt accgtaactt gaaagtattt cgatttcttg ctttatata tcttgtggaa      300
aggacgaaac accgaggaga agatggaggc tgatcaagag aatcagcctc catcttctcc     360
tcttttttac atcaggttgt ttttctgttt ttacatcagg ttgttttct gtttggtttt      420
tttttacac cacgtttata cgccggtgca cggtttacca ctgaaaacac ctttcatcta      480
caggtgatat cttttaacac aaataaaatg tagtagtcca tgcgcacgtt taaacaaggg     540
cggtgcggct caggctctgc cccgcctccg ggctatttg catacgacca tttccagtaa      600
ttcccagcag ccaccgtagc tatatttggt agaacaacga gcactttctc aactccagtc     660
aataactacg ttagttgcat tacacattgg gctaatataa atagaggtta aatctctagg     720
tcatttaaga gaagtcggcc tatgtgtaca gacatttgtt ccaggggctt taaatagctg     780
gtggtggaac tcaatattcg gaagaagctg agaagctaac aagagattag cttctcagct     840
tcttcctttt ttccattttc cctcccagaa acggaatctt gctctgttgc ccaggctgga     900
atgcaatggc gcgatcttag cttgttgcaa cctccgcctc ccgggttgaa gcgattctcc     960
tgcctcagcc tcccgagtag ctgggattat aaacatgcgc cagtatacga tacctatcaa    1020
ttcgaacgct gacgtcatca acccgctcca aggaatcgcg ggcccagtgt cactaggcgg    1080
gaacacccag cgcgcgtgcg ccctggcagg aagatggctg tgaggacag gggagtggcg     1140
ccctgcaata tttgcatgtc gctatgtgtt ctgggaaatc accataaacg tgaaatgtct    1200
ttggatttgg gaatcttata agttctgtat gagaccacag atccccgagg tagagaagca    1260
gatgaatatg agttcaagag actcatattc atctgcttct ctacctcttt ttaaacaaaa    1320
cgaaaccggg ccgggcgcgg tggttcacgc ctataatccc tgcactttgg gaggccgagg    1380
cgggcggatc acaaggtcag gaggtcgaga ccatccaggc taacacggtg aaaccccccc    1440
ccatctctac taaaaaaaaa aagacacacg tcctgcagcg ttaaccaatt gccacggggt    1500
tggggtacca cgcgtgagct cctcgag                                        1527
```

<210> SEQ ID NO 24
<211> LENGTH: 950
<212> TYPE: DNA
<213> ORGANISM: artificial sequence
<220> FEATURE:
<223> OTHER INFORMATION: Human codon-optimized PABpN1 cDNA sequence
      (with kozak sequence but without myc-tag)

<400> SEQUENCE: 24

```
ccgctgccgc cgctgctgct gccgcagccg gcgctgccgg cggaagaggc agcggccctg      60
gcagacggcg gcatctggtc cctggcgccg gaggggaggc cggcgaaggc gcccctggcg    120
gagccggcga ctacggcaac ggcctggaaa gcgaggaact ggaacccgag gaactgctgc    180
tggaacctga gcccgagcca gagcccgagg aagagccccc taggccaaga gccccccctg    240
```

```
gcgccccagg accaggacca ggctctgggg caccaggctc tcaggaagag gaagaagagc    300
ccggcctcgt cgagggagac ccaggcgatg gcgctatcga agatcccgag ctggaagcca    360
tcaaggccag agtgcgggag atggaagagg aggccgaaaa attgaaagag ctgcagaacg    420
aagtcgaaaa acaaatgaac atgtcccccc ctcctggaaa tgctggccct gtgatcatga    480
gcatcgagga aaagatggaa gccgacgccc ggtctatcta cgtgggcaac gtggactacg    540
gcgccaccgc cgaagaactg gaagcccact tcacggctg tggcagcgtg aaccgggtga    600
ccatcctgtg cgacaagttc agcggccacc ccaagggctt cgcctacatc gagttcagcg    660
acaaagaaag cgtgcggacc tctctggctc tcgacgagtc tctgttcagg ggaaggcaga    720
tcaaggtcat ccccaagcgg accaacaggc ccggcatcag caccaccgac agaggcttcc    780
ctagggctag gtacagagcc cggaccacca actacaacag cagcagaagc cggttctaca    840
gcggcttcaa ttctcggcct agaggcagag tgtaccgggg cagggccagg gccacctcct    900
ggtacagccc ctactgaacc tcctggtaca gccctactg atgagatatc                950
```

```
<210> SEQ ID NO 25
<211> LENGTH: 306
<212> TYPE: PRT
<213> ORGANISM: artificial sequence
<220> FEATURE:
<223> OTHER INFORMATION: Human codon-optimized PABpN1 amino acid
      sequence (without Myc-tag)

<400> SEQUENCE: 25

Met Ala Ala Ala Ala Ala Ala Ala Ala Gly Ala Ala Gly Gly
1               5                   10                  15

Arg Gly Ser Gly Pro Gly Arg Arg His Leu Val Pro Gly Ala Gly
                20                  25                  30

Gly Glu Ala Gly Glu Gly Ala Pro Gly Gly Ala Gly Asp Tyr Gly Asn
            35                  40                  45

Gly Leu Glu Ser Glu Glu Leu Glu Pro Glu Glu Leu Leu Glu Pro
        50                  55                  60

Glu Pro Glu Pro Glu Pro Glu Glu Pro Pro Arg Pro Arg Ala Pro
65                  70                  75                  80

Pro Gly Ala Pro Gly Pro Gly Pro Ser Gly Ala Pro Gly Ser Gln
                85                  90                  95

Glu Glu Glu Glu Glu Pro Gly Leu Val Glu Gly Asp Pro Gly Asp Gly
            100                 105                 110

Ala Ile Glu Asp Pro Glu Leu Glu Ala Ile Lys Ala Arg Val Arg Glu
        115                 120                 125

Met Glu Glu Glu Ala Glu Lys Leu Lys Glu Leu Gln Asn Glu Val Glu
    130                 135                 140

Lys Gln Met Asn Met Ser Pro Pro Gly Asn Ala Gly Pro Val Ile
145                 150                 155                 160

Met Ser Ile Glu Glu Lys Met Glu Ala Asp Ala Arg Ser Ile Tyr Val
                165                 170                 175

Gly Asn Val Asp Tyr Gly Ala Thr Ala Glu Glu Leu Glu Ala His Phe
            180                 185                 190

His Gly Cys Gly Ser Val Asn Arg Val Thr Ile Leu Cys Asp Lys Phe
        195                 200                 205

Ser Gly His Pro Lys Gly Phe Ala Tyr Ile Glu Phe Ser Asp Lys Glu
    210                 215                 220

Ser Val Arg Thr Ser Leu Ala Leu Asp Glu Ser Leu Phe Arg Gly Arg
225                 230                 235                 240
```

Gln Ile Lys Val Ile Pro Lys Arg Thr Asn Arg Pro Gly Ile Ser Thr
            245                 250                 255

Thr Asp Arg Gly Phe Pro Arg Ala Arg Tyr Arg Ala Arg Thr Thr Asn
        260                 265                 270

Tyr Asn Ser Ser Arg Ser Arg Phe Tyr Ser Gly Phe Asn Ser Arg Pro
    275                 280                 285

Arg Gly Arg Val Tyr Arg Gly Arg Ala Arg Ala Thr Ser Trp Tyr Ser
290                 295                 300

Pro Tyr
305

<210> SEQ ID NO 26
<211> LENGTH: 947
<212> TYPE: DNA
<213> ORGANISM: artificial sequence
<220> FEATURE:
<223> OTHER INFORMATION: Human codon-optimized PABpN1 cDNA sequence
      (with kozak sequence and Myc-tag)

<400> SEQUENCE: 26
ccgctgccgc cgctgctgct gccgcagccg gcgctgccgg cggaagaggc agcggccctg      60
gcagacggcg gcatctggtc cctggcgccg gaggggaggc cggcgaaggc gcccctggcg     120
gagccggcga ctacggcaac ggcctggaaa gcgaggaact ggaacccgag gaactgctgc     180
tggaacctga gcccgagcca gagcccgagg aagagccccc taggccaaga gccccccctg     240
gcgccccagg accaggacca ggctctgggg caccaggctc tcaggaagag gaagaagagc     300
ccggcctcgt cgagggagac ccaggcgatg gcgctatcga agatcccgag ctggaagcca     360
tcaaggccag agtgcgggag atggaagagg aggccgaaaa attgaaagag ctgcagaacg     420
aagtcgaaaa acaaatgaac atgtccccc ctcctggaaa tgctggccct gtgatcatga     480
gcatcgagga aaagatggaa gccgacgccc ggtctatcta cgtgggcaac gtggactacg     540
gcgccaccgc cgaagaactg aagcccact ttcacggctg tggcagcgtg aaccgggtga     600
ccatcctgtg cgacaagttc agcggccacc ccaagggctt cgcctacatc gagttcagcg     660
acaaagaaag cgtgcggacc tctctggctc tcgacgagtc tctgttcagg ggaaggcaga     720
tcaaggtcat ccccaagcgg accaacaggc ccggcatcag caccaccgac agaggcttcc     780
ctagggctag gtacagagcc cggaccacca actacaacag cagcagaagc cggttctaca     840
gcggcttcaa ttctcggcct agaggcagag tgtaccgggg cagggccagg gccacctcct     900
ggtacagccc ctacgaacag aagctgatca gcgaggaaga tctgtga               947

<210> SEQ ID NO 27
<211> LENGTH: 316
<212> TYPE: PRT
<213> ORGANISM: artificial sequence
<220> FEATURE:
<223> OTHER INFORMATION: Human codon-optimized PABpN1 amino acid
      sequence (with Myc-tag)

<400> SEQUENCE: 27

Met Ala Ala Ala Ala Ala Ala Ala Ala Gly Ala Ala Gly Gly
1               5                   10                  15

Arg Gly Ser Gly Pro Gly Arg Arg His Leu Val Pro Gly Ala Gly
            20                  25                  30

Gly Glu Ala Gly Glu Gly Ala Pro Gly Gly Ala Gly Asp Tyr Gly Asn
        35                  40                  45

Gly Leu Glu Ser Glu Glu Leu Glu Pro Glu Leu Leu Glu Pro
    50                  55                  60

Glu Pro Glu Pro Glu Pro Glu Glu Glu Pro Pro Arg Pro Arg Ala Pro
65                  70                  75                  80

Pro Gly Ala Pro Gly Pro Gly Pro Gly Ser Gly Ala Pro Gly Ser Gln
                85                  90                  95

Glu Glu Glu Glu Glu Pro Gly Leu Val Gly Asp Pro Gly Asp Gly
                100                 105                 110

Ala Ile Glu Asp Pro Glu Leu Glu Ala Ile Lys Ala Arg Val Arg Glu
            115                 120                 125

Met Glu Glu Glu Ala Glu Lys Leu Lys Glu Leu Gln Asn Glu Val Glu
    130                 135                 140

Lys Gln Met Asn Met Ser Pro Pro Pro Gly Asn Ala Gly Pro Val Ile
145                 150                 155                 160

Met Ser Ile Glu Glu Lys Met Glu Ala Asp Ala Arg Ser Ile Tyr Val
                165                 170                 175

Gly Asn Val Asp Tyr Gly Ala Thr Ala Glu Glu Leu Glu Ala His Phe
            180                 185                 190

His Gly Cys Gly Ser Val Asn Arg Val Thr Ile Leu Cys Asp Lys Phe
        195                 200                 205

Ser Gly His Pro Lys Gly Phe Ala Tyr Ile Glu Phe Ser Asp Lys Glu
    210                 215                 220

Ser Val Arg Thr Ser Leu Ala Leu Asp Glu Ser Leu Phe Arg Gly Arg
225                 230                 235                 240

Gln Ile Lys Val Ile Pro Lys Arg Thr Asn Arg Pro Gly Ile Ser Thr
                245                 250                 255

Thr Asp Arg Gly Phe Pro Arg Ala Arg Tyr Arg Ala Arg Thr Thr Asn
            260                 265                 270

Tyr Asn Ser Ser Arg Ser Arg Phe Tyr Ser Gly Phe Asn Ser Arg Pro
        275                 280                 285

Arg Gly Arg Val Tyr Arg Gly Arg Ala Arg Ala Thr Ser Trp Tyr Ser
    290                 295                 300

Pro Tyr Glu Gln Lys Leu Ile Ser Glu Glu Asp Leu
305                 310                 315

<210> SEQ ID NO 28
<211> LENGTH: 945
<212> TYPE: DNA
<213> ORGANISM: artificial sequence
<220> FEATURE:
<223> OTHER INFORMATION: Mutant human PABpN1 cDNA sequence (with FLAG
      tag)

<400> SEQUENCE: 28
atggcggcgg cggcggcggc ggcagcagca gcggggggctg cgggcggtcg gggctccggg      60
ccggggcggc ggcgccatct tgtgcccggg gccggtgggg aggccgggga ggggccccg      120 gggggcgcag gggactacgg gaacggcctg gagtctgagg aactggagcc tgaggagctg     180
ctgctggagc ccgagccgga gcccgagccc gaagaggagc cgccccggcc ccgcgccccc     240 ccggagctc cggccctgg gcctggttcg ggagccccg gcagccaaga ggaggaggag     300
gagccgggac tggtcgaggg tgacccgggg gacggcgcca ttgaggaccc ggagctggaa     360
gctatcaaag ctcgagtcag ggagatggag gaagaagctg agaagctaaa ggagctacag     420
aacgaggtag agaagcagat gaatatgagt ccacctccag gcaatgctgg cccggtgatc     480
atgtccattg aggagaagat ggaggctgat gcccgttcca tctatgttgg caatgtggac     540

```
tatggtgcaa cagcagaaga gctggaagct cactttcatg gctgtggttc agtcaaccgt    600
gttaccatac tgtgtgacaa atttagtggc catcccaaag ggtttgcgta tatagagttc    660
tcagacaaag agtcagtgag gacttccttg gccttagatg agtccctatt tagaggaagg    720
caaatcaagg tgatcccaaa acgaaccaac agaccaggca tcagcacaac agaccggggt    780
tttccacgag cccgctaccg cgcccggacc accaactaca acagctcccg ctctcgattc    840
tacagtggtt ttaacagcag gccccggggt cgcgtctaca ggggccgggc tagagcgaca    900
tcatggtatt ccccttacga ctacaaggac gacgatgaca agtga                    945
```

<210> SEQ ID NO 29
<211> LENGTH: 314
<212> TYPE: PRT
<213> ORGANISM: artificial sequence
<220> FEATURE:
<223> OTHER INFORMATION: Mutant human PABpN1 amino acid sequence (with FLAG tag)

<400> SEQUENCE: 29

```
Met Ala Ala Ala Ala Ala Ala Ala Ala Gly Ala Ala Gly Gly
1               5                   10                  15

Arg Gly Ser Gly Pro Gly Arg Arg His Leu Val Pro Gly Ala Gly
                20                  25                  30

Gly Glu Ala Gly Glu Ala Pro Gly Gly Ala Gly Asp Tyr Gly Asn
            35                  40                  45

Gly Leu Glu Ser Glu Glu Leu Glu Pro Glu Glu Leu Leu Glu Pro
        50                  55                  60

Glu Pro Glu Pro Glu Pro Glu Glu Pro Pro Arg Pro Arg Ala Pro
65                  70                  75                  80

Pro Gly Ala Pro Gly Pro Gly Pro Gly Ser Gly Ala Pro Gly Ser Gln
                85                  90                  95

Glu Glu Glu Glu Glu Pro Gly Leu Val Glu Gly Asp Pro Gly Asp Gly
            100                 105                 110

Ala Ile Glu Asp Pro Glu Leu Glu Ala Ile Lys Ala Arg Val Arg Glu
        115                 120                 125

Met Glu Glu Glu Ala Glu Lys Leu Lys Glu Leu Gln Asn Glu Val Glu
    130                 135                 140

Lys Gln Met Asn Met Ser Pro Pro Gly Asn Ala Gly Pro Val Ile
145                 150                 155                 160

Met Ser Ile Glu Glu Lys Met Glu Ala Asp Ala Arg Ser Ile Tyr Val
                165                 170                 175

Gly Asn Val Asp Tyr Gly Ala Thr Ala Glu Glu Leu Glu Ala His Phe
            180                 185                 190

His Gly Cys Gly Ser Val Asn Arg Val Thr Ile Leu Cys Asp Lys Phe
        195                 200                 205

Ser Gly His Pro Lys Gly Phe Ala Tyr Ile Glu Phe Ser Asp Lys Glu
    210                 215                 220

Ser Val Arg Thr Ser Leu Ala Leu Asp Glu Ser Leu Phe Arg Gly Arg
225                 230                 235                 240

Gln Ile Lys Val Ile Pro Lys Arg Thr Asn Arg Pro Gly Ile Ser Thr
                245                 250                 255

Thr Asp Arg Gly Phe Pro Arg Ala Arg Tyr Arg Ala Arg Thr Thr Asn
            260                 265                 270

Tyr Asn Ser Ser Arg Ser Arg Phe Tyr Ser Gly Phe Asn Ser Arg Pro
        275                 280                 285
```

```
Arg Gly Arg Val Tyr Arg Gly Arg Ala Arg Ala Thr Ser Trp Tyr Ser
    290                 295                 300

Pro Tyr Asp Tyr Lys Asp Asp Asp Lys
305                 310
```